(12) United States Patent
Takamori et al.

(10) Patent No.: US 10,870,102 B2
(45) Date of Patent: Dec. 22, 2020

(54) RADICAL GENERATING CATALYST, METHOD FOR PRODUCING RADICAL, METHOD FOR PRODUCING OXIDATION REACTION PRODUCT, DRUG, AND DRUG FOR AGRICULTURE AND LIVESTOCK

(71) Applicant: ACENET INC., Tokyo (JP)

(72) Inventors: Kiyoto Takamori, Tokyo (JP); Takekatsu Shibata, Tokyo (JP)

(73) Assignee: ACENET INC., Tokyo (JP)

( * ) Notice: Subject to any disclaimer, the term of this patent is extended or adjusted under 35 U.S.C. 154(b) by 0 days.

(21) Appl. No.: 16/062,499

(22) PCT Filed: Dec. 16, 2016

(86) PCT No.: PCT/JP2016/087539
§ 371 (c)(1),
(2) Date: Jun. 14, 2018

(87) PCT Pub. No.: WO2017/104797
PCT Pub. Date: Jun. 22, 2017

(65) Prior Publication Data
US 2018/0369798 A1  Dec. 27, 2018

(30) Foreign Application Priority Data
Dec. 18, 2015 (JP) ................. 2015-248068

(51) Int. Cl.
| | | |
|---|---|---|
| B01J 31/02 | (2006.01) | |
| C07D 219/06 | (2006.01) | |
| C07C 63/06 | (2006.01) | |
| C07C 51/235 | (2006.01) | |
| C07F 15/06 | (2006.01) | |
| A61P 31/04 | (2006.01) | |
| A61K 31/14 | (2006.01) | |
| A61K 33/20 | (2006.01) | |
| C07B 61/00 | (2006.01) | |
| C07C 29/48 | (2006.01) | |
| C07F 9/53 | (2006.01) | |

(52) U.S. Cl.
CPC .......... *B01J 31/0239* (2013.01); *A61K 31/14* (2013.01); *A61K 33/20* (2013.01); *A61P 31/04* (2018.01); *B01J 31/0204* (2013.01); *B01J 31/0224* (2013.01); *B01J 31/0271* (2013.01); *C07B 61/02* (2013.01); *C07C 29/48* (2013.01); *C07C 51/235* (2013.01); *C07C 63/06* (2013.01); *C07D 219/06* (2013.01); *C07F 15/06* (2013.01); *C07F 15/065* (2013.01); *B01J 2231/70* (2013.01); *C07B 61/00* (2013.01); *C07F 9/53* (2013.01)

(58) Field of Classification Search
None
See application file for complete search history.

(56) References Cited

U.S. PATENT DOCUMENTS

| | | | | |
|---|---|---|---|---|
| 5,611,938 A | * | 3/1997 | Smolik | ...... C02F 1/50 |
| | | | | 210/755 |
| 2012/0322124 A1 | * | 12/2012 | Okull | ...... C12P 7/06 |
| | | | | 435/165 |
| 2013/0287722 A1 | | 10/2013 | Uhlmann | |

FOREIGN PATENT DOCUMENTS

| | | | | |
|---|---|---|---|---|
| CN | 103282507 | | 9/2013 | |
| DE | 858 998 | | 12/1952 | |
| JP | 60-181047 | | 9/1985 | |
| JP | 64-034904 | | 2/1989 | |
| JP | 2-104509 | | 4/1990 | |
| JP | 02104509 A | * | 4/1990 | ............ A01N 59/08 |
| JP | 2-268107 | | 11/1990 | |
| JP | 3-179363 | | 8/1991 | |
| JP | 3-179364 | | 8/1991 | |
| JP | 3-294245 | | 12/1991 | |
| JP | 2002-512980 | | 5/2002 | |
| JP | 2005-514658 | | 5/2005 | |
| JP | 2005-305109 | | 11/2005 | |
| JP | 2009-517720 | | 4/2009 | |
| JP | 2009-100850 | | 5/2009 | |
| JP | 2010-508900 | | 3/2010 | |
| JP | 2013-522312 | | 6/2013 | |
| JP | 2014-503457 | | 2/2014 | |
| JP | 2014-091063 | | 5/2014 | |
| JP | 2015-525127 | | 9/2015 | |
| WO | 99/55374 | | 11/1999 | |
| WO | 03/058346 | | 7/2003 | |
| WO | 2007/064527 | | 6/2007 | |
| WO | 2008/057439 | | 5/2008 | |

(Continued)

OTHER PUBLICATIONS

H. Dodgen et al., "The Exchange of Chlorine Dioxide with Chlorite Ion and with Chlorine in Other Oxidation States", Journal of the American Chemical Society, 1949, vol. 71, No. 7, pp. 2501-2504.

(Continued)

*Primary Examiner* — Brian J Davis
(74) *Attorney, Agent, or Firm* — Hamre, Schumann, Mueller & Larson, P.C.

(57) ABSTRACT

An object of a first aspect of the present invention is to provide a radical generating catalyst that can generate (produce) radicals under mild conditions. In order to achieve the above object, a first radical generating catalyst according to the first aspect of the present invention is characterized in that it includes ammonium and/or a salt thereof. A second radical generating catalyst according to the first aspect of the present invention is characterized in that it includes an organic compound having Lewis acidic properties and/or Brønsted acidic properties.

6 Claims, 13 Drawing Sheets

(56) References Cited

FOREIGN PATENT DOCUMENTS

| WO | 2011/116020 | 9/2011 |
| WO | 2013/184994 | 12/2013 |

OTHER PUBLICATIONS

Jessica K. Leigh et al., "Kinetics and Mechanism of Styrene Epoxidation by Chlorite: Role of Chlorine Dioxide", Inorganic Chemistry, 2014, vol. 53, pp. 6715-6727.

Latshaw, "Chlorine dioxide: effective, broad-spectrum biocide for white-water systems", Tappi Journal, 1994, vol. 78, No. 4, pp. 163-166.

J. J. Leddy, "Salt, Chlor-Alkali and Related Heavy Chemicals", Riegel's Handbook of Industrial Chemistry, 8th edn. Ed., J. A. Kent, Van Nostrand Reinhold Co. Inc, New York, 1983, pp. 212-235.

I. Fábián, "The reactions of transition metal ions with chlorine (III)", Coordination Chemistry Reviews, 2001, vol. 216-217, pp. 449-472.

Shibuya, "Development of Varsatile Oxidation Systems Based on the Design of Oxoammonium Salts", Yakugaku Zasshi, 2012, vol. 132, No. 10, pp. 1131-1143—Abstract on p. 1131.

Yamada, Y. et al., "Acetate Induced Enhancement of Photocatalytic Hydrogen Peroxide Production from Oxalic Acid and Dioxygen", The Journal of Physical Chemistry A, 2013, vol. 117, pp. 3751-3760.

Fukuzumi, S. et al., "Quantitative Evaluation of Lewis Acidity of Metal Ions Derived from the g Values of ESR Spectra of Superoxide: Metal Ion Complexes in Relation to the Promoting Effects in Electron Transfer Reactions", Chemistry A European Journal, 2000, vol. 6, No. 24, pp. 4532-4535, Results and Discussion.

Masere, J. et al., "Gas-Free Initiators for High-Temperature Free-Radical Polymerization", Journal of Polymer Science Part A, 2000, vol. 38, No. 21, pp. 3984-3990, Experimental, Results and Discussion.

Office Action of the corresponding Japanese Patent Application (No. 2015-248067) dated Nov. 16, 2016—with a machine translation.

Ohkubo et al., JOC Article "Quantitative Evaluation of Lewis Acidity of Metal Ions with Different Ligands and Counterions in Relation to the Promoting Effects of Lewis Acids on Electron Transfer Reduction of Oxygen", Journal of Organic Chemisry, 2003, vol. 68, No. 12, pp. 4720-4726.

Ohkubo et al., "Simultaneous productions of p-tolualdehyde and hydrogen peroxide in photocatalytic oxygenation of p-xylene and reduction of oxygen with 9-mesityl-10-methylacridinium ion derivatives", Chemical Communications, 2010, vol. 46, pp. 601-603.

Kotani et al., "Formation of a long-lived electron-transfer state of a naphthalene-quinolinium ion dyad and the π-dimer radical cation"., Faraday Discussions, 2012, vol. 155, pp. 89-102.

Office Action of the corresponding Japanese Patent Application (No. 2015-248067) dated Jun. 14, 2017—with a machine translation.

Bal Raj Deshwal et al., "Reaction Kinetics of Decomposition of Acidic Sodium Chlorite", The Canadian Journal of Chemical Engineering, 2004, vol. 82, pp. 619-623.

Office Action of the corresponding Japanese Patent Application (No. 2015-248068) dated Nov. 16, 2016—with a machine translation.

Office Action of the corresponding Japanese Patent Application (No. 2015-248068) dated May 24, 2017—with a machine translation.

Tsudaka et al., "Photocatalyst Oxicidation of Metal Complex by Dioxygen with Organic Electron-Donor-Acceptor Linked Molecules", Abstract of The Chemical Society of Japan 94th Proceedings of the Spring Annual Meeting IV, Mar. 12, 2014, vol. 94, No. 4, p. 1105—Abstract on p. 1105

Doi et al., "Formation of Long-Lived Electron Transfer States in Donor-Acceptor Linked Cations into Nano-Sized Mesoporous Silica with Spherical Shape and the Photocatalyic Function", Abstract of the Chemical Society of Japan 90th Proceedings of the Spring Annual Meeting IV, Mar. 12, 2010, vol. 90, No. 4, p. 1135—Abstract on p. 1135.

Ohkubo et al., "Quantitative Evaluation of Lewis Acidity of Orgonotion Compunds and Catalysis of Electron transfer" Abstract of The Chemical Society of Japan 79th Proceedings of the Spring Annual Meeting II, 2011, vol. 79, No. 2, p. 756—cited in the JP Office Action dated May 24, 2017 in corresponding JP Patent Application No. 2015-248068 see the translation of the JP Office Action for relevance.

Office Action of the corresponding Japanese Patent Application (No. 2015-248069) dated Nov. 21, 2016—with a machine translation.

Office Action of the corresponding Japanese Patent Application (No. 2015-248069) dated May 16, 2017—with a machine translation.

Partial Supplementary European Search Report of the corresponding European Patent Application No. 16875771.4 dated Jul. 24, 2019, 15 pages.

Turovskij et al., "Supramolecular Reaction of Lauroyl Peroxide with Tetraalkylammonium Bromides", Oxidation Communications, 2010, vol. 33, No. 3, pp. 485-501.

Office Action of the corresponding Chinese Patent Application No. 201680074780.1 dated Aug. 20, 2020, 12 pages with translation.

\* cited by examiner (a)

(b)

Activation of electron transfer reaction between cobalt porphyrin and oxygen

[CoTPP] = 9.0 x 10⁻⁶ M
[Bzt⁺Cl⁻] = 30 mM
[O₂] = 13 mM

Ohkubo, K.; Fukuzumi, S. *Chem. Eur. J.* 2000, *6*, 4532

RADICAL GENERATING CATALYST, METHOD FOR PRODUCING RADICAL, METHOD FOR PRODUCING OXIDATION REACTION PRODUCT, DRUG, AND DRUG FOR AGRICULTURE AND LIVESTOCK

TECHNICAL FIELD

The present invention relates to a radical generating catalyst, a method for producing radicals, a method for producing an oxidation reaction product, a drug, and a drug for use in agriculture and livestock industry.

BACKGROUND ART

Background Art of First and Second Aspects of Invention

On the other hand, owing to its high reactivity, a radical is an important chemical species that is used widely. For example, sodium chlorite ($NaClO_2$) is a non-toxic inexpensive oxidizing reagent and has been used as a precursor of a chlorine dioxide radical ($ClO_2$) (Non Patent Literatures 1 to 4).

Background Art of Third Aspect of Invention

Diseases caused by infection with bacteria and the like have long been problems all over the world. At present, in order to avoid infection, bacteria are removed by, for example, spraying a bactericide on the bacteria. Various types of bactericides are used today, and example thereof include chlorine dioxide. Chlorine dioxide is used in hospitals, nursing facilities, etc.

Chlorine dioxide used as a bactericide is disclosed in Patent Literature 1, for example. Patent Literature 1 describes that the bactericide is produced by providing an aqueous solution containing a chlorite such as sodium chlorite and adjusting the pH of the aqueous solution by adding a buffer thereto to stabilize the aqueous solution.

Examples of bactericides used widely in Japan include ethanol for disinfection and hypochlorous acid. For example, Patent Literature 2 describes sterilizing water in swimming pools with hypochlorous acid.

Background Art of Fourth Aspect of Invention

When agricultural crops are infected with bacteria or the like, inhibition of the growth of the agricultural crops, reduction of the yield of the agricultural crops, etc. are caused. Thus, infection with bacteria or the like is prevented or treated by spreading a bactericide. Also, when bacteria and the like grow in the excrement of industrial animals, a foul odor is caused. Thus, deodorization or the like is performed by spreading a bactericide.

As a bactericide for preventing the infection and growth of bacteria and the like, chlorine dioxide and hypochlorous acid are used, for example. For example, Patent Literature 1 describes that a bactericide is produced by providing an aqueous solution containing a chlorite such as sodium chlorite and adjusting the pH of the aqueous solution by adding a buffer thereto to stabilize the aqueous solution. Patent Literature 2 describes that hypochlorous acid can be used for sterilization.

CITATION LIST

Patent Literatures

Patent Literature 1: JP 2009-100850 A
Patent Literature 2: JP 2014-091063 A

Non Patent Literatures

[Non Patent Literature 1] H. Dodgen and H. Taube, J. Am. Chem. Soc., 1949, 71, 2501-2504.
[Non Patent Literature 2] J. K. Leigh, J. Rajput, and D. E. Richardson, Inorg. Chem., 2014, 53, 6715-6727.
[Non Patent Literature 3] C. L. Latshaw, Tappi J., 1994, 163-166.
[Non Patent Literature 4] (a) J. J. Leddy, in Riegel's Handbook of Industrial Chemistry, 8th edn. Ed., J. A. Kent, Van Nostrand Reinhold Co. Inc, New York, 1983, pp. 212-235; (b) I. Fabian, Coord. Chem. Rev., 2001, 216-217, 449-472.

SUMMARY OF INVENTION

Technical Problem

Technical Problem to be Solved by First and Second Aspects of Invention

However, high energy is generally required for generating radicals. Thus, heating or the like to raise the temperature is required, which causes problems in cost and reaction control. On this account, it is an object of the first aspect of the present invention to provide a radical generating catalyst that can generate (produce) radicals under mild conditions, a method for producing radicals using the radical generating catalyst, and a method for producing an oxidation reaction product using the radical production method. Further, it is an object of the second aspect of the present invention to provide a radical production method that can generate (produce) radicals under mild conditions and a method for producing an oxidation reaction product using the radical production method.

Technical Problem to be Solved by Third Aspect of Invention

Chlorine dioxide has a very high sterilizing and deodorizing ability. However, it is a highly explosive gas, and in Japan, accidental explosions of chlorine dioxide have been reported several times. An aqueous solution of chlorine dioxide also is not preferable, because the chlorine dioxide is decomposed easily owing to change in conditions such as the pH or the temperature of the aqueous solution, thereby causing an unpleasant odor, and, in some cases, adversely affecting the human body. Accordingly, bactericides using chlorine dioxide have a problem in that they lack safety and storage stability.

Ethanol exhibits a low sterilizing effect, because it volatilizes immediately after being sprayed on hands or the like for sterilization.

Further, hypochlorous acid is decomposed immediately, so that the hypochlorous acid has a problem in that, while it has a temporary sterilizing effect, it cannot exhibit a sterilizing effect stably.

With the foregoing in mind, it is an object of the third aspect of the present invention to provide a drug that is highly safe and has a high sterilizing effect.

Technical Problem to be Solved by Fourth Aspect of Invention

While chlorine dioxide has a very high sterilizing and deodorizing ability, it is highly explosive. Also, a chlorine dioxide aqueous solution is decomposed easily owing to the change in pH, temperature, or the like of the aqueous solution. Thus, bactericides using chlorine dioxide have a problem in that they lack safety and storage stability. Further, hypochlorous acid is decomposed immediately, so that the hypochlorous acid has a problem in that it only has a temporary sterilizing effect.

With the foregoing in mind, it is an object of the fourth aspect of the present invention to provide a drug for use in agriculture and livestock industry, that is highly safe and has a high sterilizing effect, and a method for producing the same.

Solution to Problem

Solution to Problem by First Aspect of Invention

In order to achieve the above object, the first aspect of the present invention provides a first radical generating catalyst including: ammonium and/or a salt thereof. The first aspect of the present invention also provides a second radical generating catalyst including: an organic compound having Lewis acidic properties and/or Brønsted acidic properties. Hereinafter, the first radical generating catalyst and the second radical generating catalyst according to the first aspect of the present invention may be referred to collectively as "the radical generating catalyst of the present invention".

In order to achieve the above object, the first aspect of the present invention also provides a method for producing a radical, including: a mixing step of mixing the radical generating catalyst of the present invention with a radical source.

The first aspect of the present invention also provides a method for producing an oxidation reaction product by oxidizing a substance to be oxidized, including: a radical production step of producing a radical by the radical production method according to the first aspect of the present invention; and an oxidation reaction step of reacting the substance to be oxidized with an oxidizing agent by action of the radical, thereby generating the oxidation reaction product.

Solution to Problem by Second Aspect of Invention

In order to achieve the above object, the second aspect of the present invention provides a method for producing a radical, including: a mixing step of mixing a Lewis acid and/or a Brønsted acid with a radical source.

The second aspect of the present invention also provides a method for producing an oxidation reaction product by oxidizing a substance to be oxidized, including: a radical production step of producing a radical by the radical production method according to the second aspect of the present invention; and an oxidation reaction step of reacting the substance to be oxidized with an oxidizing agent by action of the radical, thereby generating the oxidation reaction product.

Solution to Problem by Third Aspect of Invention

In order to achieve the above object, the third aspect of the present invention provides a drug containing: a radical generating catalyst; and a radical source, wherein the radical generating catalyst includes either or both of: ammonium and/or a salt thereof, and a substance having Lewis acidic properties and/or Brønsted acidic properties.

Solution to Problem by Fourth Aspect of Invention

In order to achieve the above object, the fourth aspect of the present invention provides a drug for use in agriculture and livestock industry, containing: a radical generating catalyst; and a radical source, wherein the radical generating catalyst includes either or both of: ammonium and/or a salt thereof; and a substance having Lewis acidic properties and/or Brønsted acidic properties.

Advantageous Effects of Invention

Advantageous Effects of First Aspect of Invention

According to the radical generating catalyst, radical-generating agent, and radical production method of the first aspect of the present invention, it is possible to generate (produce) radicals under mild conditions. While the radical generating catalyst, radical-generating agent, and radical production method of the first aspect of the present invention can be used in, for example, the oxidation reaction product production method of the first aspect of the present invention, the use thereof is not limited thereto, and they are applicable to a wide variety of uses.

Advantageous Effects of Second Aspect of Invention

According to the radical production method of the second aspect of the present invention, it is possible to generate (produce) radicals under mild conditions. While the radical production method of the second aspect of the present invention can be used in, for example, the oxidation reaction product production method of the second aspect of the present invention, the use thereof is not limited thereto, and it is applicable to a wide variety of uses.

Advantageous Effects of Third Aspect of Invention

According to the third aspect of the present invention, it is possible to provide a drug that is highly safe and has a high sterilizing effect.

Advantageous Effects of Fourth Aspect of Invention

According to the fourth aspect of the present invention, it is possible to provide a drug that is highly safe and has a high sterilizing effect.

BRIEF DESCRIPTION OF DRAWINGS

In FIG. 4, (a) shows a spectrum of a MeCN solution that contains $NaClO_2$ (0.10 mM) at 353 K after 1-hour reflux; (b) shows a spectrum of a MeCN solution that contains $NaClO_2$ (0.10 mM) and $CF_3COOH$ (10 mM); and (c) shows a spectrum of a MeCN solution that contains $NaClO_2$ (0.10 mM) and $Sc(OTf)_3$ (10 mM).

In FIG. 5, (a) shows the result obtained regarding $ClO_2$; (b) shows the result obtained regarding $H^+ClO_2$; and (c) shows the result obtained regarding $Sc^{3+} ClO_2$.

In FIG. 10, (a) shows a spin distribution of $H+ClO_2.$; and (b) shows a spin distribution of $Sc^{3+}+ClO_2$.

DESCRIPTION OF EMBODIMENTS

Figure 1:
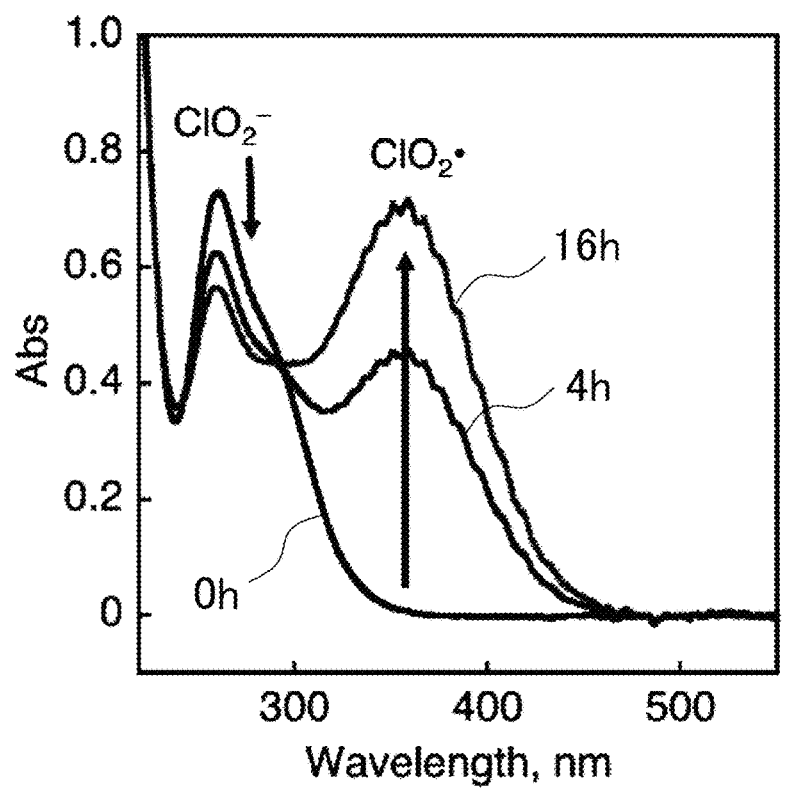
FIG. 1 shows an ultraviolet-visible absorption spectrum of $NaClO_2$ (5.0 mM) collected 0, 4, and 16 hours after mixing with $Sc(OTf)_3$ (10 mM) in an aqueous solution at 298 K.

The present invention will be described more specifically below with reference to illustrative examples. It is to be noted, however, that the present invention is by no means limited by the following descriptions.

Description of Embodiments of First Aspect of Invention

First, embodiments of the first aspect of the present invention will be described. It is to be noted, however, that the first aspect of the present invention is not limited by the following descriptions.

[1. Radical-Generating Agent]

As described above, the radical generating catalyst according to the first aspect of the present invention may be a radical generating catalyst including ammonium and/or a salt thereof (the first radical generating catalyst according to the first aspect of the present invention). Alternatively, the radical generating catalyst according to the first aspect of the present invention may be a radical generating catalyst including an organic compound having Lewis acidic properties and/or Brønsted acidic properties (the second radical generating catalyst according to the first aspect of the present invention).

The inventors of the present invention found out through research that ammonium (in particular, organic ammonium) serves as a radical generating catalyst. As a result of further research, the inventors of the present invention further found out that ammonium serving as a radical generating catalyst may have properties as a Lewis acid. That is, while the reason why the ammonium serves as a radical generating catalyst is not clear, it is presumably because the ammonium has a function as a Lewis acid. As a result of still further research, the inventors of the present invention discovered a radical generating catalyst including an organic compound having Lewis acidic properties and/or Brønsted acidic properties. In the first aspect of the present invention, the "Lewis acid" refers to a substance that acts as a Lewis acid with respect to the radical source, for example.

The Lewis acidity of the radical generating catalyst according to the first aspect of the present invention is, for example, 0.4 eV or more. The upper limit of the Lewis acidity is not particularly limited, and is, for example, 20 eV or less. It is to be noted that the Lewis acidity can be measured, for example, by the method described in Ohkubo, K.; Fukuzumi, S. Chem. Eur. J., 2000, 6, 4532, J. Am. Chem. Soc. 2002, 124, 10270-10271 or the method described in J. Org. Chem. 2003, 68, 4720-4726. Specifically, the Lewis acidity can be measured by the following method.

(Measurement Method of Lewis Acidity)

As to acetonitrile (MeCN) that contains cobalt tetraphenylporphyrin, saturated $O_2$, and an object whose Lewis acidity is to be measured (e.g., a cation of a metal or the like, represented by $M^{n+}$ in the following chemical reaction formula (1a)) in the following chemical reaction formula (1a), the change of the ultraviolet-visible absorption spectrum is measured at room temperature. On the basis of the obtained reaction rate constant ($k_{cat}$), the ΔE value (eV), which is an indicator of the Lewis acidity, can be calculated. The higher the $k_{cat}$, the stronger the Lewis acidity. Furthermore, the Lewis acidity of an organic compound can be estimated from the energy level of the lowest unoccupied molecular orbital (LUMO) calculated by the quantum chemical calculation. The higher the value at the positive side, the stronger the Lewis acidity.

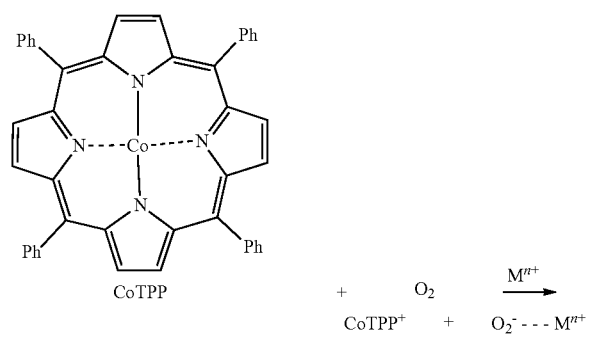

(1a)

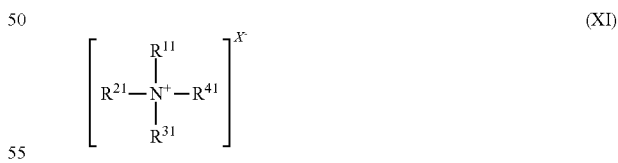

Examples of the rate constant of reaction between CoTPP and oxygen in the presence of a Lewis acid, which is an indicator of the Lewis acidity measured (calculated) by the above-described measurement method, are shown below. In the following table, the numerical value expressed in the unit "$k_{cat}$, $M^{-2}S^{-1}$" is a rate constant of reaction between CoTPP and oxygen in the presence of a Lewis acid. The numerical value expressed in the unit "LUMO, eV" is the energy level of LUMO. The "benzetonium chloride" means benzethonium chloride, "benzalkonium chloride" means benzalkonium chloride, "tetramethylammonium hexafluorophosphate" means tetramethylammonium hexafluorophosphate, "tetrabutylammonium hexafluorophosphate, and "ammonium hexafluorophosphate" means ammonium hexafluorophosphate (Note from translator: in the table in Japanese).

TABLE tpp

| | LUMO, eV | $k_{cat}$, $M^{-2}$ $s^{-1}$ |
|---|---|---|
| benzetonium chloride | −4.12 | 0.24 |
| benzalkonium chloride | −4.02 | 0.18 |
| tetramethylammonium hexafluorophosphate | −3.58 | >0.1 |
| tetrabutylammonium hexafluorophosphate | −2.07 | >0.1 |
| ammonium hexafluorophosphate | −5.73 | 20 |

In the radical generating catalyst of the first aspect of the present invention, the ammonium may be quaternary ammonium, or may be tertiary ammonium, secondary ammonium, primary ammonium, or ammonium, for example.

In the radical generating catalyst of the first aspect of the present invention, the ammonium (the first radical generating catalyst according to the first aspect of the present invention) or the organic compound having Lewis acidic properties and/or Brønsted acidic properties (the second radical generating catalyst according to the first aspect of the present invention) may be, for example, a cationic surfactant, which may be a quaternary ammonium-type cationic surfactant. Examples of the quaternary ammonium-type cationic surfactant include benzalkonium chloride, benzethonium chloride, cetylpyridinium chloride, hexadecyltrimethylammonium bromide, dequalinium chloride, edrophonium, didecyldimethylammonium chloride, tetramethylammonium chloride, tetrabutylammonium chloride, benzyltriethylammonium chloride, oxytropium, carbachol, glycopyrronium, safranin, sinapine, tetraethylammonium bromide, hexadecyltrimethylammonium bromide, suxamethonium, sphingomyelin, denatonium, trigonelline, neostigmine, paraquat, pyridostigmine, phellodendrine, pralidoxime methiodide, betaine, betanin, bethanechol, betalain, lecithin, and cholines (e.g., choline chlorides [such as benzoyl choline chloride and a lauroylcholine chloride hydrate], phosphocholine, acetylcholine, choline, dipalmitoylphosphatidylcholine, and choline bitartrate). It is to be noted, however, that, in the radical production method of the first aspect of the present invention, the quaternary ammonium is not limited to a surfactant.

In the radical generating catalyst of the first aspect of the present invention, the ammonium may be ammonium represented by the following chemical formula (XI), for example.

$$\begin{bmatrix} & R^{11} & \\ R^{21} & \!\!-\!\!N^+\!\!-\!\! & R^{41} \\ & R^{31} & \end{bmatrix}^X \quad (XI)$$

In the chemical formula (XI), $R^{11}$, $R^{21}$, $R^{31}$, and $R^{41}$ are each a hydrogen atom or an alkyl group (e.g., a straight-chain or branched alkyl group having 1 to 40 carbon atoms) and may each include an ether bond, a ketone (carbonyl group), an ester bond, or an amide bond, or an aromatic ring. $R^{11}$, $R^{21}$, $R^{31}$, and $R^{41}$ may be the same or different from each other. $X^-$ is an anion.

The ammonium represented by the chemical formula (XI) may be ammonium represented by the following chemical formula (XII), for example.

In the chemical formula (XII), $R^{111}$ is an alkyl group having 5 to 40 carbon atoms and may comprise an ether bond, a ketone (carbonyl group), an ester bond, or an amide bond, or an aromatic ring, and $R^{21}$ and $X^-$ are the same as those in the chemical formula (XI).

In the chemical formula (XII), $R^{21}$ may be a methyl group or a benzyl group, for example. In the benzyl group, one or more hydrogen atoms on the benzene ring may or may not be substituted with any substituent. The substituent may be, for example, an alkyl group, an unsaturated aliphatic hydrocarbon group, an aryl group, a heteroaryl group, a halogen, a hydroxy group (—OH), a mercapto group (—SH), or an alkylthio group (—SR, where R is an alkyl group).

The ammonium represented by the chemical formula (XII) may be ammonium represented by the following chemical formula (XIII), for example.

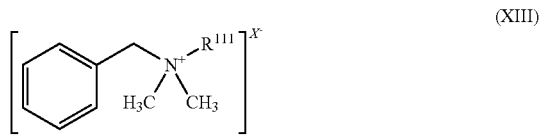

In the chemical formula (XIII), $R^1$ and $X^-$ are the same as those in the chemical formula (XII).

The ammonium represented by the chemical formula (XI) may be, for example, at least one selected from the group consisting of benzethonium chloride, benzalkonium chloride, hexadecyltrimethylammonium chloride, tetramethylammonium chloride, ammonium chloride, and tetrabutylammonium chloride. It is particularly preferable that the ammonium represented by the chemical formula (XII) is benzethonium chloride.

Benzethonium chloride ($Bzn^+Cl^-$) can be represented by the following chemical formula, for example. Benzalkonium chloride can be, for example, a compound represented by the chemical formula (XIII) where $R^1$ is an alkyl group having 8 to 18 carbon atoms and $X^-$ is a chloride ion.

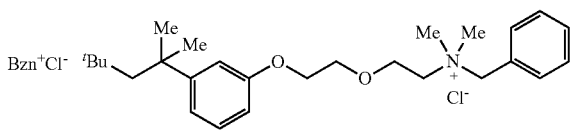

In the chemical formulae (XI), (XII), and (XIII), $X^-$ may be any anion and is not particularly limited. $X^-$ is not limited to a monovalent anion, and may be an anion with any valence, such as a divalent anion or a trivalent anion. When the anion is an anion with a plurality of electric charges, such as a divalent anion or a trivalent anion, the number of molecules of the ammonium (monovalent) in each of the chemical formulae (XI), (XII), and (XIII) is determined by, for example, [the number of molecules of the anion×the valence of the anion] (e.g., when the anion is divalent, the number of molecules of the ammonium (monovalent) is twice the number of molecules of the anion). $X^-$ may be, for example, a halogen ion (a fluoride ion, a chloride ion, a bromide ion, or an iodide ion), an acetate ion, a nitrate ion, or a sulfate ion.

In the first aspect of the present invention, the ammonium may include a plurality of ammonium structures ($N^+$) in one molecule. Further, the ammonium may form a dimer, trimer, or the like by association of a plurality of molecules through a π electron interaction, for example.

In the radical-generating agent according to the first aspect of the present invention, the acid dissociation constant $pK_a$ of the Brønsted acid is, for example, 5 or more. The upper limit of the $pK_a$ is not particularly limited and is, for example, 50 or less.

[2. Radical Production Method]

Next, the radical production method according to the first aspect of the present invention will be described.

As described above, the radical production method of the first aspect of the present invention is characterized in that it includes a mixing step of mixing the radical generating catalyst of the first aspect of the present invention with a radical source. The mixture may or may not further contain a substance(s) other than the radical generating catalyst of the first aspect of the present invention and the radical source. For example, in the mixing step, it is preferable to further mix a solvent from the viewpoint of reactivity and the like. In the first aspect of the present invention, the "solvent" may or may not dissolve the radical generating catalyst of the first aspect of the present invention, the radical source, and the like. For example, after the mixing step, the radical generating catalyst of the first aspect of the present invention and the radical source may each be in a state of being dissolved in the solvent, or may each be in a state of being dispersed or precipitated in the solvent.

The radical production method of the first aspect of the present invention includes, for example, after the mixing step, a radical production step of producing radicals through a reaction in the obtained mixture. As described above, the mixture may be in the form of a solution, a suspension, or a colloid, for example. From the viewpoint of reactivity, it is preferable that the mixture is in the form of a solution or a colloid, for example. In the radical production step, the mixture may be merely allowed to stand still at room temperature, or may be subjected to heating, light irradiation, or the like when necessary, for example. The reaction temperature and the reaction time in the radical production step are not particularly limited, and can be set as appropriate depending on the type of the reactant (raw material), the type of a desired product, etc., for example. When the mixture is irradiated with light, the wavelength of the light is not particularly limited, and can be set as appropriate depending on the absorption band of the reactant (raw material), etc., for example. The reaction time and the reaction temperature also can be adjusted by, for example, adjusting the concentrations of the radical generating catalyst of the first aspect of the present invention and the radical source in the mixture. The reaction time can be shortened by setting the concentrations higher, for example. It is to be noted, however, that the first aspect of the present invention is not limited by this description.

The concentration of the radical generating catalyst of the first aspect of the present invention is not particularly limited. For example, the molar concentration of the reactant relative to the solvent is not particularly limited, and can be set as appropriate depending on the type of the reactant (raw material), the type of a desired product, etc., for example. The solvent is not particularly limited, and may be either water or an organic solvent, for example. The organic solvent may be, for example: a halogenated solvent such as methylene chloride, chloroform, or carbon tetrachloride; ketone such as acetone; a nitrile solvent such as acetonitrile; an alcohol solvent such as methanol or ethanol; an acetic acid solvent; or a sulfuric acid solvent. Only one type of solvent may be used, or two or more types of solvents may be used in combination, for example. The acetic acid solvent and sulfuric acid solvent may be, for example, solvents obtained by dissolving acetic acid and sulfuric acid in water, respectively. They are solvents and, at the same time, also serve as a Lewis acid or a Brønsted acid, for example. The type of the solvent may be selected as appropriate depending on the solubility of the solutes (e.g., the radical generating catalyst of the first aspect of the present invention, the radical source, and the like), etc., for example.

In the radical production method of the first aspect of the present invention, the reaction may be performed by heating the mixture, as described above. Also, it is possible to produce radicals by performing the reaction by merely irradiating the mixture with light without heating or by merely allowing the mixture to stand still at room temperature without heating or light irradiation. The definition of the "room temperature" is not particularly limited, and is from 5° C. to 35° C., for example. Since the radical production method of the first aspect of the present invention can be performed without heating, the cost for the heating with an electric furnace or the like is not necessary, which allows a drastic reduction in the cost for producing radicals, for example. Besides, since the radical production method of the first aspect of the present invention can be performed without heating, an unexpected runaway reaction caused by a radical chain reaction and accumulation of peroxides are prevented, which greatly improves the safety of the reaction and allows still further reduction in cost, for example. It is to be noted, however, that these descriptions are merely illustrative, and do not limit the first aspect of the present invention by any means.

The radical production method of the first aspect of the present invention may further include, for example, a light irradiation step of irradiating the mixture obtained in the mixing step with light. Then, as described above, radicals may be produced through a reaction caused by the light irradiation. The wavelength of the irradiation light is as described above, for example. A light source is not particularly limited. For example, by using visible light contained in natural light such as sunlight, excitation can be performed easily. Also, for example, instead of or in addition to the natural light, a light source such as a xenon lamp, a halogen lamp, a fluorescent lamp, or a mercury lamp may be used when necessary or may not be used. Further, a filter that cuts wavelengths other than a necessary wavelength may be used when necessary or may not be used.

In the radical production method of the first aspect of the present invention, the radical source may include, for example, at least one selected from the group consisting of halogen ions, hypohalite ions, halite ions, halate ions, and perhalate ions. Particularly preferably, the radical source includes a chlorite ion, for example. The radical source may include, for example, an oxoacid or a salt thereof (e.g., a halogen oxoacid or a salt thereof). Examples of the oxoacid include boric acid, carbonic acid, orthocarbonic acid, carboxylic acid, silicic acid, nitrous acid, nitric acid, phosphorous acid, phosphoric acid, arsenic acid, sulfurous acid, sulfuric acid, sulfonic acid, sulfinic acid, chromic acid, dichromic acid, and permanganic acid. Examples of the halogen oxoacid include: chlorine oxoacids such as hypochlorous acid, chlorous acid, chloric acid, and perchloric acid; bromine oxoacids such as hypobromous acid, bromous acid, bromic acid, and perbromic acid; and iodine oxoacids such as hypoiodous acid, iodous acid, iodic acid, and periodic acid.

The radical source may be selected as appropriate depending on the use thereof, with consideration given to the intensity of reactivity of a radical species, etc., for example. For example, hypochlorous acid exhibiting high reactivity or chlorous acid exhibiting somewhat lower reactivity than the hypochlorous acid and allowing a reaction to be controlled more easily may be used as appropriate depending on the intended use.

In the radical production method of the first aspect of the present invention, the radical source may include an electron donor-acceptor linked molecule, for example. The electron donor-acceptor linked molecule is not particularly limited. For example, the electron donor-acceptor linked molecule may be such that an electron donor moiety is composed of one or more electron donor groups and an electron acceptor moiety is composed of one or more aromatic cations. In this case, the aromatic cation may be either a monocyclic ring or a condensed ring, and the aromatic ring may or may not include a heteroatom and may or may not have a substituent other than the electron donor group. Furthermore, an aromatic ring that forms the aromatic cation may be, for example, any of a 5- to 26-membered ring, although the number of atoms constituting the ring is not particularly limited.

The aromatic ring that forms the aromatic cation preferably is at least one selected from the group consisting of a pyrrolinium ring, a pyridinium ring, a quinolinium ring, an isoquinolinium ring, an acridinium ring, a 3,4-benzoquinolinium ring, a 5,6-benzoquinolinium ring, a 6,7-benzoquinolinium ring, a 7,8-benzoquinolinium ring, a 3,4-benzoisoquinolinium ring, a 5,6-benzoisoquinolinium ring, a 6,7-benzoisoquinolinium ring, a 7,8-benzoisoquinolinium ring, and rings obtained by substitution of at least one carbon atom of these rings with a heteroatom. For example, when the aromatic ring is a macrocyclic (having many xt electrons) aromatic cation such as an acridinium ring, a benzoquinolinium ring, or a benzoisoquinolinium ring, for example, visible light excitation becomes possible if the absorption band shifts toward the longer wavelength side so as to be in the visible region.

The electron donor group preferably is at least one selected from the group consisting of a hydrogen atom, alkyl groups, and aromatic rings. In this case, the aromatic ring further may have one or more substituents on the ring, and when a plurality of substituents are present, they may be the same or different from each other. When a plurality of electron donor groups are present, they may be the same or different from each other. Furthermore, in the electron donor group in this case, it is more preferable that the alkyl group is a straight-chain or branched alkyl group having 1 to 6 carbon atoms. Furthermore, in the electron donor group, it is more preferable that the aromatic ring is at least one selected from the group consisting of a benzene ring, a naphthalene ring, an anthracene ring, a phenanthrene ring, a pyridine ring, a thiophene ring, and a pyrene ring. In the electron donor group, it is more preferable that the substituent on the aromatic ring is at least one selected from the group consisting of alkyl groups, alkoxy groups, primary to tertiary amines, carboxylic acids, and carboxylate esters. In Ar, it is more preferable that the substituent on the aromatic ring is at least one selected from the group consisting of straight-chain or branched alkyl groups having 1 to 6 carbon atoms, straight-chain or branched alkoxy groups having 1 to 6 carbon atoms, primary to tertiary amines, carboxylic acids, and carboxylate esters. In the substituent on the aromatic ring, a "carboxylic acid" refers to a carboxyl group or a group having a carboxyl group added to its end (e.g., a carboxyalkyl group), and a "carboxylate ester" refers to a carboxylate ester group such as an alkoxycarbonyl group or a phenoxycarbonyl group, or an acyloxy group. An alkyl group in the carboxyalkyl group preferably is a straight-chain or branched alkyl group having 1 to 6 carbon atoms, for example. An alkoxy group in the alkoxycarbonyl group preferably is a straight-chain or branched alkoxy group having 1 to 6 carbon atoms, for example.

It is still more preferable that the electron donor group is at least one selected from the group consisting of a phenyl group, an o-tolyl group, an m-tolyl group, a p-tolyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,3,4-trimethylphenyl group, a 2,3,5-trimethylphenyl group, a 2,3,6-trimethylphenyl group, a mesityl group (2,4,6-trimethylphenyl group), and a 3,4,5-trimethylphenyl group. Among these, a mesityl group is particularly preferable from the viewpoint of the lifetime of the electron-transfer state (charge-separated state) and the like. Although the reasons why a mesityl group can bring about a particularly excellent effect is not clear, they are speculated to be as follows, for example: two methyl groups are present in the ortho position, so that the benzene rings of the mesityl groups easily cross at right angles to the aromatic ring of the aromatic cation; and hyperconjugation does not occur very often inside the mesityl group. This, however, merely is an example of a presumable mechanism, and does not limit the first aspect of the present invention by any means.

The electron donor-acceptor linked molecule preferably is at least one selected from the group consisting of: nitrogen-containing aromatic cation derivatives represented by the following formulae (A-1) to (A-8); quinolinium ion derivatives represented by the following formula (I); stereoisomers and tautomers thereof; and salts thereof, from the viewpoints of the lifetime, oxidizing power, reducing power, and the like of the electron-transfer state (charge-separated state).

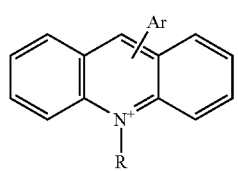

(A-1)

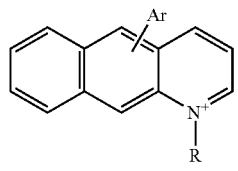

(A-2)

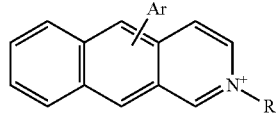

(A-3)

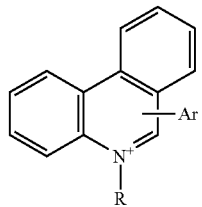

(A-4)

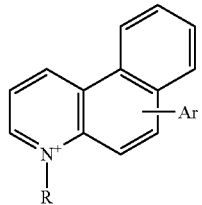

(A-5)

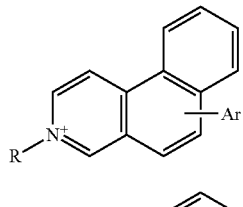

(A-6)

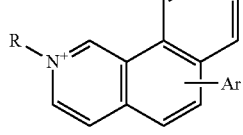

(A-7)

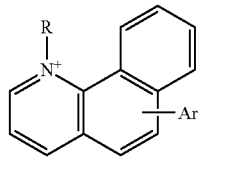

(A-8)

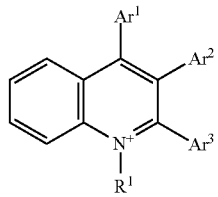

(I)

In the formulae (A-1) to (A-8), R is a hydrogen atom or any substituent, Ar is the electron donor group, and the number of Ars may be one or more, and when a plurality of Ars are present, they may be the same or different from each other, and the nitrogen-containing aromatic ring that forms a nitrogen-containing aromatic cation may or may not have at least one substituent other than R and Ar. In the formula (I), $R^1$ is a hydrogen atom or any substituent, $Ar^1$ to $Ar^3$ are each a hydrogen atom or the electron donor group and may be the same or different from each other, and at least one of $Ar^1$ to $Ar^3$ is the electron donor group.

In the formulae (A-1) to (A-8), R preferably is a hydrogen atom, an alkyl group, a benzyl group, a carboxyalkyl group (an alkyl group with a carboxyl group added to its end), an aminoalkyl group (an alkyl group having an amino group added to its end), or a polyether chain. More preferably, R is a hydrogen atom, a straight-chain or branched alkyl group having 1 to 6 carbon atoms, a benzyl group, a straight-chain or branched alkyl group having 1 to 6 carbon atoms with a carboxyl group added to its end, a straight-chain or branched alkyl group having 1 to 6 carbon atoms with an amino group added to its end, or a polyethylene glycol (PEG) chain. The PEG chain is an example of the polyether chain. The type of the polyether chain is not limited thereto, and the polyether chain may be of any type. In R, the degree of polymerization of the polyether chain is not particularly limited, and is, for example, 1 to 100, preferably 1 to 50, and more preferably 1 to 10. In the case where the polyether chain is a PEG chain, the degree of polymerization is not particularly limited, and is, for example, 1 to 100, preferably 1 to 50, and more preferably 1 to 10.

It is more preferable that the electron donor-acceptor linked molecule is at least one selected from the group consisting of 9-substituted acridinium ions represented by the following formula (A-9), tautomers thereof, and stereoisomers thereof.

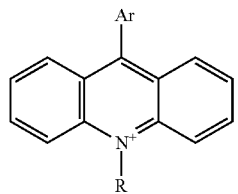

(A-9)

In the formula (A-9), R and Ar are the same as those in the formula (A-1).

Furthermore, it is particularly preferable that the electron donor-acceptor linked molecule is a 9-mesityl-10-methylacridinium ion represented by the following formula (A-10). By photoexcitation of this 9-mesityl-10-methylacridinium ion, it is possible to generate a long-lived electron-transfer state (charge-separated state) having a high oxidizing power and a high reducing power. As excitation light for the photoexcitation, it is possible to use visible light, for example.

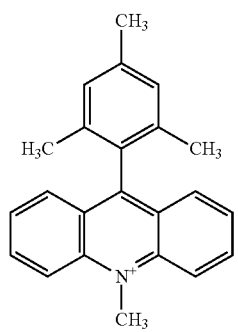

(A-10)

Examples of the 9-substituted acridinium ion represented by the formula (A-9) further include compounds (A-101) to (A-116) shown in the following table, in addition to the one represented by the above formula (A-10).

TABLE 1

| Compound No. | Substituent | |
|---|---|---|
| | R | Ar |
| (A-101) | methyl group | phenyl group |
| (A-102) | methyl group | o-tolyl group |
| (A-103) | methyl group | m-tolyl group |
| (A-104) | methyl group | p-tolyl group |
| (A-105) | methyl group | 2,3-dimethylphenyl group |
| (A-106) | methyl group | 2,4-dimethylphenyl group |
| (A-107) | methyl group | 2,5-dimethylphenyl group |
| (A-108) | methyl group | 2,6-dimethylphenyl group |
| (A-109) | methyl group | 3,4-dimethylphenyl group |
| (A-110) | methyl group | 3,5-dimethylphenyl group |
| (A-111) | methyl group | 2,3,4-trimethylphenyl group |
| (A-112) | methyl group | 2,3,5-trimethylphenyl group |
| (A-113) | methyl group | 2,3,6-trimethylphenyl group |
| (A-114) | methyl group | mesityl group (2,4,6-trimethylphenyl group) |
| (A-115) | methyl group | 3,4,5-trimethylphenyl group |
| (A-116) | methyl group | hydrogen atom |

In the quinolinium ion derivative represented by the formula (I), $R^1$ preferably is a hydrogen atom, an alkyl group, a benzyl group, a carboxyalkyl group (an alkyl group with a carboxyl group added to its end), an aminoalkyl group (an alkyl group having an amino group added to its end), or a polyether chain, for example. More preferably, $R^1$ is a hydrogen atom, a straight-chain or branched alkyl group having 1 to 6 carbon atoms, a benzyl group, a straight-chain or branched alkyl group having 1 to 6 carbon atoms with a carboxyl group added to its end, a straight-chain or branched alkyl group having 1 to 6 carbon atoms with an amino group added to its end, or a polyethylene glycol (PEG) chain, for example. The PEG chain is an example of the polyether chain. The type of the polyether chain is not limited thereto, and the polyether chain may be of any type. In $R^1$, the degree of polymerization of the polyether chain is not particularly limited, and is, for example, 1 to 100, preferably 1 to 50, and more preferably 1 to 10. In the case where the polyether chain is a PEG chain, the degree of polymerization is not particularly limited, and is, for example, 1 to 100, preferably 1 to 50, and more preferably 1 to 10. Furthermore, $Ar^1$ to $Ar^3$ preferably are each a hydrogen atom, an alkyl group, or an aromatic ring, for example, and the alkyl group more preferably is a straight-chain or branched alkyl group having 1 to 6 carbon atoms. In $Ar^1$ to $Ar^3$, the aromatic ring further may have one or more substituents on the ring, and when a plurality of substituents are present, they may be the same or different from each other.

In $Ar^1$ to $Ar^3$ in the formula (I), the aromatic ring more preferably is a benzene ring, a naphthalene ring, an anthracene ring, a phenanthrene ring, a pyridine ring, a thiophene ring, or a pyrene ring, for example. Furthermore, in $Ar^1$ to $Ar^3$, the substituent on the aromatic ring more preferably is an alkyl group, an alkoxy group, any one of primary to tertiary amines, a carboxylic acid, or a carboxylate ester. Still more preferably, the substituent on the aromatic ring is a straight-chain or branched alkyl group having 1 to 6 carbon atoms, a straight-chain or branched alkoxy group having 1 to 6 carbon atoms, any one of primary to tertiary amines, a carboxylic acid, or a carboxylate ester. The secondary amine is not particularly limited, and preferably is an alkylamino group, and more preferably is a straight-chain or branched alkylamino group having 1 to 6 carbon atoms, for example. The tertiary amine is not particularly limited, and preferably is a dialkylamino group, and more preferably is a dialkylamino group with a straight-chain or branched alkyl group having 1 to 6 carbon atoms, for example.

In the substituent on the aromatic ring in $Ar^1$ to $Ar^3$, a "carboxylic acid" refers to a carboxyl group or a group having a carboxyl group added to its end (e.g., a carboxyalkyl group), and a "carboxylate ester" refers to a carboxylate ester group such as an alkoxycarbonyl group or a phenoxycarbonyl group, or an acyloxy group. An alkyl group in the carboxyalkyl group preferably is a straight-chain or branched alkyl group having 1 to 6 carbon atoms, for example. An alkoxy group in the alkoxycarbonyl group preferably is a straight-chain or branched alkoxy group having 1 to 6 carbon atoms, for example.

Among the quinolinium ion derivatives represented by the formula (I), for example, quinolinium ion derivatives represented by the following formulae 1 to 5 are particularly preferable in terms of a long lifetime, a high oxidizing power, a high reducing power, and the like of the charge-separated state.

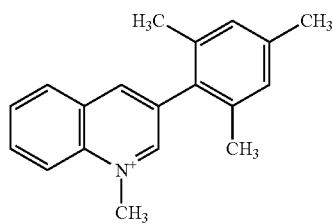

1

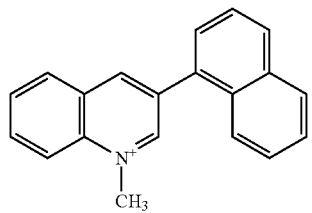

2

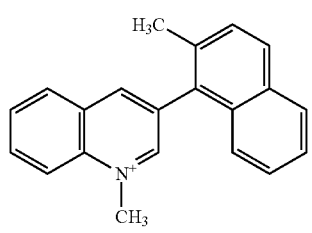

3

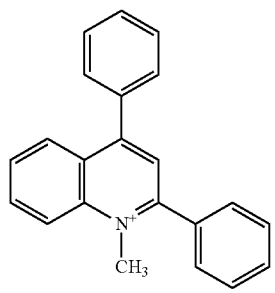

4

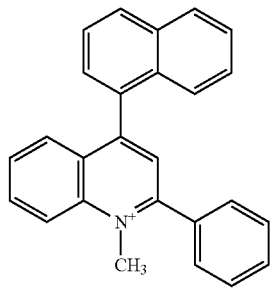

5

In addition to the above compounds 1 to 5, compounds 6 to 36 shown in Tables 1 and 2 below also are particularly preferable, for example. Tables 2 and 3 show the structures of the compounds 6 to 36 by indicating the combination of $R^1$ and $Ar^1$ to $Ar^3$ in the formula (I). Those skilled in the art can produce and use the compounds 6 to 36 easily according to the production and use of the compounds 1 to 5 with reference to examples to be described below, without undue trial and error, complicated and advanced experiments, etc.

TABLE 2

| Com- | Substituent | | | |
|---|---|---|---|---|
| pound No. | $R^1$ | $Ar^1$ | $Ar^2$ | $Ar^3$ |
| 6 | methyl group | hydrogen atom | phenyl group | hydrogen atom |
| 7 | methyl group | hydrogen atom | tolyl group | hydrogen atom |
| 8 | methyl group | hydrogen atom | xylyl group | hydrogen atom |
| 9 | methyl group | hydrogen atom | durenyl group | hydrogen atom |
| 10 | methyl group | hydrogen atom | phenyl group | hydrogen atom |
| 11 | methyl group | hydrogen atom | aminophenyl group | hydrogen atom |
| 12 | methyl group | hydrogen atom | methoxynaphthyl group | hydrogen atom |
| 13 | methyl group | hydrogen atom | anthryl group | hydrogen atom |
| 14 | methyl group | hydrogen atom | pyrenyl group | hydrogen atom |
| 15 | ethoxycarbonyl group | hydrogen atom | phenyl group | hydrogen atom |
| 16 | ethoxycarbonyl group | hydrogen atom | tolyl group | hydrogen atom |
| 17 | ethoxycarbonyl group | hydrogen atom | xylyl group | hydrogen atom |
| 18 | ethoxycarbonyl group | hydrogen atom | durenyl group | hydrogen atom |
| 19 | ethoxycarbonyl group | hydrogen atom | phenyl group | hydrogen atom |
| 20 | ethoxycarbonyl group | hydrogen atom | methoxynaphthyl group | hydrogen atom |
| 21 | ethoxycarbonyl group | hydrogen atom | anthryl group | hydrogen atom |
| 22 | ethoxycarbonyl group | hydrogen atom | pyrenyl group | hydrogen atom |

TABLE 3

| Com- | Substituent | | | |
|---|---|---|---|---|
| pound No. | R$^1$ | Ar$^1$ | Ar$^2$ | Ar$^3$ |
| 23 | ethoxycarbonyl group | hydrogen atom | mesityl group | hydrogen atom |
| 24 | ethoxycarbonyl group | hydrogen atom | naphthyl group | hydrogen atom |
| 25 | ethoxycarbonyl group | hydrogen atom | methylnaphthyl group | hydrogen atom |
| 26 | methyl group | aminophenyl group | hydrogen atom | phenyl group |
| 27 | methyl group | tolyl group | hydrogen atom | phenyl group |
| 28 | methyl group | xylyl group | hydrogen atom | phenyl group |
| 29 | methyl group | durenyl group | hydrogen atom | phenyl group |
| 30 | methyl group | phenyl group | hydrogen atom | phenyl group |
| 31 | methyl group | methoxy-naphthyl group | hydrogen atom | phenyl group |
| 32 | methyl group | anthryl group | hydrogen atom | phenyl group |
| 33 | methyl group | pyrenyl group | hydrogen atom | phenyl group |
| 34 | methyl group | mesityl group | hydrogen atom | phenyl group |
| 35 | methyl group | (N,N-dimethyl-amino)phenyl group | hydrogen atom | phenyl group |
| 36 | methyl group | phenyl group | phenyl group | phenyl group |

The electron donor-acceptor linked molecule may be a commercially available product or may be produced (synthesized) as appropriate. When the electron donor-acceptor linked molecule is produced, the method for producing it is not particularly limited, and it can be produced as appropriate by a known production method or with reference to a known production method, for example. Specifically, the production method described in Japanese Patent No. 5213142 may be used, for example.

In the first aspect of the present invention, when the compound (e.g., the electron donor-acceptor linked molecule) has isomers such as tautomers and stereoisomers (e.g., a geometric isomer, a conformer, and an optical isomer), any isomer can be used in the first aspect of the present invention, unless otherwise stated. When the compound (e.g., the electron donor-acceptor linked molecule) can form a salt, the salt also can be used in the first aspect of the present invention, unless otherwise stated. The salt may be an acid addition salt, or may be a base addition salt. Moreover, an acid that forms the acid addition salt may be either an inorganic acid or an organic acid, and a base that forms the base addition salt may be either an inorganic base or an organic base. The inorganic acid is not particularly limited, and examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodic acid, perfluoric acid, perchloric acid, perbromic acid, and periodic acid. The organic acid also is not particularly limited, and examples thereof include p-toluenesulfonic acid, methanesulfonic acid, oxalic acid, p-bromobenzenesulfonic acid, carbonic acid, succinic acid, citric acid, benzoic acid, and acetic acid. The inorganic base is not particularly limited, and examples thereof include ammonium hydroxides, alkali metal hydroxides, alkaline-earth metal hydroxides, carbonates, and hydrogencarbonates. More specifically, the inorganic base may be, for example, sodium hydroxide, potassium hydroxide, potassium carbonate, sodium carbonate, sodium hydrogencarbonate, potassium hydrogencarbonate, calcium hydroxide, and calcium carbonate. The organic base also is not particularly limited, and examples thereof include ethanolamine, triethylamine, and tris(hydroxymethyl)aminomethane. The method for producing these salts also is not particularly limited. For example, they can be produced by adding an acid or a base such as described above to the compound as appropriate by a known method.

Moreover, in the first aspect of the present invention, a chain substituent (e.g., an alkyl group, hydrocarbon groups such as an unsaturated aliphatic hydrocarbon group, etc.) may be straight-chain or branched, unless otherwise stated, and the number of carbons thereof is not particularly limited, and may be, for example, 1 to 40, 1 to 32, 1 to 24, 1 to 18, 1 to 12, 1 to 6, or 1 to 2 (at least 2 in the case of an unsaturated hydrocarbon group). Furthermore, in the first aspect of the present invention, as to a cyclic group (e.g., an aryl group, a heteroaryl group, etc.), the number of ring members (the number of atoms that compose a ring) is not particularly limited and may be, for example, 5 to 32, 5 to 24, 6 to 18, 6 to 12, or 6 to 10. When a substituent or the like has isomers, any isomer can be used, unless otherwise stated. For example, in the case of simply describing as a "naphthyl group", it may be a 1-naphthyl group or a 2-naphthyl group.

[3. Oxidation Reaction Product Production Method]

As described above, the oxidation reaction product production method of the first aspect of the present invention is a method for producing an oxidation reaction product by oxidizing a substance to be oxidized, characterized in that it includes: a radical production step of producing a radical by the radical production method according to the first aspect of the present invention; and an oxidation reaction step of reacting the substance to be oxidized with an oxidizing agent by action of the radical, thereby generating the oxidation reaction product.

The method for carrying out the oxidation reaction product production method of the first aspect of the present invention is not particularly limited. For example, in the mixing step, not only the radical generating catalyst of the first aspect of the present invention and the radical source but also the substance to be oxidized and the oxidizing agent may be mixed together. At this time, as described above, it is preferable to further mix a solvent. Then, in the radical production step, the substance to be oxidized may be reacted with the oxidizing agent by action of the produced radicals, thereby generating the oxidation reaction product. That is, the oxidation reaction step may be performed at the same time with the radical production step in the same reaction system. In this case, the concentrations of the substance to be oxidized and the oxidizing agent are not particularly limited. For example, the molar concentrations of the reactants relative to the solvent are not particularly limited, and can be set as appropriate. For example, the concentration of the substance to be oxidized preferably is set as high as possible because the reaction rate becomes faster in keeping with the elevation of the concentration, and the concentration of the oxidizing agent preferably is set so as to be not too high in order to allow the reaction to proceed smoothly. It is to be noted, however, that this description merely is illustrative, and does not limit the first aspect of the present invention by any means.

In the oxidation reaction product production method of the first aspect of the present invention, the radical also may serve as the oxidizing agent. For example, the radical-generating agent may be an oxoacid, and a radical generated from the oxoacid may be an oxidizing agent. As an illustrative example, the radical-generating agent may be a chlorous acid ion $ClO_2^-$, and the oxidation reaction product may be produced by oxidizing the substance to be oxidized with the radical $ClO_2^-$ generated from the chlorous acid ion $ClO_2^-$ as the oxidizing agent.

Alternatively, the radicals and the oxidizing agent may be different substances, for example. For example, the radical-generating agent may be the electron donor-acceptor linked molecule, the oxidizing agent may be an oxygen molecule $O_2$, and the oxidation reaction product may be produced by oxidizing the substance to be oxidized by action of the radical of the electron donor-acceptor linked molecule and the oxygen molecule.

The substance to be oxidized is not particularly limited, and may be either an organic compound or an inorganic substance, for example. For example, the substance to be oxidized may be triphenylphosphine $Ph_3P$, and the oxidation reaction product may be triphenylphosphine oxide $Ph_3P=O$. Also, for example, the substance to be oxidized may be olefin, and the oxidation reaction product may contain epoxide and/or diol.

The substance to be oxidized may be an aromatic compound (may be referred to as "raw material aromatic compound" hereinafter), for example. In the first aspect of the present invention, the raw material aromatic compound is not particularly limited. It is preferable that an electron donor group is bound to an aromatic ring of the raw material aromatic compound, because, for example, this allows an oxidation reaction (including an oxidative substitution reaction) of the raw material aromatic compound to proceed more easily. The number of the electron donor groups may be one or more, and the electron donor group with a strong electron-donating property is preferable. More specifically, it is more preferable that the raw material aromatic compound is such that at least one substituent selected from the group consisting of $-OR^{100}$, $-NR^{200}{}_2$, and $AR^{100}$ is covalently bound to the aromatic ring. $R^{100}$ is a hydrogen atom or any substituent, and when a plurality of $R^{100}$s are present, they may be the same or different from each other. $R^{200}$s are each a hydrogen atom or any substituent, and they may be the same or different from each other. $AR^{100}$ is an aryl group, and when a plurality of $AR^{100}$s are present, they may be the same or different from each other.

$AR^{100}$ may be a group derived from any aromatic ring such as a benzene ring, a naphthalene ring, an anthracene ring, a phenanthrene ring, a pyridine ring, a thiophene ring, or a pyrene ring. The aromatic ring further may have one or more substituents thereon, and when a plurality of substituents are present, they may be the same or different from each other. $AR^{100}$ may be a phenyl group, for example.

$R^{100}$ preferably is at least one selected from the group consisting of a hydrogen atom, alkyl groups, aryl groups, and acyl groups. The alkyl group preferably is a straight-chain or branched alkyl group having 1 to 6 carbon atoms, and a methyl group is particularly preferable. The acyl group preferably is a straight-chain or branched acyl group having 1 to 6 carbon atoms. The aryl group is the same as $AR^{100}$, for example, and is a phenyl group, for example.

$R^{200}$ preferably is at least one selected from the group consisting of a hydrogen atom, alkyl groups, aryl groups, and acyl groups. The alkyl group preferably is a straight-chain or branched alkyl group having 1 to 6 carbon atoms, and a methyl group is particularly preferable. The acyl group preferably is a straight-chain or branched acyl group having 1 to 6 carbon atoms. The aryl group is the same as $AR^{100}$, for example, and is a phenyl group, for example. As $-NR^{200}{}_2$, an amino group substituted with an electron donor substituent, such as a dimethylamino group or a diphenylamino group, is preferable because of its particularly high electron-donating properties.

Furthermore, the raw material aromatic compound may be such that, for example, a substituent such as an alkyl group is covalently bound to the aromatic ring, and the substituent may be oxidized in the step of generating the oxidation reaction product. For example, the oxidizing agent may contain an oxygen atom, the raw material aromatic compound may contain a methylene group ($-CH_2-$) covalently bound to the aromatic ring, and in the step of generating the oxidation reaction product, the methylene group ($-CH_2-$) may be converted to a carbonyl group ($-CO-$) by oxidation. In this case, an atom or atomic group that is bound to the methylene group and the carbonyl group is not particularly limited, and examples thereof include a hydrogen atom, alkyl groups, and aryl groups. The alkyl group preferably is a straight-chain or branched alkyl group having 1 to 6 carbon atoms. The alkyl group and aryl group may further be substituted with one or more substituents. When they are substituted with a plurality of substituents, the substituents may be the same or different from each other. For example, the methylene group becomes a methyl group ($-CH_3$) when hydrogen is bound thereto, and it becomes a formyl group ($-CHO$) after oxidation. The methylene group becomes an ethyl group ($-CH_2CH_3$) when a methyl group is bound thereto, and it becomes an acetyl group ($-COCH_3$) after oxidation. The methylene group becomes a benzyl group ($-CH_2Ph$) when a phenyl group is bound thereto, and it becomes a benzoyl group ($-COPh$) after oxidation. Alternatively, for example, the substituent (before being oxidized) covalently bound to an aromatic ring may be a formyl group ($-CHO$), and may become a carboxy group ($-COOH$) after oxidation.

In the oxidation reaction product production method of the first aspect of the present invention, the substance to be oxidized may be an olefin, for example, and the olefin may be an aromatic olefin or an aliphatic olefin, for example. The olefin may be an olefin represented by the following chemical formula (A1), for example. Furthermore, the oxidation reaction product of the olefin is not particularly limited, and, for example, may contain at least one of an epoxide and a diol as in the following scheme A. In each of the following chemical formulae (A1), (A2), and (A3), Rs each may be a hydrogen atom or any substituent, and Rs may be the same or different from each other. The substituent may be, for example, an alkyl group, an unsaturated aliphatic hydrocarbon group, an aryl group, a heteroaryl group, a halogen, a hydroxy group ($-OH$), a mercapto group ($-SH$), or an alkylthio group ($-SR$ and R are each an alkyl group), and the substituent may or may not be substituted with another substituent. The alkyl group preferably is a straight-chain or branched alkyl group having 1 to 6 carbon atoms. Furthermore, the olefin, which is a substance to be oxidized, may be an olefin containing one olefin bond (carbon-carbon double bond) or an olefin containing two or more olefin bonds.

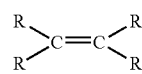

(A1)

Scheme A

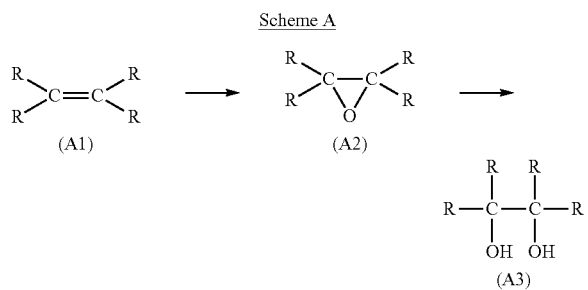

The olefin may be, for example, an aromatic olefin, as described above. That is, for example, in the chemical formula (A1), at least one of Rs may be an aromatic ring (an aryl group or a heteroaryl group). Further, as described above regarding the raw material aromatic compound, the aromatic olefin may be such that at least one substituent selected from the group consisting of —$OR^{100}$, —$NR^{200}{}_2$, and $AR^{100}$ is covalently bound to the aromatic ring.

In the method for producing an oxidation reaction product of an olefin according to the first aspect of the present invention, the olefin may be at least one selected from the group consisting of ethylene, propylene, styrene, and butadiene. Furthermore, the oxidation reaction product may be, as described above, at least one of an epoxide and a diol, for example. The examples thereof are shown in the following schemes A1 to A3. It is to be noted, however, that the schemes A1 to A3 are merely illustrative examples, and in the first aspect of the present invention, the oxidation reactions of ethylene, propylene, and styrene are not limited thereto.

Scheme A1

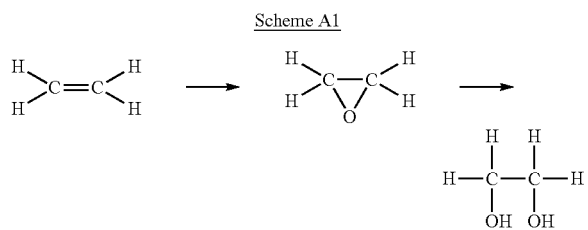

Scheme A2

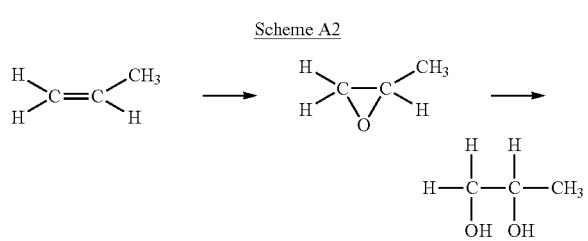

Scheme A3

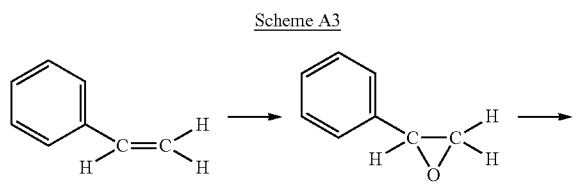

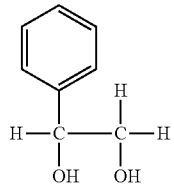

In oxidization of an olefin (for example, the olefin (A1) in the scheme A), for example, by adjusting the concentration of at least one of: the Lewis acid and/or Brønsted acid; the radical source; and the oxidizing agent, oxidation reaction products can be selectively generated. For example, an epoxide is prone to be obtained when the concentrations are low with respect to the substance to be oxidized and a diol is prone to be obtained when the concentrations are high with respect to the substance to be oxidized, although the present invention is not limited thereto. Furthermore, for example, instead of changing the concentrations, by changing the intensity of the reactivity of a radical species generated from the radical source, oxidation reaction products can be selectively generated. For example, an epoxide is prone to be obtained with a radical species having low reactivity and a diol is prone to be obtained with a radical species having high reactivity, although the present invention is not limited thereto. It is to be noted that the use of the oxidation reaction product is not particularly limited. For example, when the substance to be oxidized (raw material aromatic compound) is styrene, styrene oxide can be utilized as an adhesive agent and a diol can be utilized as a perfume. As described above, the epoxide and the diol are in demand for different uses. Thus, the selective production of the epoxide and the diol by controlling the reaction condition allows the first aspect of the present invention to be applied to further wider uses.

Description of Embodiments of Second Aspect of Invention

Next, embodiments of the second aspect of the present invention will be described. It is to be noted, however, that the second aspect of the present invention is not limited by the following descriptions.

[1. Radical Production Method]

As described above, the radical production method according to the second aspect of the present invention is characterized in that it includes a mixing step of mixing a Lewis acid and/or a Brønsted acid with a radical source. The mixture may or may not further contain any substance other than the radical source and the Lewis acid and/or Brønsted and. For example, in the mixing step, it is preferable to further mix a solvent from the viewpoint of reactivity and the like. In the second aspect of the present invention, the "Lewis acid" refers to a substance that acts as a Lewis acid with respect to the radical source, for example. In the second aspect of the present invention, the "solvent" may or may not dissolve the Lewis acid, the Brønsted acid, the radical source, and the like. For example, after the mixing step, the radical source and the Lewis acid and/or Brønsted acid may each be in a state of being dissolved in the solvent, or may each be in a state of being dispersed or precipitated in the solvent.

The radical production method of the second aspect of the present invention includes, for example, after the mixing step, a radical production step of producing radicals through a reaction in the obtained mixture. As described above, the mixture may be in the form of a solution, a suspension, or a colloid, for example. From the viewpoint of reactivity, it is preferable that the mixture is in the form of a solution or a colloid, for example. In the radical production step, the mixture may be merely allowed to stand still at room temperature, or may be subjected to heating, light irradiation, or the like when necessary, for example. The reaction temperature and the reaction time in the radical production step are not particularly limited, and can be set as appropriate depending on the type of the reactant (raw material), the type of a desired product, etc., for example. When the mixture is irradiated with light, the wavelength of the light is not particularly limited, and can be set as appropriate depending on the absorption band of the reactant (raw material), etc., for example. The reaction time and the reaction temperature also can be adjusted by, for example, adjusting the concentrations of the radical source and the Lewis acid and/or Brønsted acid in the mixture. The reaction time can be shortened by setting the concentrations higher, for example. It is to be noted, however, that the second aspect of the present invention is not limited by this description.

The concentrations of the Lewis acid and/or Brønsted acid are not particularly limited, and can be set as appropriate depending on the type of the reactant (raw material), the type of a desired product, etc., for example. Also, the solvent is not particularly limited. For example, the solvent may be either water or an organic solvent, and can be selected as appropriate depending on the types of solutes, etc. The organic solvent may be, for example: a halogenated solvent such as methylene chloride, chloroform, or carbon tetrachloride; ketone such as acetone; a nitrile solvent such as acetonitrile; an alcohol solvent such as methanol or ethanol; an acetic acid solvent; or a sulfuric acid solvent. Only one type of solvent may be used, or two or more types of solvents may be used in combination, for example. The acetic acid solvent and sulfuric acid solvent may be, for example, solvents obtained by dissolving acetic acid and sulfuric acid in water, respectively. They are solvents and, at the same time, also serve as a Lewis acid or a Brønsted acid, for example.

In the radical production method of the second aspect of the present invention, the reaction may be performed by heating the mixture, as described above. Also, it is possible to produce radicals by performing the reaction by merely irradiating the mixture with light without heating or by merely allowing the mixture to stand still at room temperature without heating or light irradiation. The definition of the "room temperature" is not particularly limited, and is from 5° C. to 35° C., for example. Since the radical production method of the first aspect of the present invention can be performed without heating, the cost for the heating with an electric furnace or the like is not necessary, which allows drastic reduction in cost for producing radicals, for example. Besides, since the radical production method of the first aspect of the present invention can be performed without heating, an unexpected runaway reaction caused by a radical chain reaction and accumulation of peroxides are prevented, which greatly improves the safety of the reaction and allows still further reduction in cost, for example. It is to be noted, however, that these descriptions are merely illustrative, and do not limit the first aspect of the present invention by any means.

The radical production method of the second aspect of the present invention may further include, for example, a light irradiation step of irradiating the mixture obtained in the mixing step with light. Then, as described above, radicals may be produced through a reaction caused by the light irradiation. The wavelength of the irradiation light is as described above, for example. A light source is not particularly limited. For example, by using visible light contained in natural light such as sunlight, excitation can be performed easily. Also, for example, instead of or in addition to the natural light, a light source such as a xenon lamp, a halogen lamp, a fluorescent lamp, or a mercury lamp may be used when necessary or may not be used. Further, a filter that cuts wavelengths other than a necessary wavelength may be used when necessary or may not be used.

In the radical production method according to the second aspect of the present invention, the Lewis acidity of the Lewis acid is, for example, 0.4 eV or more, although it is not limited. The upper limit of the Lewis acidity is not particularly limited, and is, for example, 20 eV or less. It is to be noted that the Lewis acidity can be measured, for example, by the method described in Ohkubo, K.; Fukuzumi, S. Chem. Eur. J., 2000, 6, 4532, J. Am. Chem. Soc. 2002, 124, 10270-10271 or the method described in J. Org. Chem. 2003, 68, 4720-4726. Specifically, the Lewis acidity can be measured by the following method.

(Measurement Method of Lewis Acidity)

As to acetonitrile (MeCN) that contains cobalt tetraphenylporphyrin, saturated $O_2$, and an object whose Lewis acidity is to be measured (e.g., a cation of a metal or the like, represented by $M^{n+}$ in the following chemical reaction formula (1a)) in the following chemical reaction formula (1a), the change of the ultraviolet-visible absorption spectrum is measured at room temperature. On the basis of the obtained reaction rate constant ($k_{cat}$), the ΔE value (eV), which is an indicator of the Lewis acidity, can be calculated. The higher the $k_{cat}$, the stronger the Lewis acidity. Furthermore, the Lewis acidity of an organic compound can be estimated from the energy level of the lowest unoccupied molecular orbital (LUMO) calculated by the quantum chemical calculation. The higher the value at the positive side, the stronger the Lewis acidity.

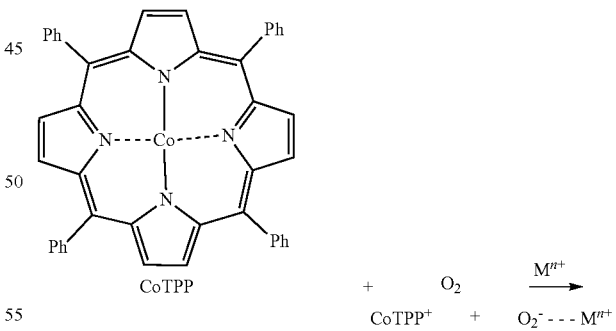

(1a)

Examples of the rate constant of reaction between CoTPP and oxygen in the presence of a Lewis acid, which is an indicator of the Lewis acidity measured (calculated) by the above-described measurement method, are shown below. In the following table, the numerical value expressed in the unit "$k_{cat}$, $M^{-2}S^{-1}$" is a rate constant of reaction between CoTPP and oxygen in the presence of a Lewis acid. The numerical value expressed in the unit "LUMO, eV" is the energy level of LUMO. The "benzetonium chloride" means benzethonium chloride, "benzalkonium chloride" means benzalkonium chloride, "tetramethylammonium hexafluorophosphate" means tetramethylammonium hexafluorophosphate, "tetrabutylammonium hexafluorophosphate" means tetrabutylammonium hexafluorophosphate, and "ammonium hexafluorophosphate" means ammonium hexafluorophosphate.

TABLE TPP

|  | LUMO, eV | $k_{cat}$, M$^{-2}$ s$^{-1}$ |
|---|---|---|
| benzethonium chloride | −4.12 | 0.24 |
| benzalkonium chloride | −4.02 | 0.18 |
| tetramethylammonium hexafluorophosphate | −3.58 | >0.1 |
| tetrabutylammonium hexafluorophosphate | −2.07 | >0.1 |
| ammonium hexafluorophosphate | −5.73 | 20 |

In the radical production method of the second aspect of the present invention, the Lewis acid may include an organic compound. The Lewis acid may be ammonium, for example. The ammonium may be quaternary ammonium, or may be tertiary ammonium, secondary ammonium, primary ammonium, or ammonium, for example.

The organic compound may be, for example, a cationic surfactant, which may be a quaternary ammonium-type cationic surfactant. Examples of the quaternary ammonium-type cationic surfactant include benzalkonium chloride, benzethonium chloride, cetylpyridinium chloride, hexadecyltrimethylammonium bromide, dequalinium chloride, edrophonium, didecyldimethylammonium chloride, tetramethylammonium chloride, benzyltriethylammonium chloride, oxytropium, carbachol, glycopyrronium, safranin, sinapine, tetraethylammonium bromide, hexadecyltrimethylammonium bromide, suxamethonium, sphingomyelin, denatonium, trigonelline, neostigmine, paraquat, pyridostigmine, phellodendrine, pralidoxime methiodide, betaine, betanin, bethanechol, betalain, lecithin, and cholines (e.g., choline chlorides (such as benzoyl choline chloride and a lauroylcholine chloride hydrate), phosphocholine, acetylcholine, choline, dipalmitoylphosphatidylcholine, and choline bitartrate). It is to be noted, however, that in the radical production method of the second aspect of the present invention, the quaternary ammonium is not limited to a surfactant.

In the radical production method of the second aspect of the present invention, the ammonium may be ammonium represented by the following chemical formula (XI), for example.

(XI)

In the chemical formula (XI), $R^{11}$, $R^{21}$, $R^{31}$, and $R^{41}$ are each a hydrogen atom or an alkyl group (e.g., a straight-chain or branched alkyl group having 1 to 40 carbon atoms) and may each include an ether bond, a ketone (carbonyl group), an ester bond, or an amide bond, or an aromatic ring. $R^{11}$, $R^{21}$, $R^{31}$, and $R^{41}$ may be the same or different from each other. $X^-$ is an anion.

The ammonium represented by the chemical formula (XI) may be ammonium represented by the following chemical formula (XII), for example.

(XII)

In the chemical formula (XII), $R^{111}$ is an alkyl group having 5 to 40 carbon atoms and may comprise an ether bond, a ketone (carbonyl group), an ester bond, or an amide bond, or an aromatic ring, and $R^{21}$ and $X^-$ are the same as those in the chemical formula (XI).

In the chemical formula (XII), $R^{21}$ may be a methyl group or a benzyl group, for example. In the benzyl group, one or more hydrogen atoms on the benzene ring may or may not be substituted with any substituent. The substituent may be, for example, an alkyl group, an unsaturated aliphatic hydrocarbon group, an aryl group, a heteroaryl group, a halogen, a hydroxy group (—OH), a mercapto group (—SH), or an alkylthio group (—SR, where R is an alkyl group).

The ammonium represented by the chemical formula (XII) may be ammonium represented by the following chemical formula (XIII), for example.

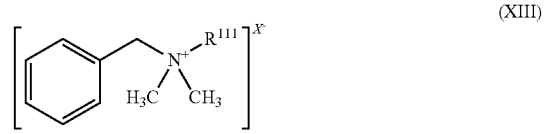

(XIII)

In the chemical formula (XIII), $R^{111}$ and $X^-$ are the same as those in the chemical formula (XII).

The ammonium represented by the chemical formula (XI) may be, for example, at least one selected from the group consisting of benzethonium chloride, benzalkonium chloride, hexadecyltrimethylammonium chloride, tetramethylammonium chloride, ammonium chloride, and tetrabutylammonium chloride. It is particularly preferable that the ammonium represented by the chemical formula (XII) is benzethonium chloride.

Benzethonium chloride (Bzn$^+$Cl$^-$) can be represented by the following chemical formula, for example. Benzalkonium chloride can be, for example, a compound represented by the chemical formula (XIII) where $R^{111}$ is an alkyl group having 8 to 18 carbon atoms and $X^-$ is a chloride ion.

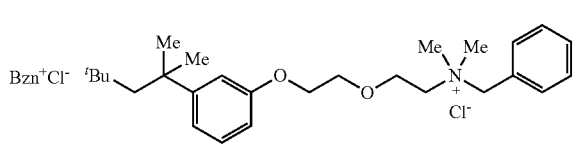

In the chemical formulae (XI), (XII), and (XIII), $X^-$ may be any anion and is not particularly limited. $X^-$ is not limited to a monovalent anion, and may be an anion with any valence, such as a divalent anion or a trivalent anion. When the anion is an anion with a plurality of electric charges, such as a divalent anion or a trivalent anion, the number of molecules of the ammonium (monovalent) in each of the chemical formulae (XI), (XII), and (XIII) is determined by, for example, [the number of molecules of the anion×the valence of the anion] (e.g., when the anion is divalent, the number of molecules of the ammonium (monovalent) is twice the number of molecules of the anion). X⁻ may be, for example, a halogen ion (a fluoride ion, a chloride ion, a bromide ion, or an iodide ion), an acetate ion, a nitrate ion, or a sulfate ion.

In the second aspect of the present invention, the ammonium may include a plurality of ammonium structures ($N^+$) in one molecule. Further, the ammonium may form a dimer, trimer, or the like by association of a plurality of molecules through a π electron interaction, for example.

In the radical production method of the second aspect of the present invention, the Lewis acid may include an inorganic substance. The inorganic substance may include one or both of metal ions and nonmetal ions. The metal ion may include one or both of typical metal ions and transition metal ions. The inorganic substance may be, for example, at least one selected from the group consisting of alkali earth metal ions (e.g., $Ca^{2+}$), rare earth ions, $Mg^{2+}$, $Sc^{3+}$, $Li^+$, $Fe^{2+}$, $Fe^{3+}$, $Al^{3+}$, silicate ions, and borate ions. Examples of the alkali earth metal ion include ions of calcium, strontium, barium, and radium. More specifically, examples of the alkali earth metal ion include $Ca^{2+}$, $Sr^{2+}$, $Ba^{2+}$, and $Ra^{2+}$. Furthermore the "rare earth metal" is a generic name of a set of seventeen elements, specifically, two elements such as scandium $_{21}Sc$ and yttrium $_{39}Y$ and fifteen elements (lanthanoids) from lanthanum $_{57}La$ to lutetium $_{71}Lu$. Examples of the rare earth ion include corresponding trivalent cations of the seventeen elements.

The Lewis acid (including the counter ion) may be, for example, at least one selected from the group consisting of $AlCl_3$, $AlMeCl_2$, $AlMe_2Cl$, $BF_3$, $BPh_3$, $BMe_3$, $TiCl_4$, $SiF_4$, and $SiCl_4$. It is to be noted that the "Ph" indicates a phenyl group and the "Me" indicates a methyl group.

In the radical production method of the second aspect of the present invention, the acid dissociation constant $pK_a$ of the Brønsted acid is, for example, 5 or more. The upper limit of the $pK_a$ is not particularly limited and is, for example, 50 or less.

In the radical production method of the second aspect of the present invention, the radical source may include, for example, at least one selected from the group consisting of halogen ions, hypohalite ions, halite ions, halate ions, and perhalate ions. The radical source may include, for example, an oxoacid or a salt thereof (e.g., a halogen oxoacid or a salt thereof). Examples of the oxoacid include boric acid, carbonic acid, orthocarbonic acid, carboxylic acid, silicic acid, nitrous acid, nitric acid, phosphorous acid, phosphoric acid, arsenic acid, sulfurous acid, sulfuric acid, sulfonic acid, sulfinic acid, chromic acid, dichromic acid, and permanganic acid. Examples of the halogen oxoacid include: chlorine oxoacids such as hypochlorous acid, chlorous acid, chloric acid, and perchloric acid; bromine oxoacids such as hypobromous acid, bromous acid, bromic acid, and perbromic acid; and iodine oxoacids such as hypoiodous acid, iodous acid, iodic acid, and periodic acid. The radical source may be selected as appropriate depending on the use thereof, with consideration given to the intensity of reactivity of a radical species, etc., for example. For example, hypochlorous acid exhibiting high reactivity or chlorous acid exhibiting somewhat lower reactivity than the hypochlorous acid and allowing a reaction to be controlled more easily may be used as appropriate depending on the intended use.

In the radical production method of the second aspect of the present invention, the radical source may include an electron donor-acceptor linked molecule, for example. The electron donor-acceptor linked molecule is not particularly limited. For example, the electron donor-acceptor linked molecule may be such that an electron donor moiety is composed of one or more electron donor groups and an electron acceptor moiety is composed of one or more aromatic cations. In this case, the aromatic cation may be either a monocyclic ring or a condensed ring, and the aromatic ring may or may not include a heteroatom and may or may not have a substituent other than the electron donor group. Furthermore, an aromatic ring that forms the aromatic cation may be, for example, any of a 5- to 26-membered ring, although the number of atoms constituting the ring is not particularly limited.

The aromatic ring that forms the aromatic cation preferably is at least one selected from the group consisting of a pyrrolinium ring, a pyridinium ring, a quinolinium ring, an isoquinolinium ring, an acridinium ring, a 3,4-benzoquinolinium ring, a 5,6-benzoquinolinium ring, a 6,7-benzoquinolinium ring, a 7,8-benzoquinolinium ring, a 3,4-benzoisoquinolinium ring, a 5,6-benzoisoquinolinium ring, a 6,7-benzoisoquinolinium ring, a 7,8-benzoisoquinolinium ring, and rings obtained by substitution of at least one carbon atom of these rings with a heteroatom. For example, when the aromatic ring is a macrocyclic (having many π electrons) aromatic cation such as an acridinium ring, a benzoquinolinium ring, or a benzoisoquinolinium ring, for example, visible light excitation becomes possible if the absorption band shifts toward the longer wavelength side so as to be in the visible region.

The electron donor group preferably is at least one selected from the group consisting of a hydrogen atom, alkyl groups, and aromatic rings. In this case, the aromatic ring further may have one or more substituents on the ring, and when a plurality of substituents are present, they may be the same or different from each other. When a plurality of electron donor groups are present, they may be the same or different from each other. Furthermore, in the electron donor group in this case, it is more preferable that the alkyl group is a straight-chain or branched alkyl group having 1 to 6 carbon atoms. Furthermore, in the electron donor group, it is more preferable that the aromatic ring is at least one selected from the group consisting of a benzene ring, a naphthalene ring, an anthracene ring, a phenanthrene ring, a pyridine ring, a thiophene ring, and a pyrene ring. In the electron donor group, it is more preferable that the substituent on the aromatic ring is at least one selected from the group consisting of alkyl groups, alkoxy groups, primary to tertiary amines, carboxylic acids, and carboxylate esters. In Ar, it is more preferable that the substituent on the aromatic ring is at least one selected from the group consisting of straight-chain or branched alkyl groups having 1 to 6 carbon atoms, straight-chain or branched alkoxy groups having 1 to 6 carbon atoms, primary to tertiary amines, carboxylic acids, and carboxylate esters. In the substituent on the aromatic ring, a "carboxylic acid" refers to a carboxyl group or a group having a carboxyl group added to its end (e.g., a carboxyalkyl group), and a "carboxylate ester" refers to a carboxylate ester group such as an alkoxycarbonyl group or a phenoxycarbonyl group, or an acyloxy group. An alkyl group in the carboxyalkyl group preferably is a straight-chain or branched alkyl group having 1 to 6 carbon atoms, for example. An alkoxy group in the alkoxycarbonyl group preferably is a straight-chain or branched alkoxy group having 1 to 6 carbon atoms, for example.

It is still more preferable that the electron donor group is at least one selected from the group consisting of a phenyl group, an o-tolyl group, an m-tolyl group, a p-tolyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,3,4-trimethylphenyl group, a 2,3,5-trimethylphenyl group, a 2,3,6-trimethylphenyl group, a mesityl group (2,4,6-trimethylphenyl group), and a 3,4,5-trimethylphenyl group. Among these, a mesityl group is particularly preferable from the viewpoint of the lifetime of the electron-transfer state (charge-separated state) and the like. Although the reasons why a mesityl group can bring about a particularly excellent effect is not clear, they are speculated to be as follows, for example: two methyl groups are present in the ortho position, so that the benzene rings of the mesityl groups easily cross at right angles to the aromatic ring of the aromatic cation; and hyperconjugation does not occur very often inside the mesityl group. This, however, merely is an example of a presumable mechanism, and does not limit the second aspect of the present invention by any means.

The electron donor-acceptor linked molecule preferably is at least one selected from the group consisting of: nitrogen-containing aromatic cation derivatives represented by the following formulae (A-1) to (A-8); quinolinium ion derivatives represented by the following formula (I); stereoisomers and tautomers thereof; and salts thereof, from the viewpoints of the lifetime, oxidizing power, reducing power, and the like of the electron-transfer state (charge-separated state).

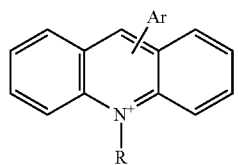
(A-1)

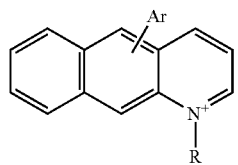
(A-2)

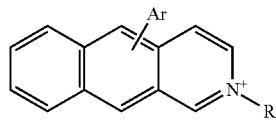
(A-3)

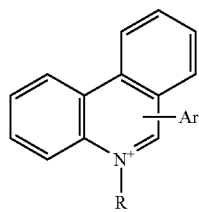
(A-4)

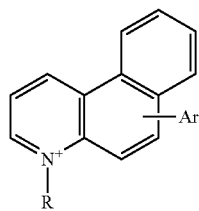
(A-5)

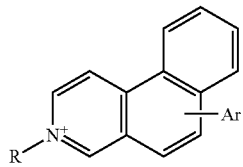
(A-6)

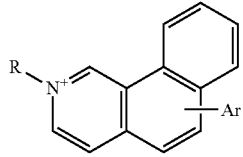
(A-7)

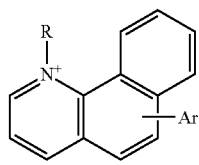
(A-8)

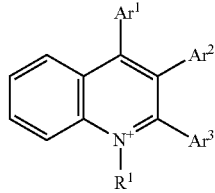
(I)

In the formulae (A-1) to (A-8), R is a hydrogen atom or any substituent, Ar is the electron donor group, and the number of Ars may be one or more, and when a plurality of Ars are present, they may be the same or different from each other, and the nitrogen-containing aromatic ring that forms a nitrogen-containing aromatic cation may or may not have at least one substituent other than R and Ar. In the formula (I), $R^1$ is a hydrogen atom or any substituent, $Ar^1$ to $Ar^3$ are each a hydrogen atom or the electron donor group and may be the same or different from each other, and at least one of $Ar^1$ to $Ar^3$ is the electron donor group.

In the formulae (A-1) to (A-8), R preferably is a hydrogen atom, an alkyl group, a benzyl group, a carboxyalkyl group (an alkyl group with a carboxyl group added to its end), an aminoalkyl group (an alkyl group having an amino group added to its end), or a polyether chain. More preferably, R is a hydrogen atom, a straight-chain or branched alkyl group having 1 to 6 carbon atoms, a benzyl group, a straight-chain or branched alkyl group having 1 to 6 carbon atoms with a carboxyl group added to its end, a straight-chain or branched alkyl group having 1 to 6 carbon atoms with an amino group added to its end, or a polyethylene glycol (PEG) chain. The PEG chain is an example of the polyether chain. The type of the polyether chain is not limited thereto, and the polyether chain may be of any type. In R, the degree of polymerization of the polyether chain is not particularly limited, and is, for example, 1 to 100, preferably 1 to 50, and more preferably 1 to 10. In the case where the polyether chain is a PEG chain, the degree of polymerization is not particularly limited, and is, for example, 1 to 100, preferably 1 to 50, and more preferably 1 to 10.

It is more preferable that the electron donor-acceptor linked molecule is at least one selected from the group consisting of 9-substituted acridinium ions represented by the following formula (A-9), tautomers thereof, and stereoisomers thereof.

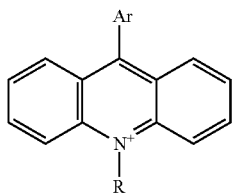

(A-9)

In the formula (A-9), R and Ar are the same as those in the formula (A-1).

Furthermore, it is particularly preferable that the electron donor-acceptor linked molecule is a 9-mesityl-10-methyl-acridinium ion represented by the following formula (A-10). By photoexcitation of this 9-mesityl-10-methylacridinium ion, it is possible to generate a long-lived electron-transfer state (charge-separated state) having a high oxidizing power and a high reducing power. As excitation light for the photoexcitation, it is possible to use visible light, for example.

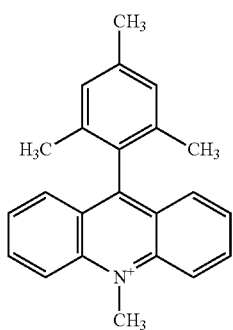

(A-10)

Examples of the 9-substituted acridinium ion represented by the formula (A-9) further include compounds (A-101) to (A-116) shown in the following table, in addition to the one represented by the above formula (A-10).

TABLE 1

| Compound | Substituent | |
|---|---|---|
| No. | R | Ar |
| (A-101) | methyl group | phenyl group |
| (A-102) | methyl group | o-tolyl group |
| (A-103) | methyl group | m-tolyl group |
| (A-104) | methyl group | p-tolyl group |
| (A-105) | methyl group | 2,3-dimethylphenyl group |
| (A-106) | methyl group | 2,4-dimethylphenyl group |
| (A-107) | methyl group | 2,5-dimethylphenyl group |
| (A-108) | methyl group | 2,6-dimethylphenyl group |
| (A-109) | methyl group | 3,4-dimethylphenyl group |
| (A-110) | methyl group | 3,5-dimethylphenyl group |
| (A-111) | methyl group | 2,3,4-trimethylphenyl group |
| (A-112) | methyl group | 2,3,5-trimethylphenyl group |
| (A-113) | methyl group | 2,3,6-trimethylphenyl group |
| (A-114) | methyl group | mesityl group (2,4,6-trimethylphenyl group) |
| (A-115) | methyl group | 3,4,5-trimethylphenyl group |
| (A-116) | methyl group | hydrogen atom |

In the quinolinium ion derivative represented by the formula (I), $R^1$ preferably is a hydrogen atom, an alkyl group, a benzyl group, a carboxyalkyl group (an alkyl group with a carboxyl group added to its end), an aminoalkyl group (an alkyl group having an amino group added to its end), or a polyether chain, for example. More preferably, $R^1$ is a hydrogen atom, a straight-chain or branched alkyl group having 1 to 6 carbon atoms, a benzyl group, a straight-chain or branched alkyl group having 1 to 6 carbon atoms with a carboxyl group added to its end, a straight-chain or branched alkyl group having 1 to 6 carbon atoms with an amino group added to its end, or a polyethylene glycol (PEG) chain, for example. The PEG chain is an example of the polyether chain. The type of the polyether chain is not limited thereto, and the polyether chain may be of any type. In $R^1$, the degree of polymerization of the polyether chain is not particularly limited, and is, for example, 1 to 100, preferably 1 to 50, and more preferably 1 to 10. In the case where the polyether chain is a PEG chain, the degree of polymerization is not particularly limited, and is, for example, 1 to 100, preferably 1 to 50, and more preferably 1 to 10. Furthermore, $Ar^1$ to $Ar^3$ preferably are each a hydrogen atom, an alkyl group, or an aromatic ring, for example, and the alkyl group more preferably is a straight-chain or branched alkyl group having 1 to 6 carbon atoms. In $Ar^1$ to $Ar^3$, the aromatic ring further may have one or more substituents on the ring, and when a plurality of substituents are present, they may be the same or different from each other.

In $Ar^1$ to $Ar^3$ in the formula (I), the aromatic ring more preferably is a benzene ring, a naphthalene ring, an anthracene ring, a phenanthrene ring, a pyridine ring, a thiophene ring, or a pyrene ring, for example. Furthermore, in $Ar^1$ to $Ar^3$, the substituent on the aromatic ring more preferably is an alkyl group, an alkoxy group, any one of primary to tertiary amines, a carboxylic acid, or a carboxylate ester. Still more preferably, the substituent on the aromatic ring is a straight-chain or branched alkyl group having 1 to 6 carbon atoms, a straight-chain or branched alkoxy group having 1 to 6 carbon atoms, any one of primary to tertiary amines, a carboxylic acid, or a carboxylate ester. The secondary amine is not particularly limited, and preferably is an alkylamino group, and more preferably is a straight-chain or branched alkylamino group having 1 to 6 carbon atoms, for example. The tertiary amine is not particularly limited, and preferably is a dialkylamino group, and more preferably is a dialkylamino group with a straight-chain or branched alkyl group having 1 to 6 carbon atoms, for example.

In the substituent on the aromatic ring in $Ar^1$ to $Ar^3$, a "carboxylic acid" refers to a carboxyl group or a group having a carboxyl group added to its end (e.g., a carboxyalkyl group), and a "carboxylate ester" refers to a carboxylate ester group such as an alkoxycarbonyl group or a phenoxycarbonyl group, or an acyloxy group. An alkyl group in the carboxyalkyl group preferably is a straight-chain or branched alkyl group having 1 to 6 carbon atoms, for example. An alkoxy group in the alkoxycarbonyl group preferably is a straight-chain or branched alkoxy group having 1 to 6 carbon atoms, for example.

Among the quinolinium ion derivatives represented by the formula (I), for example, quinolinium ion derivatives represented by the following formulae 1 to 5 are particularly preferable in terms of a long lifetime, a high oxidizing power, a high reducing power, and the like of the charge-separated state.

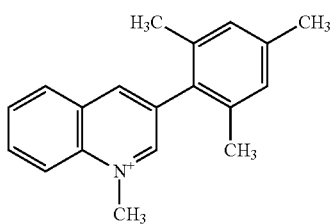

1

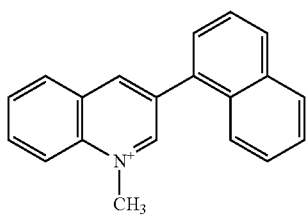

2

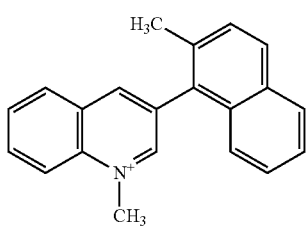

3

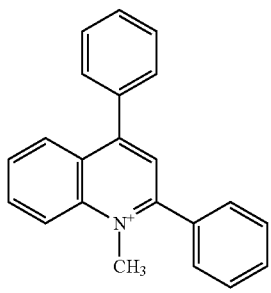

4

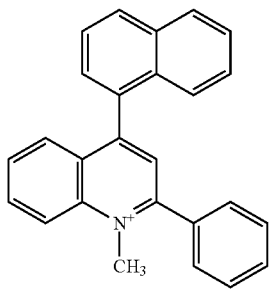

5

TABLE 2

| Compound No. | Substituent | | | |
|---|---|---|---|---|
| | R[1] | Ar[1] | Ar[2] | Ar[3] |
| 6 | methyl group | hydrogen atom | phenyl group | hydrogen atom |
| 7 | methyl group | hydrogen atom | tolyl group | hydrogen atom |
| 8 | methyl group | hydrogen atom | xylyl group | hydrogen atom |
| 9 | methyl group | hydrogen atom | durenyl group | hydrogen atom |
| 10 | methyl group | hydrogen atom | phenyl group | hydrogen atom |
| 11 | methyl group | hydrogen atom | aminophenyl group | hydrogen atom |
| 12 | methyl group | hydrogen atom | methoxynaphthyl group | hydrogen atom |
| 13 | methyl group | hydrogen atom | anthryl group | hydrogen atom |
| 14 | methyl group | hydrogen atom | pyrenyl group | hydrogen atom |
| 15 | ethoxycarbonyl group | hydrogen atom | phenyl group | hydrogen atom |
| 16 | ethoxycarbonyl group | hydrogen atom | tolyl group | hydrogen atom |
| 17 | ethoxycarbonyl group | hydrogen atom | xylyl group | hydrogen atom |
| 18 | ethoxycarbonyl group | hydrogen atom | durenyl group | hydrogen atom |
| 19 | ethoxycarbonyl group | hydrogen atom | phenyl group | hydrogen atom |
| 20 | ethoxycarbonyl group | hydrogen atom | methoxynaphthyl group | hydrogen atom |
| 21 | ethoxycarbonyl group | hydrogen atom | anthryl group | hydrogen atom |
| 22 | ethoxycarbonyl group | hydrogen atom | pyrenyl group | hydrogen atom |

TABLE 3

| Compound No. | Substituent | | | |
|---|---|---|---|---|
| | R[1] | Ar[1] | Ar[2] | Ar[3] |
| 23 | ethoxycarbonyl group | hydrogen atom | mesityl group | hydrogen atom |
| 24 | ethoxycarbonyl group | hydrogen atom | naphthyl group | hydrogen atom |
| 25 | ethoxycarbonyl group | hydrogen atom | methylnaphthyl group | hydrogen atom |
| 26 | methyl group | aminophenyl group | hydrogen atom | phenyl group |
| 27 | methyl group | tolyl group | hydrogen atom | phenyl group |
| 28 | methyl group | xylyl group | hydrogen atom | phenyl group |
| 29 | methyl group | durenyl group | hydrogen atom | phenyl group |
| 30 | methyl group | phenyl group | hydrogen atom | phenyl group |
| 31 | methyl group | methoxy-naphthyl group | hydrogen atom | phenyl group |
| 32 | methyl group | anthryl group | hydrogen atom | phenyl group |
| 33 | methyl group | pyrenyl group | hydrogen atom | phenyl group |
| 34 | methyl group | mesityl group | hydrogen atom | phenyl group |
| 35 | methyl group | (N,N-dimethyl-amino) phenyl group | hydrogen atom | phenyl group |
| 36 | methyl group | phenyl group | phenyl group | phenyl group |

In addition to the above compounds 1 to 5, compounds 6 to 36 shown in Tables 1 and 2 below also are particularly preferable, for example. Tables 2 and 3 show the structures of the compounds 6 to 36 by indicating the combination of R[1] and Ar[1] to Ar[3] in the formula (I). Those skilled in the art can produce and use the compounds 6 to 36 easily according to the production and use of the compounds 1 to 5 with reference to examples to be described below, without undue trial and error, complicated and advanced experiments, etc.

The electron donor-acceptor linked molecule may be a commercially available product or may be produced (synthesized) as appropriate. When the electron donor-acceptor linked molecule is produced, the method for producing it is not particularly limited, and it can be produced as appropriate by a known production method or with reference to a known production method, for example. Specifically, the production method described in Japanese Patent No. 5213142 may be used, for example.

In the second aspect of the present invention, when the compound (e.g., the electron donor-acceptor linked molecule) has isomers such as tautomers and stereoisomers (e.g., a geometric isomer, a conformer, and an optical isomer), any isomer can be used in the second aspect of the present invention, unless otherwise stated. When the compound (e.g., the electron donor-acceptor linked molecule) can form a salt, the salt also can be used in the second aspect of the present invention, unless otherwise stated. The salt may be an acid addition salt, or may be a base addition salt. Moreover, an acid that forms the acid addition salt may be either an inorganic acid or an organic acid, and a base that forms the base addition salt may be either an inorganic base or an organic base. The inorganic acid is not particularly limited, and examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodic acid, perfluoric acid, perchloric acid, perbromic acid, and periodic acid. The organic acid also is not particularly limited, and examples thereof include p-toluenesulfonic acid, methanesulfonic acid, oxalic acid, p-bromobenzenesulfonic acid, carbonic acid, succinic acid, citric acid, benzoic acid, and acetic acid. The inorganic base is not particularly limited, and examples thereof include ammonium hydroxides, alkali metal hydroxides, alkaline-earth metal hydroxides, carbonates, and hydrogencarbonates. More specifically, the inorganic base may be, for example, sodium hydroxide, potassium hydroxide, potassium carbonate, sodium carbonate, sodium hydrogencarbonate, potassium hydrogencarbonate, calcium hydroxide, and calcium carbonate. The organic base also is not particularly limited, and examples thereof include ethanolamine, triethylamine, and tris(hydroxymethyl)aminomethane. The method for producing these salts also is not particularly limited. For example, they can be produced by adding an acid or a base such as described above to the compound as appropriate by a known method.

Moreover, in the second aspect of the present invention, a chain substituent (e.g., an alkyl group, hydrocarbon groups such as an unsaturated aliphatic hydrocarbon group, etc.) may be straight-chain or branched, unless otherwise stated, and the number of carbons thereof is not particularly limited, and may be, for example, 1 to 40, 1 to 32, 1 to 24, 1 to 18, 1 to 12, 1 to 6, or 1 to 2 (at least 2 in the case of an unsaturated hydrocarbon group). Furthermore, in the second aspect of the present invention, as to a cyclic group (e.g., an aryl group, a heteroaryl group, etc.), the number of ring members (the number of atoms that compose a ring) is not particularly limited and may be, for example, 5 to 32, 5 to 24, 6 to 18, 6 to 12, or 6 to 10. When a substituent or the like has isomers, any isomer can be used, unless otherwise stated. For example, in the case of simply describing as a "naphthyl group", it may be a 1-naphthyl group or a 2-naphthyl group.

[2. Oxidation Reaction Product Production Method]

As described above, the oxidation reaction product production method of the second aspect of the present invention is a method for producing an oxidation reaction product by oxidizing a substance to be oxidized, characterized in that it includes: a radical production step of producing a radical by the radical production method according to the second aspect of the present invention; and an oxidation reaction step of reacting the substance to be oxidized with an oxidizing agent by action of the radical, thereby generating the oxidation reaction product.

The method for carrying out the oxidation reaction product production method of the second aspect of the present invention is not particularly limited. For example, in the mixing step, not only the radical source and the Lewis acid and/or Brønsted acid but also the substance to be oxidized and the oxidizing agent further may be mixed together. At this time, as described above, it is preferable to further mix a solvent. Then, in the radical production step, the substance to be oxidized may be reacted with the oxidizing agent by action of the produced radicals, thereby generating the oxidation reaction product. That is, the oxidation reaction step may be performed at the same time with the radical production step in the same reaction system. In this case, the concentrations of the substance to be oxidized and the oxidizing agent are not particularly limited, and can be set as appropriate. In order to allow the oxidation reaction to proceed rapidly, for example, the concentration of the substance to be oxidized may be set as high as possible and the concentration of the oxidizing agent may be set so as to be not too high and not too low, for example. It is to be noted, however, that the method for allowing the oxidation reaction to proceed rapidly is not limited thereto.

In the oxidation reaction product production method of the second aspect of the present invention, the radical also may serve as the oxidizing agent. For example, the radical-generating agent may be an oxoacid, and a radical generated from the oxoacid may be an oxidizing agent. As an illustrative example, the radical-generating agent may be a chlorous acid ion $ClO_2^-$, and the oxidation reaction product may be produced by oxidizing the substance to be oxidized with the radical $ClO_2$. generated from the chlorous acid ion $ClO_2^-$ as the oxidizing agent.

Alternatively, the radicals and the oxidizing agent may be different substances, for example. For example, the radical-generating agent may be the electron donor-acceptor linked molecule, the oxidizing agent may be an oxygen molecule $O_2$, and the oxidation reaction product may be produced by oxidizing the substance to be oxidized by action of the radical of the electron donor-acceptor linked molecule and the oxygen molecule.

The substance to be oxidized is not particularly limited, and may be either an organic compound or an inorganic substance, for example. For example, the substance to be oxidized may be triphenylphosphine $Ph_3P$, and the oxidation reaction product may be triphenylphosphine oxide $Ph_3P=O$. Also, for example, the substance to be oxidized may be olefin, and the oxidation reaction product may contain epoxide and/or diol.

The substance to be oxidized may be an aromatic compound (may be referred to as "raw material aromatic compound" hereinafter), for example. In the second aspect of the present invention, the raw material aromatic compound is not particularly limited. It is preferable that an electron donor group is bound to an aromatic ring of the raw material aromatic compound, because, for example, this allows an oxidation reaction (including an oxidative substitution reaction) of the raw material aromatic compound to proceed more easily. The number of the electron donor groups may be one or more, and the electron donor group with a strong electron-donating property is preferable. More specifically, it is more preferable that the raw material aromatic compound is such that at least one substituent selected from the group consisting of —OR$^{100}$, —NR$^{200}_2$, and AR$^{100}$ is covalently bound to the aromatic ring. R$^{100}$ is a hydrogen atom or any substituent, and when a plurality of R$^{100}$s are present, they may be the same or different from each other. R$^{200}$s are each a hydrogen atom or any substituent, and they may be the same or different from each other. AR$^{100}$ is an aryl group, and when a plurality of AR$^{100}$s are present, they may be the same or different from each other.

AR$^{100}$ may be a group derived from any aromatic ring such as a benzene ring, a naphthalene ring, an anthracene ring, a phenanthrene ring, a pyridine ring, a thiophene ring, or a pyrene ring. The aromatic ring further may have one or more substituents thereon, and when a plurality of substituents are present, they may be the same or different from each other. AR$^{100}$ may be a phenyl group, for example.

R$^{100}$ preferably is at least one selected from the group consisting of a hydrogen atom, alkyl groups, aryl groups, and acyl groups. The alkyl group preferably is a straight-chain or branched alkyl group having 1 to 6 carbon atoms, and a methyl group is particularly preferable. The acyl group preferably is a straight-chain or branched acyl group having 1 to 6 carbon atoms. The aryl group is the same as AR$^{100}$, for example, and is a phenyl group, for example.

R$^{200}$ preferably is at least one selected from the group consisting of a hydrogen atom, alkyl groups, aryl groups, and acyl groups. The alkyl group preferably is a straight-chain or branched alkyl group having 1 to 6 carbon atoms, and a methyl group is particularly preferable. The acyl group preferably is a straight-chain or branched acyl group having 1 to 6 carbon atoms. The aryl group is the same as AR$^{100}$, for example, and is a phenyl group, for example. As —NR$^{200}_2$, an amino group substituted with an electron donor substituent, such as a dimethylamino group or a diphenylamino group, is preferable because of its particularly high electron-donating properties.

Furthermore, the raw material aromatic compound may be such that, for example, a substituent such as an alkyl group is covalently bound to the aromatic ring, and the substituent may be oxidized in the step of generating the oxidation reaction product. For example, the oxidizing agent may contain an oxygen atom, the raw material aromatic compound may contain a methylene group (—CH$_2$—) covalently bound to the aromatic ring, and in the step of generating the oxidation reaction product, the methylene group (—CH$_2$—) may be converted to a carbonyl group (—CO—) by oxidation. In this case, an atom or atomic group that is bound to the methylene group and the carbonyl group is not particularly limited, and examples thereof include a hydrogen atom, alkyl groups, and aryl groups. The alkyl group preferably is a straight-chain or branched alkyl group having 1 to 6 carbon atoms. The alkyl group and aryl group may further be substituted with one or more substituents. When they are substituted with a plurality of substituents, the substituents may be the same or different from each other. For example, the methylene group becomes a methyl group (—CH$_3$) when hydrogen is bound thereto, and it becomes a formyl group (—CHO) after oxidation. The methylene group becomes an ethyl group (—CH$_2$CH$_3$) when a methyl group is bound thereto, and it becomes an acetyl group (—COCH$_3$) after oxidation. The methylene group becomes a benzyl group (—CH$_2$Ph) when a phenyl group is bound thereto, and it becomes a benzoyl group (—COPh) after oxidation. Alternatively, for example, the substituent (before being oxidized) covalently bound to an aromatic ring may be a formyl group (—CHO), and may become a carboxy group (—COOH) after oxidation.

The substance to be oxidized may be an olefin, for example, and the olefin may be an aromatic olefin or an aliphatic olefin, for example. The olefin may be an olefin represented by the following chemical formula (A1), for example. Furthermore, the oxidation reaction product of the olefin is not particularly limited, and, for example, may contain at least one of an epoxide and a diol as in the following scheme A. In each of the following chemical formulae (A1), (A2), and (A3), Rs each may be a hydrogen atom or any substituent, and Rs may be the same or different from each other. The substituent may be, for example, an alkyl group, an unsaturated aliphatic hydrocarbon group, an aryl group, a heteroaryl group, a halogen, a hydroxy group (—OH), a mercapto group (—SH), or an alkylthio group (—SR and R are each an alkyl group), and the substituent may or may not be substituted with another substituent. The alkyl group preferably is a straight-chain or branched alkyl group having 1 to 6 carbon atoms. Furthermore, the olefin, which is a substance to be oxidized, may be an olefin containing one olefin bond (carbon-carbon double bond) or an olefin containing two or more olefin bonds.

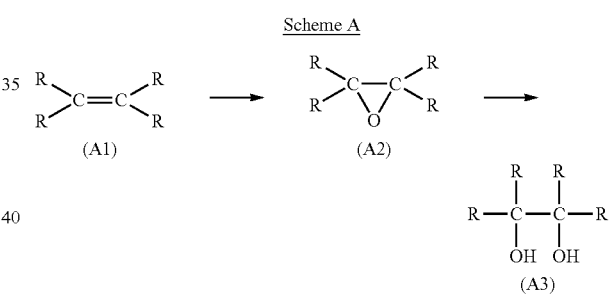

The olefin may be, for example, an aromatic olefin. That is, for example, in the chemical formula (A1), at least one of Rs may be an aromatic ring (an aryl group or a heteroaryl group). In the second aspect of the present invention, the aromatic olefin is not particularly limited. It is preferable that an electron donor group is bound to an aromatic ring of the aromatic olefin, for example, because this allows an oxidation reaction (including an oxidative substitution reaction) of the aromatic olefin to proceed more easily. The number of the electron donor groups may be one or more, and the electron donor group with a strong electron-donating property is preferable. More specifically, it is more preferable that the aromatic olefin is such that at least one substituent selected from the group consisting of —OR$^{100}$, —NR$^{200}_2$, and AR$^{100}$ is covalently bound to the aromatic ring.

In the oxidation reaction product production method of the second aspect of the present invention, the olefin may be at least one selected from the group consisting of ethylene, propylene, styrene, and butadiene. Furthermore, the oxidation reaction product may be, as described above, at least one of an epoxide and a diol, for example. The examples thereof are shown in the following schemes A1 to A3. It is to be noted, however, that the schemes A1 to A3 are merely illustrative examples, and in the present invention, the oxidation reactions of ethylene, propylene and styrene are not limited thereto.

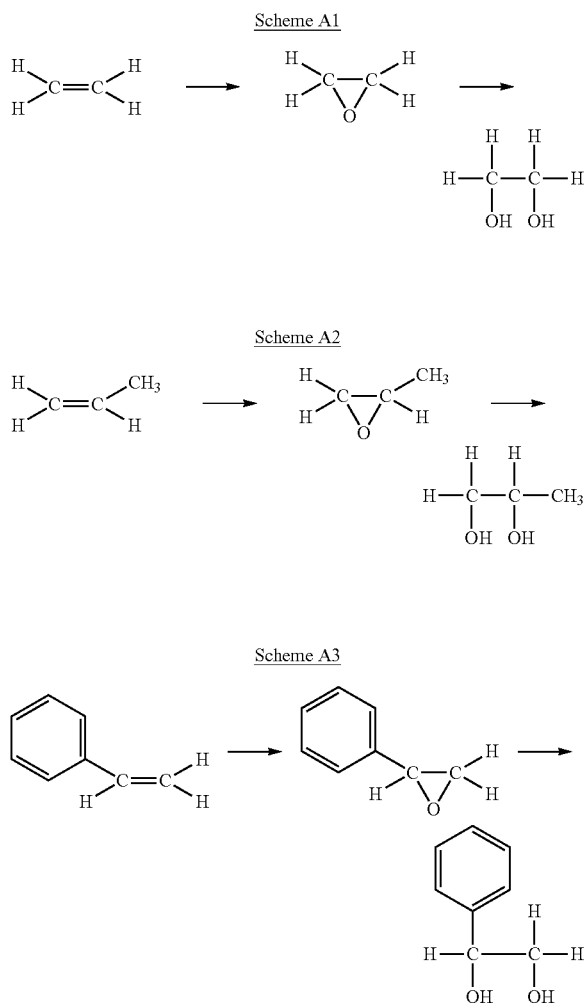

In oxidization of an olefin (for example, the olefin (A1) in the scheme A), for example, by adjusting the concentration of at least one of: the Lewis acid and/or Brønsted acid; the radical source; and the oxidizing agent, oxidation reaction products can be selectively generated. For example, an epoxide is prone to be obtained when the concentrations are low with respect to the substance to be oxidized and a diol is prone to be obtained when the concentrations are high with respect to the substance to be oxidized, although the present invention is not limited thereto. Furthermore, for example, instead of changing the concentrations, by changing the intensity of the reactivity of a radical species generated from the radical source, oxidation reaction products can be selectively generated. For example, an epoxide is prone to be obtained with a radical species having low reactivity and a diol is prone to be obtained with a radical species having high reactivity, although the present invention is not limited thereto. It is to be noted that the use of the oxidation reaction product is not particularly limited. For example, when the substance to be oxidized (raw material aromatic compound) is styrene, styrene oxide can be utilized as an adhesive agent and a diol can be utilized as a perfume.

As described above, the epoxide and the diol are in demand for different uses. Thus, the selective production of the epoxide and the diol by controlling the reaction condition allows the second aspect of the present invention to be applied to further wider uses.

Description of Embodiments of Third and Fourth Aspects of Invention

First, embodiments of the third and fourth aspects of the present invention will be described. It is to be noted, however, that the third and fourth aspects of the present invention are not limited by the following descriptions.

[1. Drug]

As described above, the drug according to the third aspect of the present invention is a drug characterized in that it contains: a radical generating catalyst; and a radical source, wherein the radical generating catalyst includes either or both of: ammonium and/or a salt thereof; and a substance having Lewis acidic properties and/or Brønsted acidic properties. In the drug of the third aspect of the present invention, other configurations or conditions are not particularly limited. The ammonium also may serve as the substance having Lewis acidic properties and/or Brønsted acidic properties.

As described above, the drug for use in agriculture and livestock industry according to the fourth aspect of the present invention is a drug characterized in that it contains: a radical generating catalyst; and a radical source, wherein the radical generating catalyst includes either or both of: ammonium and/or a salt thereof; and a substance having Lewis acidic properties and/or Brønsted acidic properties. That is, the drug for use in agriculture and livestock industry according to the fourth aspect of the present invention is the drug according to the third aspect of the present invention used as a drug for use in agriculture and livestock industry, and the fourth aspect of the present invention is part of the third aspect of the present invention. In the drug for use in agriculture and livestock industry according to the fourth aspect of the present invention, other configurations or conditions are not particularly limited The drug for use in agriculture and livestock industry according to the fourth aspect of the present invention is highly safe and has a high sterilizing effect. Thus, the drug for use in agriculture and livestock industry according to the fourth aspect of the present invention can be used widely for sterilization, deodorization, etc. in agriculture and livestock industry, for example. Further, the drug for use in agriculture and livestock industry according to the fourth aspect of the present invention is less liable to cause corrosion, for example. Even when the drug is applied to metals, corrosion of the metals is less liable to occur. Thus, the drug for use in agriculture and livestock industry according to the fourth aspect of the present invention can be used for a target object containing a metal, for example.

The inventors of the present invention found out through research that ammonium serves as a radical generating catalyst. As a result of further research, the inventors of the present invention further found out that ammonium serving as a radical generating catalyst may have properties as a Lewis acid. That is, while the reason why the ammonium serves as a radical generating catalyst is not clear, it is presumably because the ammonium has a function as a Lewis acid. As a result of still further research, the inventors of the present invention discovered a radical generating catalyst including a substance having Lewis acidic properties and/or Brønsted acidic properties. In the third aspect of the present invention, the "Lewis acid" refers to a substance that acts as a Lewis acid with respect to the radical source, for example.

The Lewis acidity of the radical generating catalyst contained in the drug of the third aspect of the present invention (may be referred to as "the radical generating catalyst of the third aspect of the present invention" hereinafter) is, for example, 0.4 eV or more. The upper limit of the Lewis acidity is not particularly limited, and is, for example, 20 eV or less. It is to be noted that the Lewis acidity can be measured, for example, by the method described in Ohkubo, K.; Fukuzumi, S. Chem. Eur. J., 2000, 6, 4532, J. Am. Chem. Soc. 2002, 124, 10270-10271 or the method described in J. Org. Chem. 2003, 68, 4720-4726. Specifically, the Lewis acidity can be measured by the following method.

(Measurement Method of Lewis Acidity)

As to acetonitrile (MeCN) that contains cobalt tetraphenylporphyrin, saturated $O_2$, and an object whose Lewis acidity is to be measured (e.g., a cation of a metal or the like, represented by $M^{n+}$ in the following chemical reaction formula (1a)) in the following chemical reaction formula (1a), the change of the ultraviolet-visible absorption spectrum is measured at room temperature. On the basis of the obtained reaction rate constant ($k_{cat}$), the ΔE value (eV), which is an indicator of the Lewis acidity, can be calculated. The higher the $k_{cat}$, the stronger the Lewis acidity. Furthermore, the Lewis acidity of an organic compound can be estimated from the energy level of the lowest unoccupied molecular orbital (LUMO) calculated by the quantum chemical calculation. The higher the value at the positive side, the stronger the Lewis acidity.

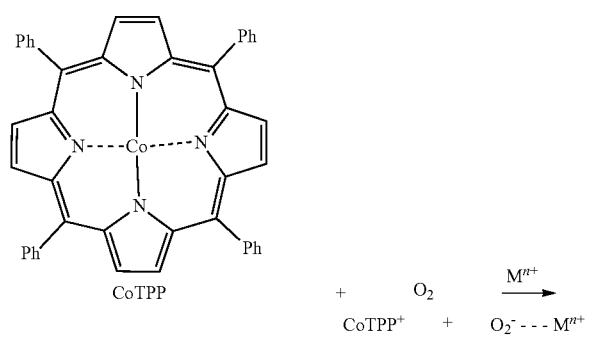

(1a)

Examples of the rate constant of reaction between CoTPP and oxygen in the presence of a Lewis acid, which is an indicator of the Lewis acidity measured (calculated) by the above-described measurement method, are shown below. In the following table, the numerical value expressed in the unit "$k_{cat}$, $M^{-2}S^{-1}$" is a rate constant of reaction between CoTPP and oxygen in the presence of a Lewis acid. The numerical value expressed in the unit "LUMO, eV" is the energy level of LUMO. The "benzetonium chloride" means benzethonium chloride, "benzalkonium chloride" means benzalkonium chloride, "tetramethylammonium hexafluorophosphate" means tetramethylammonium hexafluorophosphate, "tetrabutylammonium hexafluorophosphate" means tetrabutylammonium hexafluorophosphate, and "ammonium hexafluorophosphate" means ammonium hexafluorophosphate.

TABLE TPP

| | LUMO, eV | $k_{cat}$, $M^{-2} s^{-1}$ |
|---|---|---|
| benzetonium chloride | −4.12 | 0.24 |
| benzalkonium chloride | −4.02 | 0.18 |
| tetramethylammonium hexafluorophosphate | −3.58 | >0.1 |
| tetrabutylammonium hexafluorophosphate | −2.07 | >0.1 |
| ammonium hexafluorophosphate | −5.73 | 20 |

In the radical generating catalyst of the third aspect of the present invention, the ammonium may be quaternary ammonium, or may be tertiary ammonium, secondary ammonium, primary ammonium, or ammonium, for example.

In the radical generating catalyst of the third aspect of the present invention, the ammonium or the substance having Lewis acidic properties and/or Brønsted acidic properties may be, for example, a cationic surfactant, which may be a quaternary ammonium-type cationic surfactant. Examples of the quaternary ammonium-type cationic surfactant include benzalkonium chloride, benzethonium chloride, cetylpyridinium chloride, hexadecyltrimethylammonium bromide, dequalinium chloride, edrophonium, didecyldimethylammonium chloride, tetramethylammonium chloride, tetrabutylammonium chloride, benzyltriethylammonium chloride, oxytropium, carbachol, glycopyrronium, safranin, sinapine, tetraethylammonium bromide, hexadecyltrimethylammonium bromide, suxamethonium, sphingomyelin, denatonium, trigonelline, neostigmine, paraquat, pyridostigmine, phellodendrine, pralidoxime methiodide, betaine, betanin, bethanechol, betalain, lecithin, and cholines (e.g., choline chlorides [such as benzoyl choline chloride and a lauroylcholine chloride hydrate], phosphocholine, acetylcholine, choline, dipalmitoylphosphatidylcholine, and choline bitartrate). It is to be noted, however, that, in the radical production method of the third aspect of the present invention, the quaternary ammonium is not limited to a surfactant. Also, in the radical generating catalyst of the third aspect of the present invention, one type of ammonium or a salt thereof may be used, or two or more types of ammonium or salts thereof may be used in combination, for example, and one type of substance having Lewis acidic properties and/or Brønsted acidic properties may be used, or two or more types of substances having Lewis acidic properties and/or Brønsted acidic properties may be used in combination, for example (the same applies hereinafter).

In the radical generating catalyst of the third aspect of the present invention, the ammonium may be ammonium represented by the following chemical formula (XI), for example.

$$\begin{bmatrix} & R^{11} & \\ R^{21} - & N^+ & - R^{41} \\ & R^{31} & \end{bmatrix}^X \quad (XI)$$

In the chemical formula (XI), $R^{11}$, $R^{21}$, $R^{31}$, and $R^{41}$ are each a hydrogen atom or an alkyl group (e.g., a straight-chain or branched alkyl group having 1 to 40 carbon atoms) and may each include an ether bond, a ketone (carbonyl group), an ester bond, or an amide bond, or an aromatic ring. $R^{11}$, $R^{21}$, $R^{31}$, and $R^{41}$ may be the same or different from each other. $X^-$ is an anion.

The ammonium represented by the chemical formula (XI) may be ammonium represented by the following chemical formula (XII), for example.

(XII)

In the chemical formula (XII), $R^1$ is an alkyl group having 5 to 40 carbon atoms and may comprise an ether bond, a ketone (carbonyl group), an ester bond, or an amide bond, or an aromatic ring, and $R^{21}$ and $X^-$ are the same as those in the chemical formula (XI).

In the chemical formula (XII), $R^{21}$ may be a methyl group or a benzyl group, for example. In the benzyl group, one or more hydrogen atoms on the benzene ring may or may not be substituted with any substituent. The substituent may be, for example, an alkyl group, an unsaturated aliphatic hydrocarbon group, an aryl group, a heteroaryl group, a halogen, a hydroxy group (—OH), a mercapto group (—SH), or an alkylthio group (—SR, where R is an alkyl group).

The ammonium represented by the chemical formula (XII) may be ammonium represented by the following chemical formula (XIII), for example.

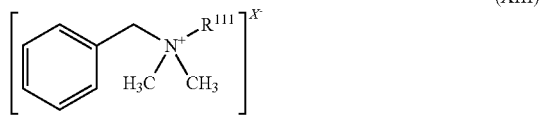

(XIII)

In the chemical formula (XIII), $R^{111}$ and $X^-$ are the same as those in the chemical formula (XII).

The ammonium represented by the chemical formula (XI) may be, for example, at least one selected from the group consisting of benzethonium chloride, benzalkonium chloride, hexadecyltrimethylammonium chloride, tetramethylammonium chloride, ammonium chloride, and tetrabutylammonium chloride. It is particularly preferable that the ammonium represented by the chemical formula (XII) is benzethonium chloride.

Benzethonium chloride ($Bzn^+Cl^-$) can be represented by the following chemical formula, for example. Benzalkonium chloride can be, for example, a compound represented by the chemical formula (XIII) where $R^{111}$ is an alkyl group having 8 to 18 carbon atoms and $X^-$ is a chloride ion.

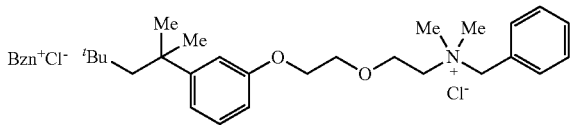

In the chemical formulae (XI), (XII), and (XIII), $X^-$ may be any anion and is not particularly limited. $X^-$ is not limited to a monovalent anion, and may be an anion with any valence, such as a divalent anion or a trivalent anion. When the anion is an anion with a plurality of electric charges, such as a divalent anion or a trivalent anion, the number of molecules of the ammonium (monovalent) in each of the chemical formulae (XI), (XII), and (XIII) is determined by, for example, [the number of molecules of the anion×the valence of the anion] (e.g., when the anion is divalent, the number of molecules of the ammonium (monovalent) is twice the number of molecules of the anion). $X^-$ may be, for example, a halogen ion (a fluoride ion, a chloride ion, a bromide ion, or an iodide ion), an acetate ion, a nitrate ion, or a sulfate ion.

In the third aspect of the present invention, the ammonium may include a plurality of ammonium structures ($N^+$) in one molecule. Further, the ammonium may form a dimer, trimer, or the like by association of a plurality of molecules through a π electron interaction, for example.

In the radical generating catalyst of the third aspect of the present invention, the acid dissociation constant $pK_a$ of the Brønsted acid is, for example, 5 or more. The upper limit of the $pK_a$ is not particularly limited and is, for example, 50 or less.

In the radical generating catalyst of the third aspect of the present invention, the substance having Lewis acidic properties and/or Brønsted acidic properties may be an organic compound (e.g., the above-described organic ammonium or cationic surfactant) or an inorganic substance. The inorganic substance may include one or both of metal ions and nonmetal ions.

The metal ion may include one or both of typical metal ions and transition metal ions. The inorganic substance may be, for example, at least one selected from the group consisting of alkali earth metal ions, rare earth ions, $Sc^{3+}$, $Li^+$, $Fe^{2+}$, $Fe^{3+}$, $Al^{3+}$, silicate ions, and borate ions. Examples of the alkali earth metal ion include ions of calcium, strontium, barium, and radium. More specifically, examples of the alkali earth metal ion include $Ca^{2+}$, $Sr^{2+}$, $Ba^{2+}$, and $Ra^{2+}$. Furthermore the "rare earth metal" is a generic name of a set of seventeen elements, specifically, two elements such as scandium$_{21}$Sc and yttrium$_{39}$Y and fifteen elements (lanthanoids) from lanthanum$_{57}$La to lutetium$_{71}$Lu. Examples of the rare earth ion include corresponding trivalent cations of the seventeen elements.

The Lewis acid (including the counter ion) may be, for example, at least one selected from the group consisting of $CaCl_2$, $MgCl_2$, $FeCl_2$, $FeCl_3$, $AlCl_3$, $AlMeCl_2$, $AlMe_2Cl$, $BF_3$, $BPh_3$, $BMe_3$, $TiCl_4$, $SiF_4$, and $SiCl_4$. It is to be noted that the "Ph" indicates a phenyl group and the "Me" indicates a methyl group.

In the radical generating catalyst of the third aspect of the present invention, the radical generating catalyst can be selected as appropriate depending on the intended use thereof, with consideration given to the reactivity, acidity, safety, etc.

In the drug of the third aspect of the present invention, the radical source may include, for example, at least one selected from the group consisting of halogen ions, hypohalite ions, halite ions, halate ions, and perhalate ions. Particularly preferably, the radical source includes a chlorite ion, for example. The radical source may include, for example, an oxoacid or a salt thereof (e.g., a halogen oxoacid or a salt thereof). Examples of the oxoacid include boric acid, carbonic acid, orthocarbonic acid, carboxylic acid, silicic acid, nitrous acid, nitric acid, phosphorous acid, phosphoric acid, arsenic acid, sulfurous acid, sulfuric acid, sulfonic acid, sulfinic acid, chromic acid, dichromic acid, and permanganic acid. Examples of the halogen oxoacid include: chlorine oxoacids such as hypochlorous acid, chlorous acid, chloric acid, and perchloric acid; bromine oxoacids such as hypobromous acid, bromous acid, bromic acid, and perbromic acid; and iodine oxoacids such as hypoiodous acid, iodous acid, iodic acid, and periodic acid. Among the oxoacids, for example, chlorine oxoacids and salts thereof are preferable, and chlorous acids and salts thereof are more preferable, in terms of the sterilizing effect, risk, safety, etc. One type of radical source may be used, or two or more types of radical sources may be used in combination, for example (the same applies hereinafter).

The radical source may be selected as appropriate depending on the use thereof, with consideration given to the intensity of reactivity of a radical species, etc., for example. For example, hypochlorous acid exhibiting high reactivity or chlorous acid exhibiting somewhat lower reactivity than the hypochlorous acid and allowing a reaction to be controlled more easily may be used as appropriate depending on the intended use.

In the third aspect of the present invention, when the compound (e.g., the organic ammonium) has isomers such as tautomers and stereoisomers (e.g., a geometric isomer, a conformer, and an optical isomer), any isomer can be used in the third aspect of the present invention, unless otherwise stated. When the compound (e.g., the organic ammonium) can form a salt, the salt also can be used in the third aspect of the present invention, unless otherwise stated. The salt may be an acid addition salt, or may be a base addition salt. Moreover, an acid that forms the acid addition salt may be either an inorganic acid or an organic acid, and a base that forms the base addition salt may be either an inorganic base or an organic base. The inorganic acid is not particularly limited, and examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodic acid, perfluoric acid, perchloric acid, perbromic acid, and periodic acid. The organic acid also is not particularly limited, and examples thereof include p-toluenesulfonic acid, methanesulfonic acid, oxalic acid, p-bromobenzenesulfonic acid, carbonic acid, succinic acid, citric acid, benzoic acid, and acetic acid. The inorganic base is not particularly limited, and examples thereof include ammonium hydroxides, alkali metal hydroxides, alkaline-earth metal hydroxides, carbonates, and hydrogencarbonates. More specifically, the inorganic base may be, for example, sodium hydroxide, potassium hydroxide, potassium carbonate, sodium carbonate, sodium hydrogencarbonate, potassium hydrogencarbonate, calcium hydroxide, and calcium carbonate. The organic base also is not particularly limited, and examples thereof include ethanolamine, triethylamine, and tris(hydroxymethyl)aminomethane. The method for producing these salts also is not particularly limited. For example, they can be produced by adding an acid or a base such as described above to the compound as appropriate by a known method.

Moreover, in the third aspect of the present invention, a chain substituent (e.g., an alkyl group, hydrocarbon groups such as an unsaturated aliphatic hydrocarbon group, etc.) may be straight-chain or branched, unless otherwise stated, and the number of carbons thereof is not particularly limited, and may be, for example, 1 to 40, 1 to 32, 1 to 24, 1 to 18, 1 to 12, 1 to 6, or 1 to 2 (at least 2 in the case of an unsaturated hydrocarbon group). Furthermore, in the third aspect of the present invention, as to a cyclic group (e.g., an aryl group, a heteroaryl group, etc.), the number of ring members (the number of atoms that compose a ring) is not particularly limited and may be, for example, 5 to 32, 5 to 24, 6 to 18, 6 to 12, or 6 to 10. When a substituent or the like has isomers, any isomer can be used, unless otherwise stated. For example, in the case of simply describing as a "naphthyl group", it may be a 1-naphthyl group or a 2-naphthyl group.

In the drug of the third aspect of the present invention, the content of the radical source (e.g., oxoacids and the like) is not particularly limited, and is, for example, 0.01 mass ppm or more, 0.05 mass ppm or more, 0.1 mass ppm or more, 1500 mass ppm or less, 1000 mass ppm or less, or 250 mass ppm or less. The amount of the radical source (e.g., oxoacids and the like) mixed in a drug preferably is from 0.01 to 1500 mass ppm, more preferably from 0.05 to 1000 mass ppm, and still more preferably from 0.1 to 250 mass ppm. The concentration of the radical source preferably is low, because it is considered that the safety level increases as the concentration becomes lower. However, if the concentration of the radical source is too low, the sterilizing effect or the like may not be obtained. From the viewpoint of the sterilizing effect and the like, the concentration of the radical source is not particularly limited, and preferably is set as high as possible.

In the drug of the third aspect of the present invention, the content of the radical generating catalyst (e.g., ammonium, a cationic surfactant, or the like) is not particularly limited, and is, for example, 0.01 mass ppm or more, 0.05 mass ppm or more, 0.1 mass ppm or more, 1500 mass ppm or less, 1000 mass ppm or less, 500 mass ppm or less, or 250 mass ppm or less. The amount of the radical generating catalyst (e.g., ammonium, a cationic surfactant, or the like) mixed in the drug preferably is from 0.01 to 1500 mass ppm, more preferably from 0.05 to 1000 mass ppm, still more preferably from 0.05 to 500 mass ppm, and yet more preferably from 0.1 to 250 mass ppm. The concentration of the radical generating catalyst preferably is low, because it is considered that the safety level increases as the concentration becomes lower. However, if the concentration of the radical generating catalyst is too low, the sterilizing effect or the like may not be obtained. From the viewpoint of preventing the risk that the sterilizing effect or the like may not be obtained owing to micelle formation, it is preferable that the concentration of the radical generating catalyst is equal to or lower than the critical micelle concentration.

In the drug of the third aspect of the present invention, the concentration ratio of the radical source and the radical generating catalyst (radical source/radical generating catalyst) in the drug is not particularly limited, and can be set as appropriate.

The drug of the third aspect of the present invention further may contain one or more other substances. Examples of the other substances include water, organic solvents, pH adjusters, and buffers. One type of them may be used, or two or more types of them may be used in combination (the same applies hereinafter). The water is not particularly limited, and preferably is purified water, ion-exchange water, or pure water, for example.

The drug of the third aspect of the present invention preferably contains water and/or an organic solvent. In the third aspect of the present invention, the "solvent" may or may not dissolve the radical generating catalyst of the third aspect of the present invention, the radical source, and the like. For example, after the mixing step, the radical generating catalyst of the third aspect of the present invention and the radical source may each be in a state of being dissolved in the solvent, or may each be in a state of being dispersed or precipitated in the solvent. In the drug of the third aspect of the present invention, it is preferable to use water as a solvent for the radical generating catalyst of the third aspect of the present invention and the radical source from the viewpoint of safety, cost, etc. The organic solvent may be, for example, ketone such as acetone, a nitrile solvent such as acetonitrile, or an alcohol solvent such as ethanol. One type of solvent may be used alone, or two or more types of solvents may be used in combination. The type of the solvent may be selected as appropriate depending on the solubility of the solutes (e.g., the radical generating catalyst of the third aspect of the present invention, the radical source, and the like) etc., for example.

The drug of the third aspect of the present invention can be produced by, for example, mixing the radical source and the radical generating catalyst, and optionally the water and/or organic solvent when necessary. For example, the drug of the third aspect of the present invention can be obtained in manners described in the following examples. It is to be noted, however, that the method for producing the drug of the third aspect of the present invention is not limited thereto. As described above, the drug further may contain one or more substances other than the radical source and the radical generating catalyst.

The drug for use in agriculture and livestock industry according to the fourth aspect of the present invention preferably contains water, for example. However, the drug may not necessarily contain water. The amount of the water mixed (the proportion of the water) in the drug for use in agriculture and livestock industry is not particularly limited. The proportion of the water may be the balance of the drug excluding the other components, for example. The drug for use in agriculture and livestock industry further may or may not contain, as the other substance(s), the pH adjuster, a buffer, and/or the like, for example.

The method of using the drug of the third aspect of the present invention is not particularly limited. For example, the drug of the third aspect of the present invention can be used in the same manners as those for conventional bactericides and the like. Specifically, the drug of the third aspect of the present invention may be sprayed on or applied to a target object, for example. Specifically, for example, when the drug is used for deodorization of a space, the drug can be sprayed in the space. When the drug is use for oral cavity, the drug may be in the form of an aqueous solution so that it can be used for gargling and oral rinsing. When the drug is used for disinfection of a decubitus ulcer, the drug can be applied to an affected area. For an affected area such as a self-destructive wound caused by cancer or a lesion caused by ringworm fungi or the like, absorbent cotton or gauze impregnated with the drug may be applied to the affected area. When the drug is used for hand washing, it may be in the form of an aqueous solution so that it can be rubbed into hands. Medical instruments and the like can be washed with the drug by spraying the drug on them or immersing them in an aqueous solution containing the drug. Further, the drug may be applied to surroundings of beds, tables, doorknobs, and the like for the purpose of sterilization and prevention of infection with bacteria or the like.

(Bactericide)

The drug of the third aspect of the present invention can be used as a bactericide, for example. Although various types of substances have been used as a bactericide conventionally, the sterilizing effects of these substances are not sufficient. Some of them can exhibit enhanced sterilizing effects by increasing their concentrations. However, this poses a problem in safety. A bactericide containing the drug of the third aspect of the present invention can exhibit a sufficient sterilizing effect while the concentration of the drug is low and is highly safe.

(Bactericide for Hand Washing)

The drug of the third aspect of the present invention can be used as a bactericide for hand washing to disinfect hands, for example. The bactericide for hand washing containing the drug of the third aspect of the present invention can exhibit a sufficient sterilizing effect while the concentration of the drug is low and is highly safe.

(Deodorizer)

The drug of the third aspect of the present invention can be used as a deodorizer, for example. Commonly used bactericides, such as ethanol, do not have a deodorizing effect. While chlorine dioxide has a deodorizing effect, the safety level thereof is very low. Some of other commercially available products purport to have sterilizing and deodorizing effects. For example, there are commercially available products purporting to exhibit sterilizing and deodorizing effects by spraying them onto clothes directly or spraying them in rooms, toilets, cars, or the like. Such commercially available products typically contain a quaternary ammonium salt as a sterilizing component. However, a commonly used quaternary ammonium salt is not used in combination with a radical source (e.g., an oxoacid or the like). Thus, in many cases, a sufficient sterilizing effect cannot be obtained unless the quaternary ammonium salt is contained at a high concentration, and this causes a problem of surface tackiness or the like after use. Further, since the quaternary ammonium salt does not have a deodorizing effect, the commercially available products contain a deodorant component as an additional component. While cyclodextrin typically is used as the deodorant component, the cyclodextrin is incapable of decomposing components causing offensive odors. The cyclodextrin merely masks the components causing offensive odors and cannot eliminate the offensive odors themselves. In contrast, the deodorizer containing the drug of the third aspect of the present invention, which has the above-described action mechanism, has a high sterilizing effect, for example, and also, is capable of decomposing substances that cause offensive odors and thus has a high deodorizing effect, for example.

(Antibacterial Agent for Metals)

The drug of the third aspect of the present invention can be used as an antibacterial agent for metals, for example. An antibacterial agent containing the drug of the third aspect of the present invention is highly safe, so that it can be sprayed on or applied to metal products in the kitchen, for example. Also, the antibacterial agent containing the drug of the third aspect of the present invention is less liable to cause corrosion. Thus, even when the antibacterial agent is used on metals, corrosion of the metals is less liable to occur.

(Oral Care Agent)

The drug of the third aspect of the present invention can be used as an oral care agent, for example. An oral care agent containing the drug of the third aspect of the present invention is highly safe and thus suitable for use in the oral cavity.

(Acne Treatment Agent)

The drug of the third aspect of the present invention can be used as an acne treatment agent, for example. An acne treatment agent containing the drug of the third aspect of the present invention is highly safe and thus can be applied to the face.

(Disinfectant for Decubitus Ulcers)

The drug of the third aspect of the present invention can be used as a disinfectant for decubitus ulcers, for example. The disinfectant for decubitus ulcers containing the drug of the third aspect of the present invention is highly safe and thus can be applied to the body.

(Fungicide)

The drug of the third aspect of the present invention can be used as a fungicide for disinfecting an affected part caused by infection with fungi such as ringworm fungi, for example.

(Bactericide for Water Purification)

The drug of the third aspect of the present invention can kill bacteria, such as *Legionella* bacteria, breeding in water in swimming pools and baths, for example. Besides, it does not corrode metals and does not generate gas. Therefore, the bactericide for water purification containing the drug of the third aspect of the present invention can be used safely.

As described above, the drug for use in agriculture and livestock industry according to the fourth aspect of the present invention is highly safe and has a high sterilizing effect. Thus, the drug for use in agriculture and livestock industry can be used as a drug for use in agriculture, a drug for use in livestock industry, or the like, for example. The drug for use in agriculture can be used as, for example, a bactericide for use in agriculture, an antiviral agent for use in agriculture, a deodorizer for use in agriculture, an insecticide for use in agriculture, a repellent for use in agriculture, or a soil conditioner for use in agriculture. The drug for use in livestock industry can be used as, for example, a bactericides for use in livestock industry, an antiviral agent for use in livestock industry, a deodorizer for use in livestock industry, an insecticide for use in livestock industry, a repellent for use in livestock industry, or a soil conditioners for use in livestock industry. The drug for use in agriculture and livestock industry may be applied to one use or two or more uses, for example.

Examples of the agriculture include rice farming and dry-field farming. Examples of the dry-field farming include production of: vegetables such as cucumbers, tomatoes, green onions, Chinese cabbages, and soybeans; tubers and roots, such as potatoes; flowers and ornamental plants, such as chrysanthemums grown with artificial light, *clematis*, and Lady Banks' roses (*Rosa banksiae*); fruits such as strawberries; and fertilizers. Examples of the livestock include industrial animals such as cows, pigs, and chickens.

When the drug for use in agriculture and livestock industry according to the fourth aspect of the present invention is used for the rice farming, the drug for use in agriculture and livestock industry can be used as a bactericide, an insectcide, a repellent, or a soil conditioner, for example. Specifically, for example, by using the drug for use in agriculture and livestock industry during soaking of rice seeds, it is possible to prevent the generation of slime and to reduce the burden of water replacement operations. Further, for example, by using the drug for use in agriculture and livestock industry during seed soaking, stimulation of germination, and seeding, it is possible to prevent rice blast, spot blight, false smut, bakanae disease, and the like. For example, by spreading the drug for use in agriculture and livestock industry over rice fields, it is possible to protect rice from shield bugs, pest insects, and the like. For example, by spreading the drug for use in agriculture and livestock industry during ploughing and irrigation of rice fields, it is possible to improve the soil.

When the drug for use in agriculture and livestock industry according to the fourth aspect of the present invention is used for dry-field farming, the drug for use in agriculture and livestock industry can be used as a bactericide, an antiviral agent, a soil conditioner, or the like, for example. Specifically, for example, by spreading the drug for use in agriculture and livestock industry over leaves of cucumbers, tomatoes, or strawberries, it is possible to prevent powdery mildew, mosaic disease, and the like. For example, by spreading the drug for use in agriculture and livestock industry over leaves of tomatoes, it is possible to prevent gray mold, leaf mold, and the like. For example, by spreading the drug for use in agriculture and livestock industry over leaves of green onions, it is possible to prevent brown leaf rust and the like. For example, by spreading the drug for use in agriculture and livestock industry over leaves of Chinese cabbages, it is possible to prevent root-knot disease and the like. For example, by spreading the drug for use in agriculture and livestock industry over a potato field after being cultivated using a tractor or the like and then cultivating the field again, it is possible to prevent replant failure and the like. For example, by immersing seed potatoes in the drug for use in agriculture and livestock industry, it is possible to disinfect (sterilize) the seed potatoes. For example, by spreading the drug for use in agriculture and livestock industry over leaves of potatoes a plurality of times in a period from germination to harvest of the potatoes, it is possible to prevent common scab and the like. For example, by spreading the drug for use in agriculture and livestock industry over chrysanthemums grown with artificial light, *clematis*, and Lady Banks' roses (*Rosa banksiae*), it is possible to prevent powdery mildew and the like.

When the drug for use in agriculture and livestock industry according to the fourth aspect of the present invention is used for the livestock industry, the drug for use in agriculture and livestock industry can be used as a bactericide, a deodorizer, or the like, for example. Specifically, for example, by using the drug for use in agriculture and livestock industry as a dipping agent for cows, it is possible to prevent mastitis and the like. For example, by using the drug for use in agriculture and livestock industry in a hoof bath for a cow or by applying the drug for use in agriculture and livestock industry to an affected area of a cow infected with a hoof disease, it is possible to prevent or treat the hoof disease and the like. For example, by spraying the drug for use in agriculture and livestock industry on a cow with a sprayer or the like, it is possible to prevent respiratory diseases, foot-and-mouth disease, and the like. For example, by spraying the drug for use in agriculture and livestock industry in a livestock barn or the like for cows, pigs, or chickens with a sprayer or the like, it is possible to deodorize the livestock barn or the like. For example, by using the drug for use in agriculture and livestock industry for hen eggs, it is possible to disinfect (sterilize) the hen eggs.

The drug for use in agriculture and livestock industry according to the fourth aspect of the present invention may be sprayed on, applied to, or spread over a target object, or the target object may be immersed in the drug for use in agriculture and livestock industry, for example. Specifically, when the drug is used to deodorize a space, the drug may be sprayed in the space, for example. When the drug is used for an affected area of a hoof disease or the like, absorbent cotton, gauze, or the like impregnated with the drug may be applied to the affected area, for example. When the drug is used for hand washing, the drug may be in the form of an aqueous solution so that it can be rubbed into hands, for example. Medical instruments and the like can be washed with the drug by spraying the drug on them or immersing them in an aqueous solution containing the drug. When the drug for use in agriculture and livestock industry is used for a machine used in livestock barns, such as an automobile, an agricultural machine, or a forklift, the drug may be sprayed on the machine, or the machine may be washed with the drug, for example. When the drug for use in agriculture and livestock industry is used for deodorization of the above-described industrial animals, the drug may be sprayed with <Disinfectant for Use in Agriculture and Livestock Industry>

A bactericide for use in agriculture and livestock industry according to the fourth aspect of the present invention is characterized in that it contains the drug for use in agriculture and livestock industry according to the fourth aspect of the present invention. The drug for use in agriculture and livestock industry according to the fourth aspect of the present invention can be used as a bactericide, for example. Although various types of substances have been used as a bactericide conventionally, the sterilizing effects of these substances are not sufficient. Some of them can exhibit enhanced sterilizing effects by increasing their concentrations. However, this poses a problem in safety. A bactericide for use in agriculture and livestock industry containing the drug for use in agriculture and livestock industry according to the present invention can exhibit a sufficient sterilizing effect while the concentration of the drug is low and is highly safe.

<Bactericide for Hand Washing for Use in Agriculture and Livestock Industry>

The hand-washing bactericide for use in agriculture and livestock industry according to the fourth aspect of the present invention is characterized in that it contains the drug for use in agriculture and livestock industry according to the fourth aspect of the present invention. The drug for use in agriculture and livestock industry according to the present invention can be used as a bactericide for hand washing for use in agriculture and livestock industry to disinfect hands, for example. The hand-washing bactericide for use in agriculture and livestock industry including the drug for use in agriculture and livestock industry according to the present invention can exhibit a sufficient sterilizing effect while the concentration of the drug is low and is highly safe.

<Deodorizer for Use in Agriculture and Livestock Industry>

The deodorizer for use in agriculture and livestock industry according to the fourth aspect of the present invention is characterized in that it contains the drug for use in agriculture and livestock industry according to the fourth aspect of the present invention. The drug for use in agriculture and livestock industry according to the present invention can be used as a deodorizer for use in agriculture and livestock industry, for example. As a commonly used sterilizing component, a quaternary ammonium salt typically is used. In many cases, a sufficient sterilizing effect cannot be obtained unless the quaternary ammonium salt is contained at a high concentration. This causes a problem in safety. Further, since the quaternary ammonium salt does not have a deodorizing effect, the commercially available products contain a deodorant component as an additional component. While cyclodextrin typically is used as the deodorant component, the cyclodextrin is incapable of decomposing components causing offensive odors. The cyclodextrin merely masks the components causing offensive odors and cannot eliminate the offensive odors themselves. The deodorizer for use in agriculture and livestock industry including the drug for use in agriculture and livestock industry according to the present invention has a high sterilizing effect, and also, is capable of removing substances that cause offensive odors and thus has a high deodorizing effect, for example.

<Fungicide for Use in Agriculture and Livestock Industry>

A fungicide for use in agriculture and livestock industry according to the fourth aspect of the present invention is characterized in that it contains the drug for use in agriculture and livestock industry according to the fourth aspect of the present invention. The fungicide for use in agriculture and livestock industry according to the present invention can be used as a fungicide for disinfecting an affected part caused by infection with fungi such as ringworm fungi, for example.

<Water Purifying Agent for Use in Agriculture and Livestock Industry>

The water purifying agent for use in agriculture and livestock industry according to the fourth aspect of the present invention is characterized in that it contains the drug for use in agriculture and livestock industry according to the fourth aspect of the present invention. The water purifying agent for use in agriculture and livestock industry according to the present invention can kill bacteria, such as *Legionella* bacteria, breeding in water used in agriculture and livestock industry, for example. The drug for use in agriculture and livestock industry according to the fourth aspect of the present invention does not corrode metals and does not generate gas. Therefore, the water purifying agent for use in agriculture and livestock industry containing the drug for use in agriculture and livestock industry according to the fourth aspect of the present invention can be used safely. The water purifying agent for use in agriculture and livestock industry according to the fourth aspect of the present invention can be used to kill bacteria contained in water or to improve quality of water, for example. Thus, the water purifying agent for use in agriculture and livestock industry according to the fourth aspect of the present invention also can be referred to as a bactericide for water for use in agriculture and livestock industry or a water quality improving agent for water for use in agriculture and livestock industry, for example.

<Method of Using Drug for Use in Agriculture and Livestock Industry>

The method of using the drug for use in agriculture and livestock industry according to the fourth aspect of the present invention is characterized in that it includes the step of bringing the drug for use in agriculture and livestock industry according to the present invention into contact with a target object. By the method of using the drug for use in agriculture and livestock industry according to the present invention, it is possible to perform sterilization, deodorization, or the like of the target object, for example.

EXAMPLES

Next, examples of the present invention will be described. It is to be noted, however, that the present invention is by no means limited to the following examples.

Examples of First and Second Aspects of Invention

First, examples of the first and second aspects of the present invention will be described. Examples 1 to 7 of the second aspect of the present invention to be described below all relate to the second aspect of the present invention. Among them, Examples 2, 4, 6 and 7 of the second aspect of the present invention also are examples of the first aspect of the present invention. Examples 1, 3, and 5 of the second aspect of the present invention are described as reference examples of the first aspect of the present invention.

Example 1 of Second Aspect of Invention

In the present example, it was confirmed that efficient dihydroxylation of styrene can be performed by scandium triflate and sodium chlorite. Specifically, by the dihydroxylation of styrene by scandium triflate and chlorite ions ($ClO_2^-$) at ordinary temperature and atmospheric pressure, 1-phenylethane-1,2-diol could be produced efficiently. It was confirmed that the scandium triflate working as a strong Lewis acid generates chlorine dioxide radicals ($ClO_2\cdot$) from the chlorite ions ($ClO_2^-$) and increases the reactivity of the chlorine dioxide radicals ($ClO_2\cdot$).

Oxidization of an olefin to a 1,2-diol is an important industrial process for producing precursors of various types of chemical substances such as resins, pharmaceutical agents, dyes, insecticides, and perfume compounds in the fields of fine chemicals and speciality chemicals. Several methods for converting olefins to corresponding epoxides and alcohols by oxidization using inorganic metal oxo complexes and metallic oxides having heavy atoms have been reported. High-valent $Os^{VIII}O_4$ is an effective and selective reagent for oxidizing an olefin to a 1,2-diol (References, etc. 1 to 8). However, the toxicity, sublimation property, and waste of the osmium compound cause serious problems. Sodium chlorite ($NaClO_2$) is a non-toxic inexpensive oxidizing reagent and has been used as a precursor of a chlorine dioxide radical ($ClO_2\cdot$) (References, etc. 9 to 12 [the same as Non Patent Literatures 1 to 4]). $ClO_2\cdot$ is known as a reactive stable radical. $ClO_2\cdot$, however, is an explosive gas which is yellow at room temperature. $ClO_2\cdot$ can be experimentally prepared by oxidization of $NaClO_2$ by $Cl_2$ and reaction of chloric acid potassium ($KClO_3$) and oxalic acid (Reference, etc. 13). These methods cause serious problems such as the toxicity of $Cl_2$ and the explosivity of $ClO_3^-$. There has been an attempt on epoxidation of an olefin using $NaClO_2$ as a precursor of $ClO_2\cdot$. However, because the oxidization ability of $ClO_2\cdot$ was not strong enough to oxidize an olefin to a diol in the absence of an acid, a 1,2-diol product could not be obtained (References, etc. 14 to 17). The activation of $Cl=O$ double bond of $ClO_2\cdot$ is a key for selectively dihydroxylating an olefin in one step.

The present example reports an efficient synthesis method of a dihydroxylated product of styrene at ordinary temperature and atmospheric pressure by the activation of $ClO_2\cdot$ using scandium triflate [$Sc(OTf)_3$] as a Lewis acid (Reference, etc. 18). The mechanism of dihydroxylation was disclosed on the basis of the detection of a radical intermediate by the EPR and UV-Vis absorption spectroscopy.

Figure 6:
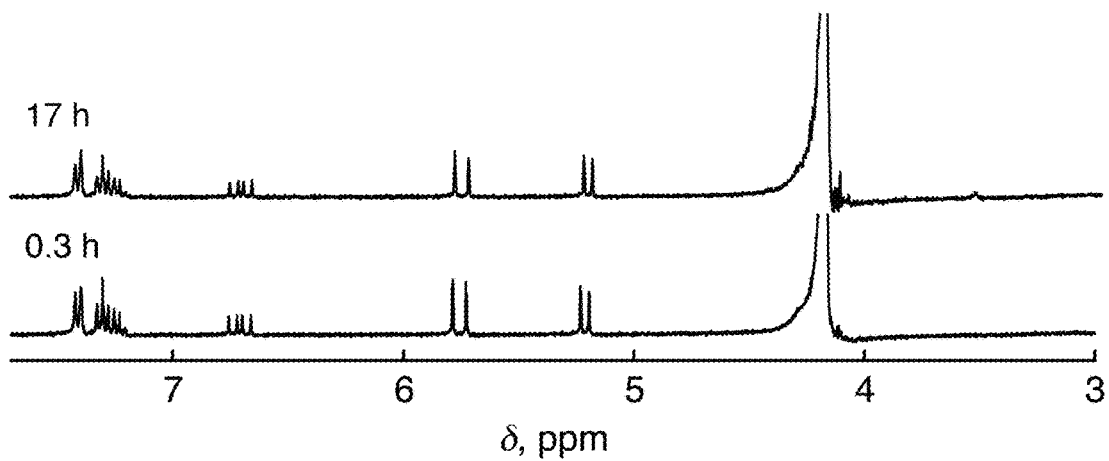
FIG. 6 is a spectral diagram showing the result of tracing the reaction of styrene (2.0 mM) by $NaClO_2$ (20 mM) in an aqueous MeCN solution ($MeCN/H_2O$ 1:1 v/v) at room temperature (25° C.) utilizing $^1HNMR$.
Figure 7:
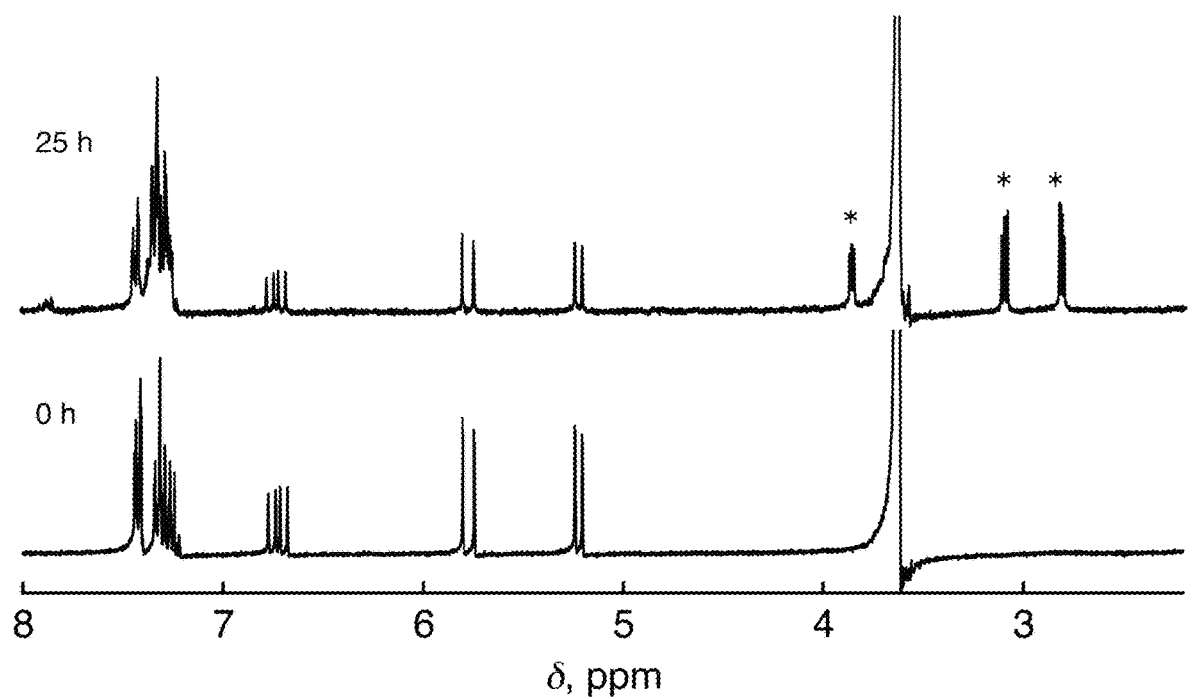
FIG. 7 shows $^1HNMR$ spectra of $CD_3CN/D_2O$ (4:1 v/v) that contains styrene (66 mM) and $NaClO_2$ (200 mM) at 60° C. (333 K) collected 0 hours and 25 hours after mixing. The mark "*" indicates the peak derived from styrene oxide.
Figure 8:
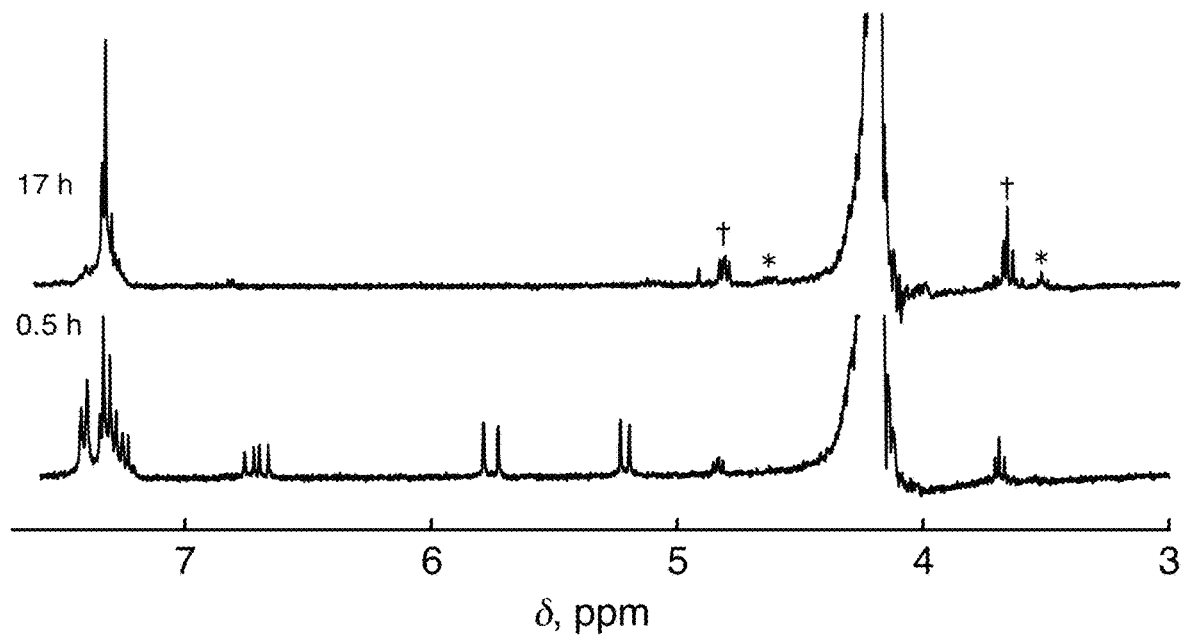
FIG. 8 shows $^1HNMR$ spectra of $CD_3CN/D_2O$ (1:1 v/v) that contains styrene (2.0 mM), $NaClO_2$ (20 mM), and $Sc(OTf)_3$ (30 mM) at 25° C. collected 0.6 hours and 17 hours after mixing. The mark "*" and the mark "\" indicate the peak derived from 1-phenylethane-1,2-diol and the peak derived from 2-chloro-1-phenylethanol, respectively.
Figure 9:
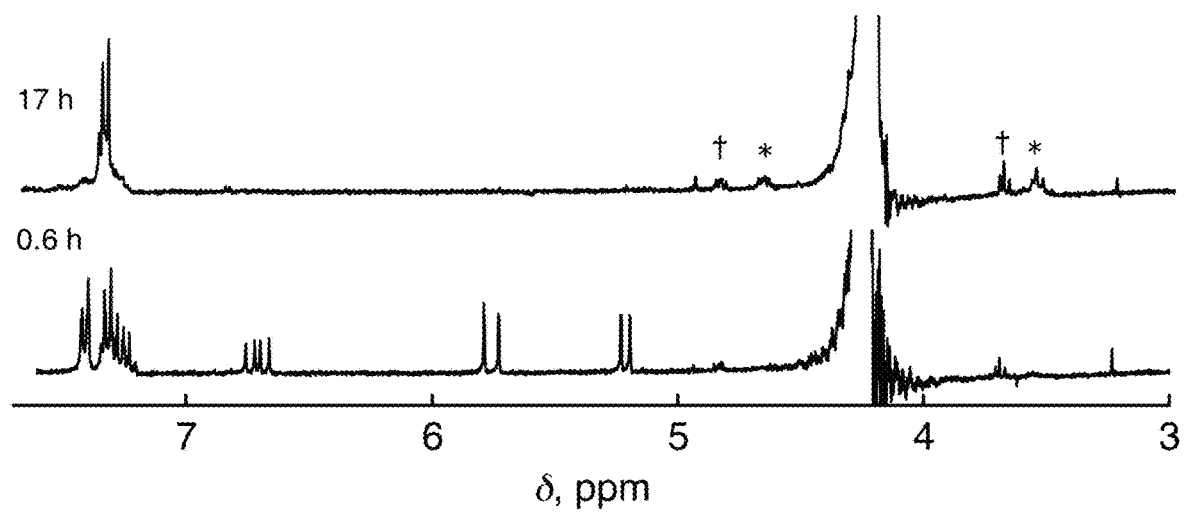
FIG. 9 shows $^1HNMR$ spectra of $CD_3CN/D_2O$ (1:1 v/v) that contains styrene (2.0 mM), $NaClO_2$ (20 mM), and $CF_3COOD$ (30 mM) collected 0.5 hours and 17 hours after mixing. The mark "*" and the mark "\" indicate the peak derived from 1-phenylethane-1,2-diol and the peak derived from 2-chloro-1-phenylethanol, respectively.
Figure 19:
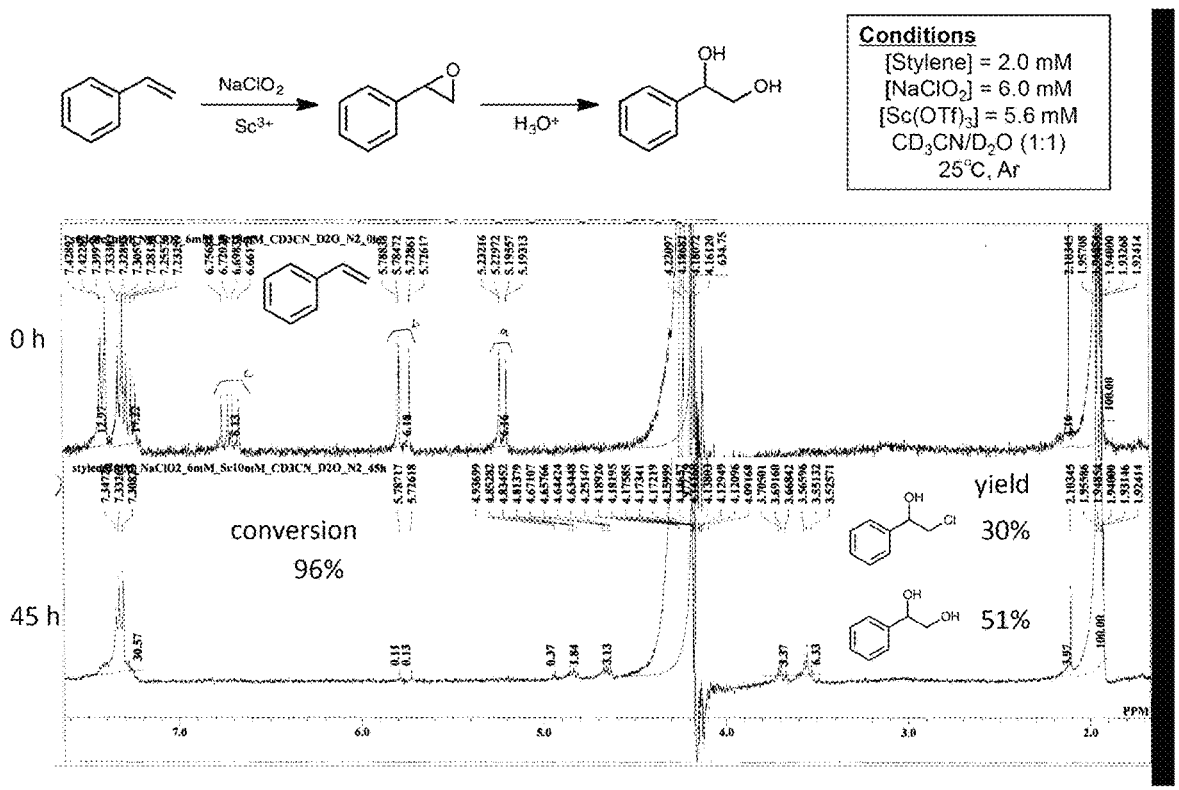
FIG. 19 shows $^1HNMR$ spectra of $CD_3CN/D_2O$ (1:1 v/v) that contains styrene (2.0 mM), $NaClO_2$ (6.0 mM), and $Sc(OTf)_3$ (5.6 mM) at 25° C. in the Ar atmosphere collected 0 hours and 45 hours after mixing.

In the reaction of styrene (2.0 mM) by $NaClO_2$ (20 mM) in an aqueous MeCN solution (MeCN/$H_2O$ 1:1 v/v) at room temperature (25° C.), dihydroxylation of the styrene was not caused (see FIG. 6). FIG. 6 shows the results obtained by performing the above-described reaction using a $^1$HNMR spectrum measurement solvent $CD_3CN/D_2O$ (1:1 v/v) as MeCN/$H_2O$ and tracing the reaction utilizing $^1$HNMR. FIG. 6 shows the $^1$HNMR spectra of $CD_3CN/D_2O$ (1:1 v/v) collected 0.3 hours and 17 hours after the start of the reaction. When the temperature was increased to 333 K, a dihydroxylated product was not formed but epoxidation was caused (FIG. 7) (References, etc. 14 and 19). FIG. 7 shows the $^1$HNMR spectra of $CD_3CN/D_2O$ (4:1 v/v) that contains styrene (66 mM) and $NaClO_2$ (200 mM) at 60° C. (333 K) collected 0 hours and 25 hours after mixing. The mark "*" indicates the peak derived from styrene oxide. In contrast, in the case where $CF_3COOH$ (30 mM) as a Brønsted acid was added as an additive, an epoxide was not formed at all 17 hours after mixing, instead, 1-phenylethane-1,2 diol (1) and 2-chloro-1-phenylethanol (2) were produced at the yield of 15% and 69%, respectively [reaction formula (1)]. They were measured utilizing the $^1$HNMR spectrum (FIG. 8) (Reference, etc. 20). FIG. 8 shows the $^1$HNMR spectra of $CD_3CN/D_2O$ (1:1 v/v) that contains styrene (2.0 mM), $NaClO_2$ (20 mM), and $Sc(OTf)_3$ (30 mM) at 25° C. collected 0.6 hours and 17 hours after mixing. The mark "*" and the mark "\" indicate the peak derived from 1-phenylethane-1, 2-diol and the peak derived from 2-chloro-1-phenylethanol, respectively. When $Sc(OTf)_3$ (30 mM), which is a strong Lewis acid, was used instead of $CF_3COOH$, the yield of diol (1) increased remarkably to 51% [see the following reaction formula (1)] (FIG. 19) (Reference, etc. 21). FIG. 9 shows the $^1$HNMR spectra of $CD_3CN/D_2O$ (1:1 v/v) that contains styrene (2.0 mM), $NaClO_2$ (20 mM), and $CF_3COOD$ (30 mM) collected 0.5 hours and 17 hours after mixing. The mark "*" and the mark "\" indicate the peak derived from 1-phenylethane-1,2-diol and the peak derived from 2-chloro-1-phenylethanol, respectively.

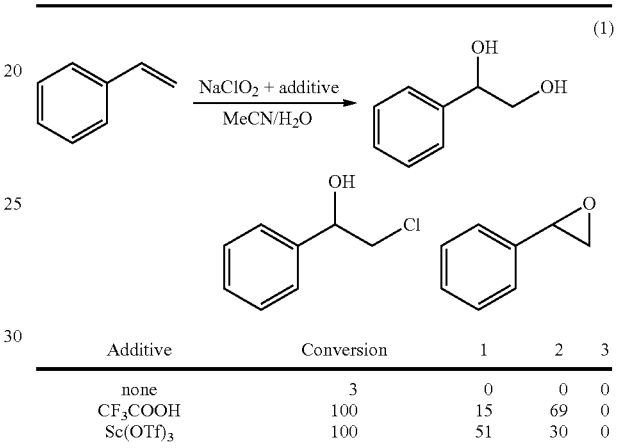

(1)

| Additive | Conversion | 1 | 2 | 3 |
|---|---|---|---|---|
| none | 3 | 0 | 0 | 0 |
| $CF_3COOH$ | 100 | 15 | 69 | 0 |
| $Sc(OTf)_3$ | 100 | 51 | 30 | 0 |

Figures 2A, 2B:
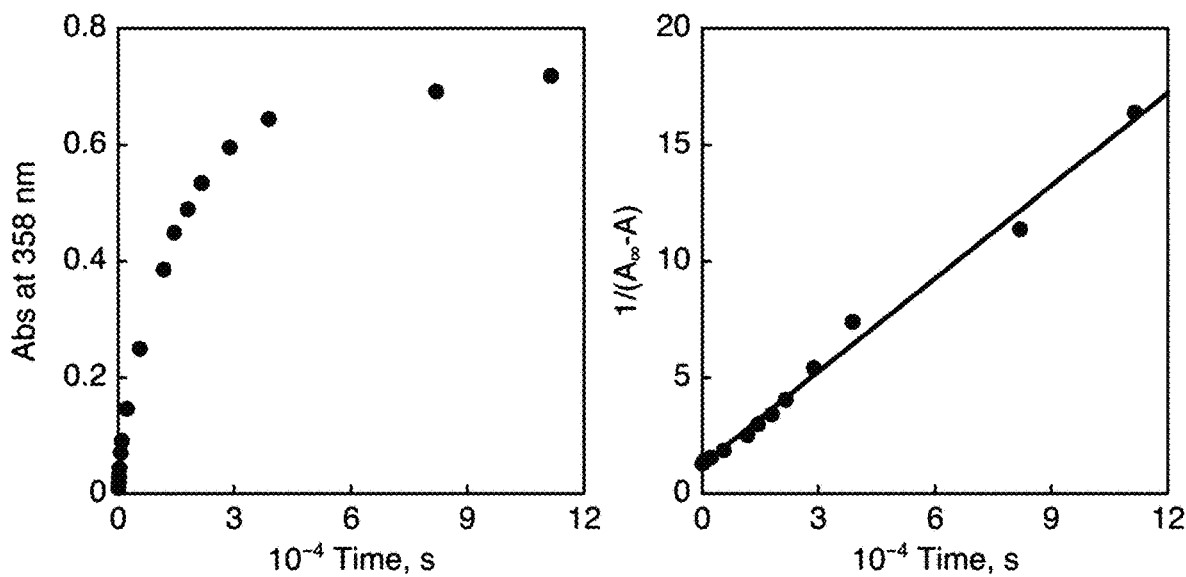
FIG. 2A shows a time profile of UV-Vis absorption at 358 nm in formation of $Sc^{3+}(ClO_2\cdot)$ by a reaction between $Sc(OTf)_3$ (10 mM) and $NaClO_2$ (5.0 mM) in an aqueous solution (0.20 M acetate buffer having a pH of 2.9) at 298 K.
FIG. 2B shows a secondary plot.

The UV-Vis absorption spectroscopy was adopted for clarifying the reaction mechanism and the detection of a reactive intermediate. As shown in FIG. 1, $NaClO_2$ showed the absorption band at 260 nm in an aqueous solution. The absorption band was quenched by adding $Sc(OTf)_3$ (10 mM), and in accordance with this, a new absorption band was increased at 358 nm, and it was identified (assigned) that this absorption band was based on $ClO_2\cdot$ (References, etc. 22, 23). Also in the presence of $CF_3COOH$, a similar change of the absorption spectrum was measured (Reference, etc. 24). FIG. 1 shows the change of occurrence of the absorption band at 358 nm with time. FIG. 1 shows the ultraviolet-visible absorption spectrum of $NaClO_2$ (5.0 mM) collected 0, 4, and 16 hours after mixing with $Sc(OTf)_3$ (10 mM) in an aqueous solution at 298 K. In FIG. 1, the horizontal axis indicates the wavelength (nm) and the vertical axis indicates the absorbance. FIG. 2A shows a time profile of UV-Vis absorption at 358 nm in the same reaction as shown in FIG. 1 (formation of $Sc^{3+}(ClO_2\cdot)$) by a reaction between $Sc(OTf)_3$ (10 mM) and $NaClO_2$ (5.0 mM) in an aqueous solution (0.20 M acetate buffer having a pH of 2.9) at 298 K). In FIG. 2A, the horizontal axis indicates the time (second) and the vertical axis indicates the absorbance at 358 nm. FIG. 2B shows the secondary plot of the measurement result of FIG. 2A. The time profile (FIG. 2A) meets the secondary plot (FIG. 2B) well. In generation of $ClO_2\cdot$ using $Sc(OTf)_3$, two molecules of $ClO_2^-$ are involved in the rate-determining step (see below). The rate constant of the two molecules was determined as 0.16 $M^{-1}s^{-1}$ based on the slope of the straight line.

Figure 3A:
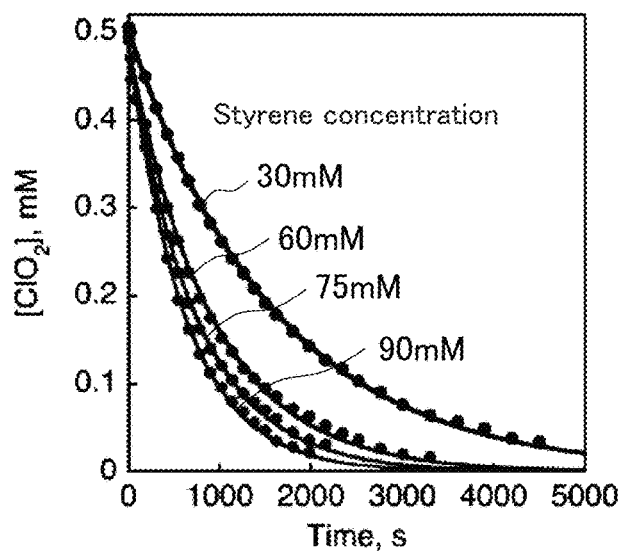
FIG. 3A shows a time profile of UV-Vis absorption at 358 nm in consumption of $Sc^{3+}(ClO_2.)$ in the presence of styrene (30 to 90 mM) in a $MeCN/H_2O$ (1:1 v/v) solution at 298 K.
Figure 3B:
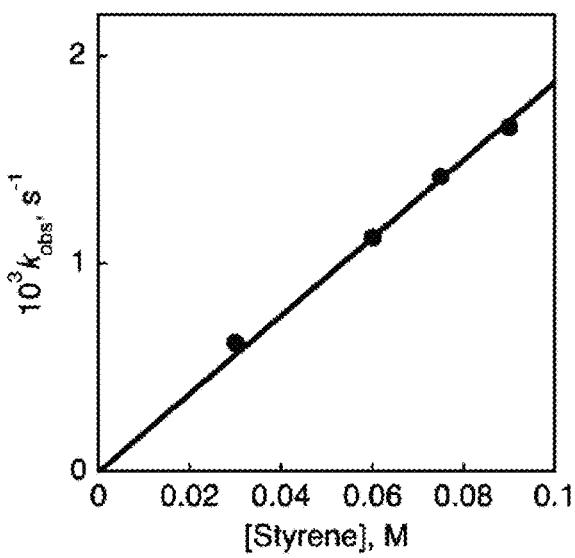
FIG. 3B shows a pseudo first-order rate-styrene concentration plot.
Figure 4:
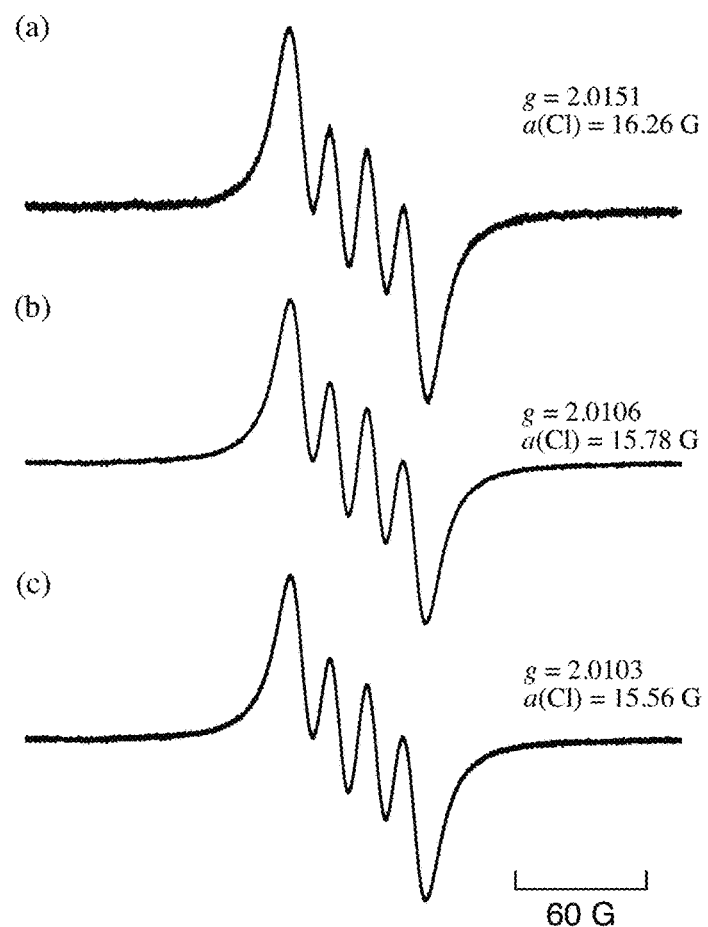
FIG. 4 shows EPR spectra of MeCN solutions measured at 298 K.

In the absence of a substrate, no decay of the absorbance at 358 nm based on $ClO_2\cdot$ generated from $NaClO_2$ using Sc(OTf)$_3$ was observed in MeCN at 298 K. FIG. 3A shows the time profile of UV-Vis absorption at 358 nm in consumption of Sc$^{3+}$ (ClO$_2$.) in the presence of styrene (30 to 90 mM) in a MeCN/H$_2$O (1:1 v/v) solution at 298 K. In FIG. 3A, the horizontal axis indicates the time (second), and the vertical axis indicates the ClO$_2$. concentration. FIG. 3B shows the pseudo first-order rate-styrene concentration plot. In the presence of an excessive amount of styrene, the rate of decay was in accordance with the pseudo first order (FIG. 3B). The pseudo first-order rate ($k_{obs}$) observed on the increase in dihydroxyl was increased linearly with the increase in a styrene concentration (FIG. 3B). The two-molecule rate constant of the consumption of ClO$_2$. and styrene was determined as $1.9 \times 10^{-2}$ M$^{-1}$s$^{-1}$ (Reference, etc. 25). For clarifying the radical structure, electronic paramagnetic resonance (EPR) was performed. Pure ClO$_2$. was prepared by refluxing a MeCN solution containing NaClO$_2$ at 353 K for 1 hour. The EPR spectrum of the thus-obtained pure ClO$_2$. was measured after being cooled to 298 K. As a result, a distinctive isotropic signal was observed with g=2.0151 (+0.0002) together with four hyperfine lines derived from an unpaired electron of a Cl nucleus (I=3/2 in $^{35}$Cl and $^{37}$Cl, each having the same type of magnetic moment of 0.821 and 0.683 ((a) of FIG. 4) (Reference, etc. 26). The G value was remarkably changed by addition of CF$_3$COOH (g=2.0106) and Sc(OTf)$_3$ (g=2.0103) ((b) and (c) of FIG. 4). The hyperfine binding constant of ClO$_2$. was decreased in the presence of CF$_3$COOH (15.78 G) and Sc(OTf)$_3$ (15.56 G) (a(Cl)=16.26 G) (Reference, etc. 27). This shows that proton and Sc$^{3+}$ bind to ClO$_2$. to form H+ClO$_2$. and Sc$^{3+}$ClO$_2$. as reaction intermediates for strongly dihydroxylating styrene (Reference, etc. 28).

Figure 5:
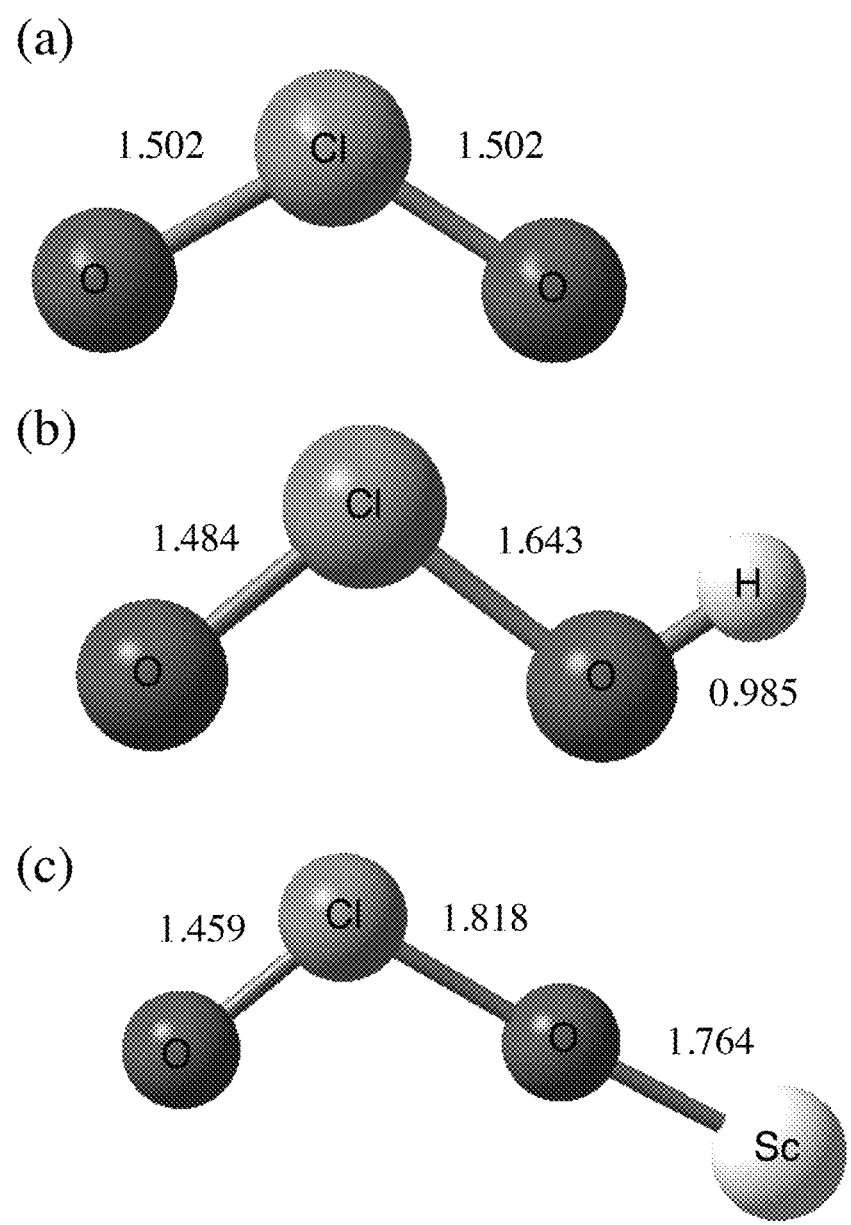
FIG. 5 shows bond lengths (Å) of optimized structures calculated by DFT at the level of CAM-B3LYP/6-311+G(d, p).
Figure 10:
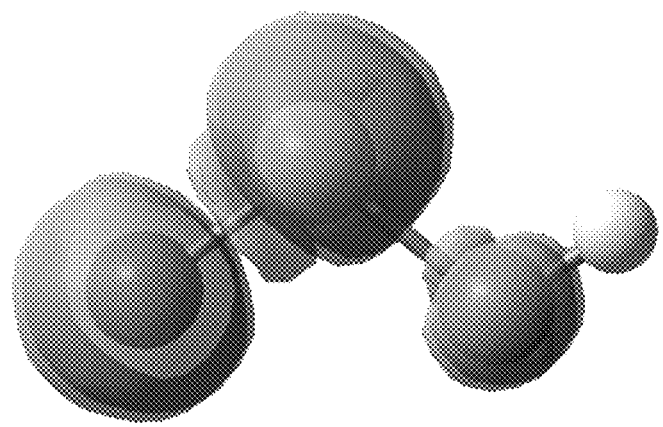
FIG. 10 is a diagram showing spin distributions calculated by DFT at the level of CAM-B3LYP/6-311+G(d, p).
Figure 10:
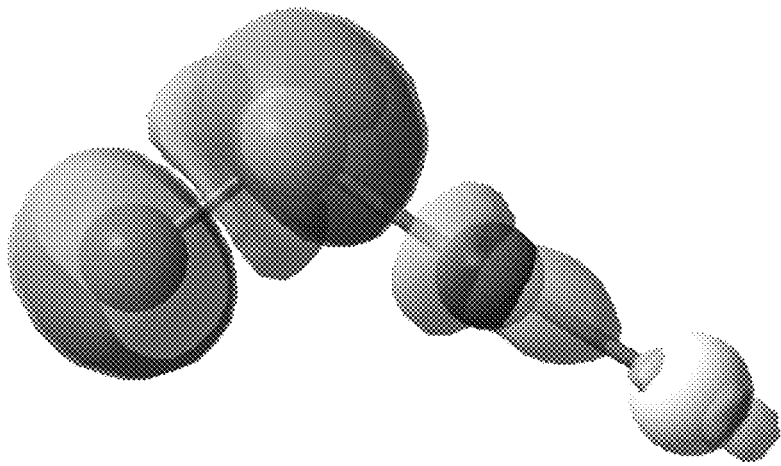

As shown in FIG. 5, properties of ClO$_2$., H$^+$ClO$_2$., and Sc$^{3+}$ClO$_2$. were calculated on the basis of the density functional theory (DFT), and the reaction mechanism for dihydroxylation was predicted. The optimization of a structure was performed by the theoretical calculation at the level of DFT CAM-B3LYP/6-311+G(d, p). FIG. 5 shows the bond lengths (Å) of the DFT-optimized structures obtained by the theoretical calculation at the level of CAM-B3LYP/6-311+G(d, p). In FIG. 5, (a) shows the result obtained regarding ClO$_2$.; (b) shows the result obtained regarding H$^+$ClO$_2$.; and (c) shows the result obtained regarding Sc$^{3+}$ClO$_2$. The bond length of the Cl—O double bond of ClO$_2$. was calculated as 1.502 Å ((a) of FIG. 5). The bond length of the Cl—O double bond of H$^+$ClO$_2$. was calculated as 1.643 Å ((b) of FIG. 5). (c) of FIG. 5 shows that, as compared to ClO$_2$., the bond strength of Sc$^{3+}$ClO$_2$. is also remarkably weakened (Cl—O: 1.818 Å). There is a possibility that the cleavage of the Cl—O bond may affect advantageously on generation of ClO. as a strong oxidizing agent in the presence of a substrate. FIG. 10 shows spin distributions obtained by the theoretical calculation at the level of CAM-B3LYP/6-311+G(d, p). In FIG. 10, (a) shows the spin distribution of H$^+$ClO$_2$. and (b) shows the spin distribution of Sc$^{3+}$ClO$_2$.

On the basis of the above-described results, the dihydroxylation mechanism of styrene by ClO$_2$. is shown in the following reaction formulae (2) to (5) and scheme 1. The disproportionation reaction of NaClO$_2$ is caused in the presence of H$^+$ or Sc$^{3+}$, thereby forming ClO$^-$ and ClO$_3^-$ [reaction formula (2)] (Reference, etc. 29). ClO$^-$ easily reacts with ClO$_2^-$ and protons, thereby generating Cl$_2$O$_2$ [reaction formula (3)]. Subsequently, Cl$_2$O$_2$ is reduced by ClO$_2^-$, thereby generating a reactive species ClO$_2$. [reaction formula (4)]. An overall stoichiometry is given by the reaction formula (5). ClO$_2$. is activated by binding to acids such as H$^+$ and Sc$^{3+}$. When ClO$_2$ binds to H$^+$, on the basis of the DFT calculation (see above), the Cl—O bond is not cleaved. The oxidization of styrene by H$^+$ proceeds by addition of ClO$_2$. to the styrene double bond. In contrast, the dihydroxylation of styrene by Sc$^{3+}$ is caused, as shown in scheme 1, by addition of ClO. and Sc$^{3+}$O. generated by homolytic fission of Sc$^{3+}$Cl—O bond of a Sc$^{3+}$ClO$_2$. complex to the styrene double bond. Subsequently, a scandium complex is hydrolyzed for obtaining a diol and Sc$^{3+}$ ClO. as end products (scheme 1). Sc$^{3+}$ClO. can be reused by adding a large excessive amount of ClO$_2^-$ to cause Sc$^{3+}$ ClO$_2$. to be formed through oxidization. Also, ClO$^-$ can be regenerated by ClO$_2^-$ as shown in reaction formula (2). Addition of ClO. formed by cleaving the Cl—O bond of Sc$^{3+}$ClO$_2$. to β carbon of styrene gave two isomers. When the β carbon-ClO bond is formed, as shown in scheme 1, a chlorine compound was obtained as a minor end product.

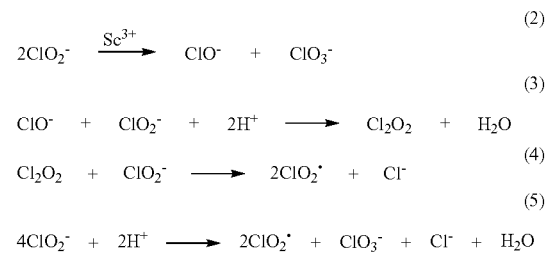

$$2ClO_2^- \xrightarrow{Sc^{3+}} ClO^- + ClO_3^- \quad (2)$$

$$ClO^- + ClO_2^- + 2H^+ \longrightarrow Cl_2O_2 + H_2O \quad (3)$$

$$Cl_2O_2 + ClO_2^- \longrightarrow 2ClO_2^\cdot + Cl^- \quad (4)$$

$$4ClO_2^- + 2H^+ \longrightarrow 2ClO_2^\cdot + ClO_3^- + Cl^- + H_2O \quad (5)$$

Scheme 1

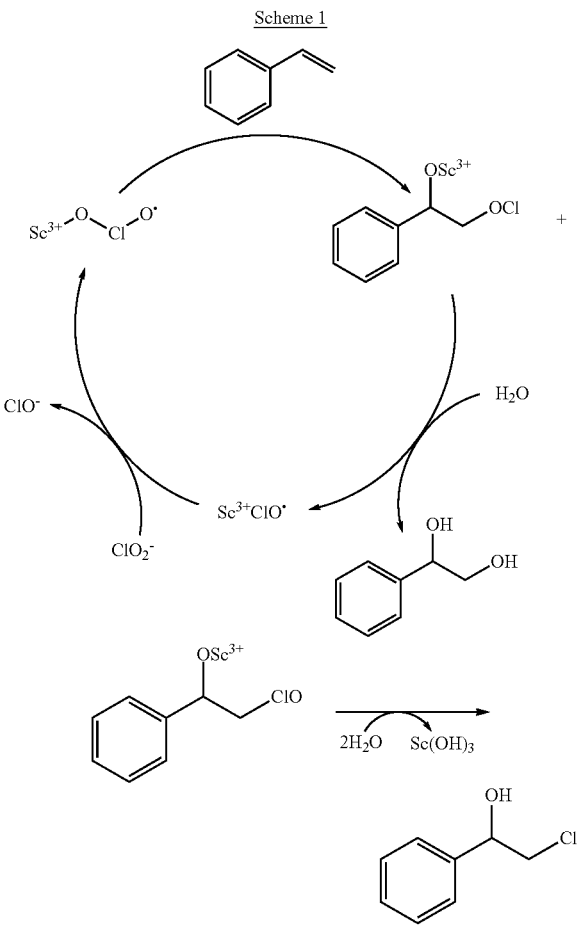

As described above, it was confirmed by the present example that $ClO_2$. is an effective dihydroxylation reagent for styrene as a Lewis acid in the presence of $Sc^{3+}$. The present invention can provide a unique dihydroxylation pathway of an olefin without causing hazardous wastes such as heavy metals.

REFERENCES, ETC

1. M. Schroeder, Chem. Rev., 1980, 80, 187-213.
2. (a) E. N. Jacobsen, I. Marko, W. S. Mungall, G. Schroeder and K. B. Sharpless, J. Am. Chem. Soc., 1988, 110, 1968-1970; and (b) S. G. Hentges and K. B. Sharpless, J. Am. Chem. Soc., 1980, 102, 4263-4265.
3. W. Yu, Y Mei, Y Kang, Z. Hua and Z. Jin, Org. Lett., 2004, 6, 3217-3219.
4. (a) A. J. DelMonte, J. Haller, K. N. Houk, K. B. Sharpless, D. A. Singleton, T. Strassner, and A. A. Thomas, J. Am. Chem. Soc., 1997, 119, 9907-9908; and (b) J. S. M. Wai, I. Marko, J. S. Svendsen, M. G. Finn, E. N. Jacobsen and K. B. Sharpless, J. Am. Chem. Soc., 1989, 111, 1123-1125.
5. (a) S. Kobayashi, M. Endo and S. Nagayama, J. Am. Chem. Soc., 1999, 121, 11229-11230; and (b) S. Kobayashi, T. Ishida and R. Akiyama, Org. Lett., 2001, 3, 2649-2652.
6. H. C. Kolb, P. G. Andersson and K. B. Sharpless, J. Am. Chem. Soc., 1994, 116, 1278-1291.
7. E. J. Corey and M. C. Noe, J. Am. Chem. Soc., 1996, 118, 11038-11053.
8. S. Y Jonsson, K. Faernegrdh and J.-E. Baeckvall, J. Am. Chem. Soc., 2001, 123, 1365-1371.
9. H. Dodgen and H. Taube, J. Am. Chem. Soc., 1949, 71, 2501-2504.
10. J. K. Leigh, J. Rajput, and D. E. Richardson, Inorg. Chem., 2014, 53, 6715-6727.
11. C. L. Latshaw, Tappi J., 1994, 163-166.
12. (a) J. J. Leddy, in Riegel's Handbook of Industrial Chemistry, 8th edn. Ed., J. A. Kent, Van Nostrand Reinhold Co. Inc, New York, 1983, pp. 212-235; and (b) I. Fabian, Coord. Chem. Rev., 2001, 216-217, 449-472.
13. M. J. Masschelen, J. Am. Works Assoc., 1984, 76, 70-76.
14. X.-L. Geng, Z. Wang, X.-Q. Li, and C. Zhang J. Org. Chem., 2005, 70, 9610-9613.
15. A. Jangam and D. E. Richardson, Tetrahedron Lett., 2010, 51, 6481-6484.
16. J. J. Kolar and B. O. Lindgren, Acta Chem. Scand. B, 1982, 36, 599-605.
17. B. O. Lindgren, T. Nilsson, Acta Chem. Scand. B, 1974, 28, 847-852.
18. (a) S. Fukuzumi and K. Ohkubo, J. Am. Chem. Soc., 2002, 124, 10270-10271; and (b) S. Fukuzumi and K. Ohkubo, Chem.-Eur. J., 2000, 6, 4532-4535.
19. Epoxidation of styrene (66 mM) by $NaClO_2$ (200 mM) was checked in a $MeCN/H_2O$ mixture solution (4:1 v/v) at 333 K (Reference, etc. 14). The yield of styrene oxide was 44% and the conversion ratio of styrene was 61%.
20. E. V. Bakhmutova-Albert, D. W. Margerum, J. G. Auer and B. M. Applegate, Inorg. Chem., 2008, 47, 2205-2211.
21. As a result of measurement utilizing $^1$HNMR, styrene epoxide as an intermediate in reaction by $CF_3COOH$ or $Sc(OTf)_3$ was not observed.
22. C. Rav-Acha, E. Choushen (Goldstein) and S. Sarel, Helv. Chim. Acta, 1986, 69, 1728-1733.
23. There is a possibility that $ClO_2$. generated from acetic anhydride and $NaClO_2$ (Reference, etc. 22) is in the protonated form ($H^+ClO_2$.) in a $ClO_2$. aqueous solution.
24. W. Masschelein, Ind. Eng. Chem. Prod. Res. Devel., 1967, 6, 137-142.
25. This numerical value is slightly greater than the value of the conversion of styrene to epoxide by $ClO_2$. ($1.17 \times 10^{-2}$ $M^{-1}s^{-1}$) (Reference, etc. 10).
26. (a) T. Ozawa and T. Kwan, Chem. Pharm. Bull., 1983, 31, 2864-2867; and (b) T. Ozawa, T. Trends Org. Chem., 1991, 2, 51-58.
27. The calculated values of the spin distribution of $Sc^{3+}$ $ClO_2$. and $H^+ClO_2$. are shown in FIG. 10. According to this, each of Sc and H nuclei does not show a spin density. This means that the EPR spectrum does not show the hyperfine splitting derived from Sc ($I=7/2$) or H ($I=1/2$).
28. As to the bond between $Sc^{3+}$ and an oxo group of a metal oxo complex, see the following references:
(a) J. Chen, X. Wu, K. M. Davis, Y-M. Lee, M. S. Seo, K.-B. Cho, H. Yoon, Y J. Park, S. Fukuzumi, Y N. Pushkar and W. Nam, J. Am. Chem. Soc., 2013, 135, 6388-6391; (b) H. Yoon, Y-M. Lee, X. Wu, K.-B. Cho, Y N. Pushkar, W. Nam and S. Fukuzumi, J. Am. Chem. Soc., 2013, 135, 9186-9194; and (c) S. Fukuzumi, K. Ohkubo, Y-M. Lee and W. Nam, Chem.-Eur. J., 2015, 21, 17548-17559.
29. As to the disproportionation of a neutral radical by $Sc^{3+}$, see the following reference: I. Nakanishi, T. Kawashima, K. Ohkubo, T. Waki, Y Uto, T. Kamada, T. Ozawa, K. Matsumoto and S. Fukuzumi, S. Chem. Commun., 2014, 50, 814-816.

Example 2 of Second Aspect of Invention

In the present example, an oxygen reduction reaction was activated by benzethonium chloride. Research and development of Lewis acids have been carried out widely in various organic synthesis reactions. In most of the researches, a metal ion or a metal complex was used as a Lewis acid site, and the ligand design around the Lewis acid site was the main focus of the researches. In the present example, benzethonium chloride was used as an ammonium derivative having strong Lewis acidic properties, and whether the benzethonium chloride is widely useful in an oxygenation reaction of an aromatic organic compound using sodium chlorite was examined.

Figure 11:
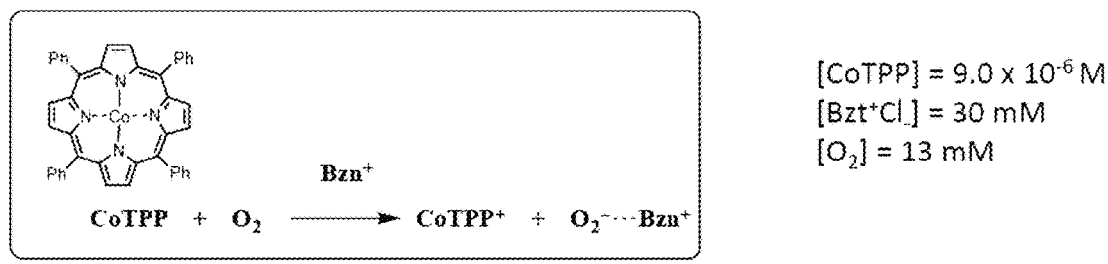
In FIG. 11, (a) is a graph showing the time course of an ultraviolet-visible absorption spectrum of a solution obtained by adding benzethonium chloride ($Bzn^+$) to an oxygen saturated solution of a cobalt (II) tetraphenylporphyrin complex Co(II)TPP ([CoTPP]=$9.0 \times 10^{-6}$ M, [$O_2$]=13 mM) ([$Bzn^+Cl^-$]=30 mM); and (b) is a graph showing the time course of an increase in the absorption band at 433 nm shown in the graph (a).
Figure 11:
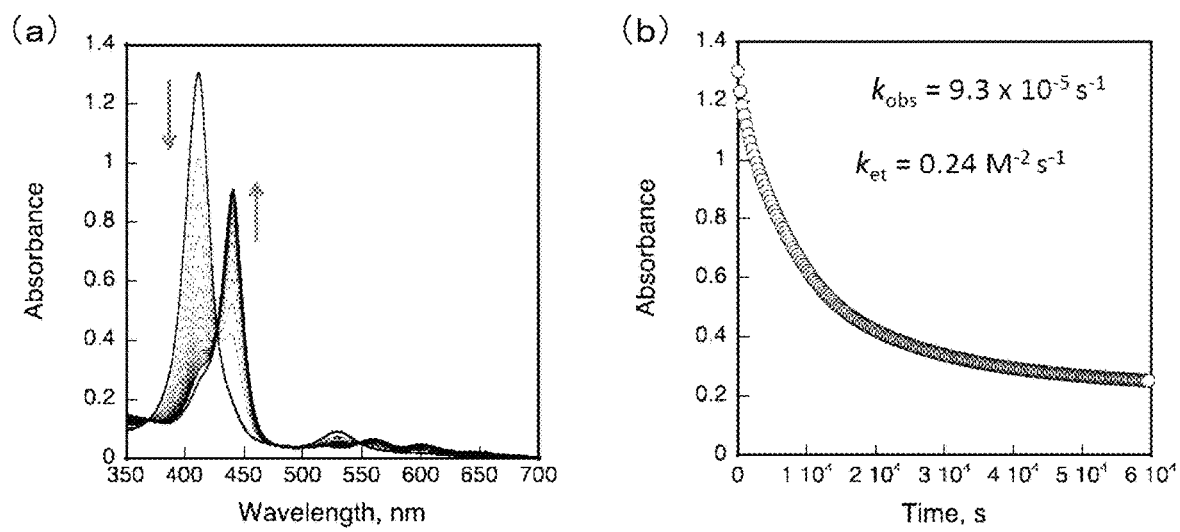
Figure 21:
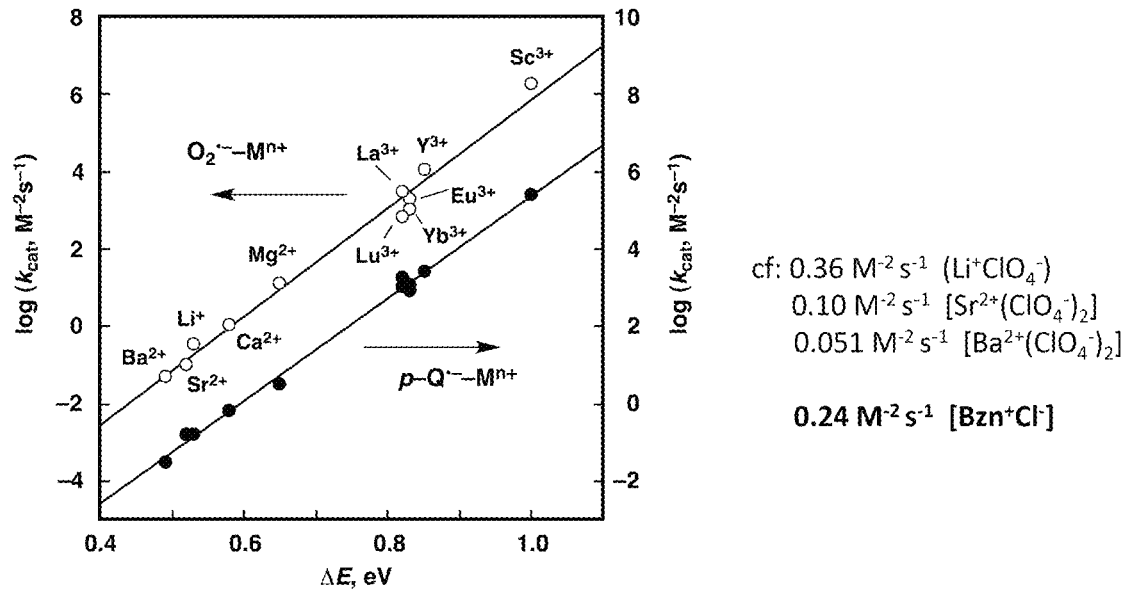
FIG. 21 is a graph showing the Lewis acidities of benzethonium chloride [$Bzn^+Cl^-$] and various metal complexes.

In acetonitrile, electron transfer does not proceed at all between cobalt (II) tetraphenylporphyrin complex Co(II)TPP (TPP=5,10,15,20-tetraphenylporphyrin) ($E_{ox}=0.35V$ vs SCE) and molecular oxygen ($E_{red}=-0.86$ V vs SCE). However, when benzethonium chloride ($Bzn^+$) was added to this oxygen saturated solution ($[CoTPP]=9.0 \times 10^{-6}$ M, $[O_2]=13$ mM) ($[Bzn^+Cl^-]=30$ mM), accompanying decay of the absorption band derived from Co(II)TPP at 411 nm, an increase in absorption band characteristic of Co(III)TPP$^+$ at 433 nm was observed with an isosbestic point ((a) of FIG. 11). In FIG. 11, (a) is a graph showing the time course of the ultraviolet-visible absorption spectrum of the solution. The horizontal axis indicates the wavelength (nm), and the vertical axis indicates the absorbance. It is considered the above behavior indicates that an electron transfer reaction from Co(II)TPP to molecular oxygen proceeded and Co(III)TPP$^+$ was generated. The time constant of the change in decay of the absorption band at 411 nm with time was substantially the same as the time constant of the change in increase in the absorption band at 433 nm, and the rate constant was determined to be $9.3 \times 10^{-5}$ s$^{-1}$ by pseudo-first-order curve fitting ((b) of FIG. 11). In the graph of (b) of FIG. 11, the horizontal axis indicates the time, and the vertical axis indicates the absorbance. This rate constant exhibited first-order dependence on the oxygen concentration and the Bzn$^+$ concentration, and the catalytic transfer rate constant ($k_{cat}$) was determined to be 0.24 M$^{-2}$s$^{-1}$ from the slope of the plot. Previous research (Ohkubo, K.; Fukuzumi, S. Chem. Eur. J., 2000, 6, 4532) has revealed that the electron transfer reaction from Co(II)TPP to molecular oxygen proceeds efficiently in the presence of a Lewis acid such as metal ions. In the case of Bzn$^+$ used in the present research, it is considered that the reaction proceeded in a manner similar to the Lewis acid catalyzed reaction. The catalyst rate constant of Bzn$^+$ (0.24 M$^{-2}$s$^{-1}$) obtained in the present example was slightly lower than that of lithium perchlorate (0.36) and larger than that of strontium perchlorate (0.10 M$^{-2}$s$^{-1}$) and barium perchlorate (0.051 M$^{-2}$s$^{-1}$). From these results, it is considered that Bzn$^+$ has a relatively strong Lewis acidity. From this catalyst rate constant, the ΔE value as the indicator of the Lewis acidity was determined to be 0.53 eV according to the method described in the literature. Indeed, it has been reported that ammonium salts served as Lewis acids. For example, from the fact that the ΔE value of the ammonium salt in the present example was larger than the ΔE value (0.32 eV) of ammonium hexafluorophosphate (NH$_4$PF$_6$) (e.g., References, etc. 33), it was confirmed that the ammonium salt in the present example exhibits strong Lewis acidity among various types of ammonium. The graph of FIG. 21 shows the Lewis acidities of benzethonium chloride [Bzn$^+$Cl$^-$] and various metal complexes. In FIG. 21, the horizontal axis indicates the ΔE value (eV), and the vertical axis indicates the logarithm of the rate constant (log($k_{cat}$, M$^{-2}$s$^{-1}$)).

Figure 12:
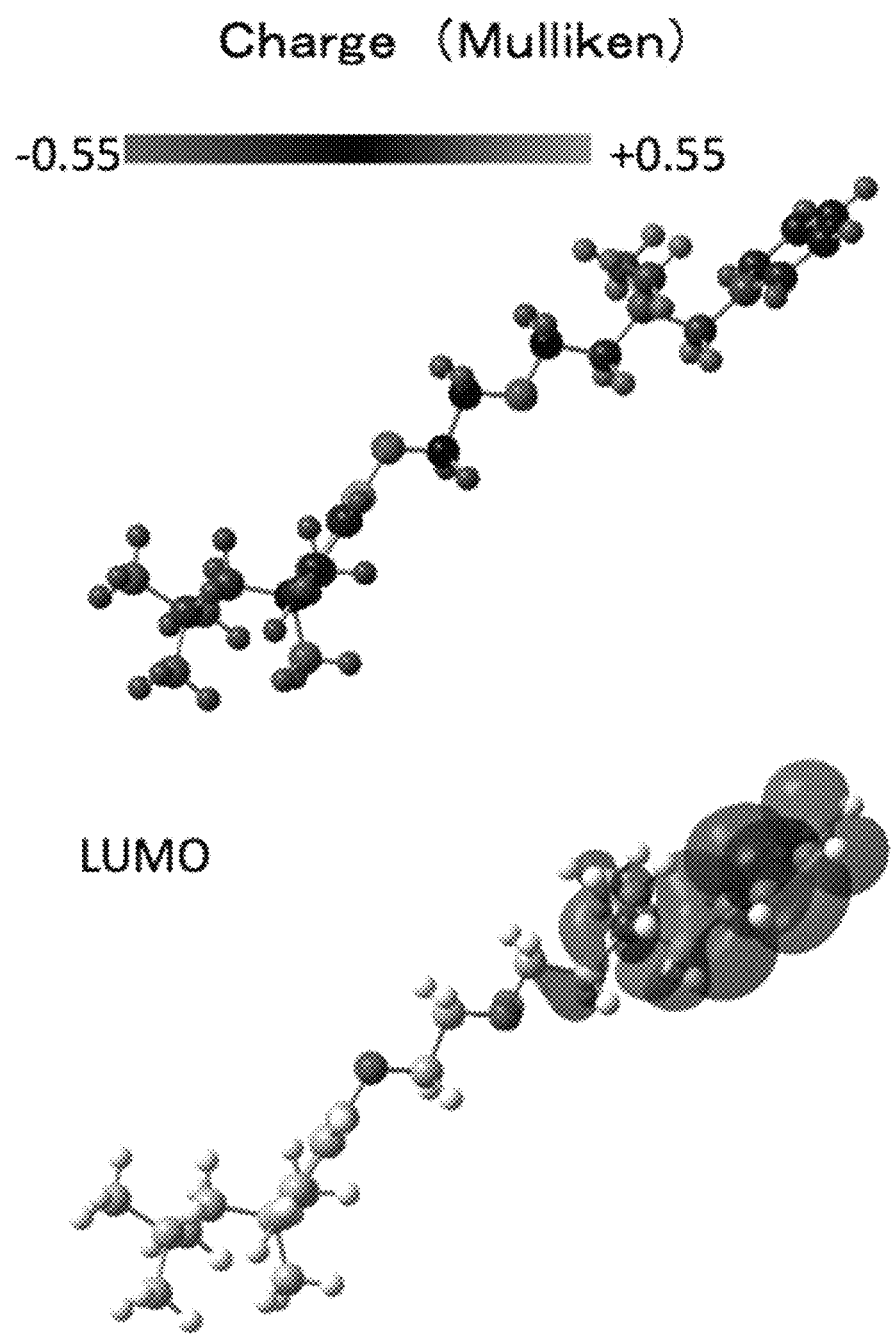
FIG. 12 show the structure of $Bzn^+$ optimized by density functional calculation (B3LYP/6-31G(d) level).

The structure of Bzn$^+$ was optimized by density functional calculation (B3LYP/6-31G(d) level). The obtained structure is shown in FIG. 12. As can be seen from FIG. 12, from the localization of Mulliken charges and LUMO in the vicinity of ammonium nitrogen, it is expected that Bzn$^+$ exhibits Lewis acidity.

Example 3 of Second Aspect of Invention

The present example examined the acceleration effect of a disproportionation reaction of NaClO$_2$ by a Lewis acid.

Figure 13:
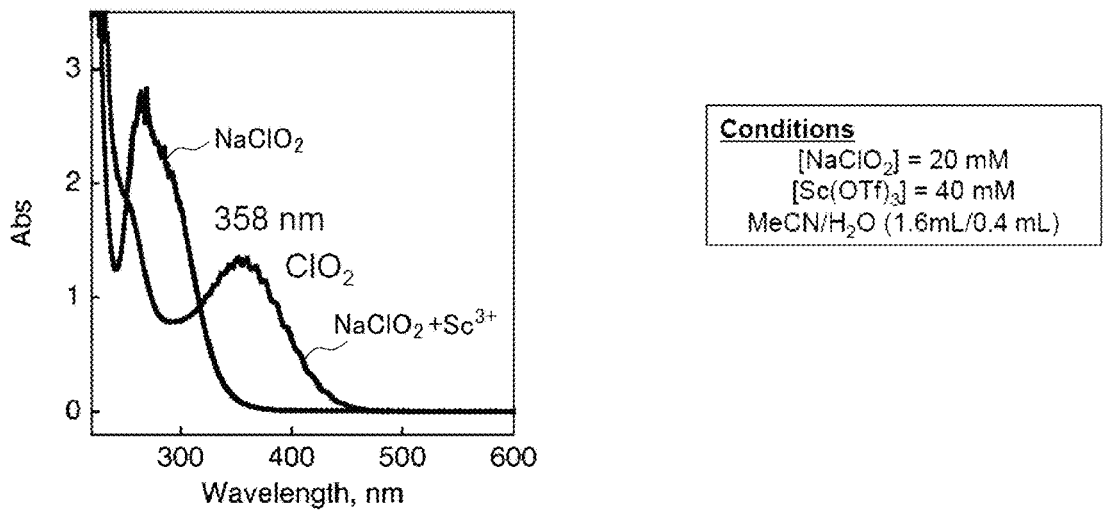
FIG. 13 shows an ultraviolet-visible absorption spectrum of $NaClO_2$ (20 mM) collected after mixing with $Sc(OTf)_3$ (40 mM) in an aqueous solution at 298 K.

As confirmed in Example 1 of the second aspect of the present invention, degradation of sodium chlorite (NaClO$_2$) is not observed because it is very stable in a mixed solution containing a neutral aqueous solution and acetonitrile. When Sc(OTf)$_3$ (40 mM) was added to this 20 mM solution, accompanying the decay of the absorption band of NaClO$_2$, an increase in absorption band characteristic of ClO$_2$ radicals (ClO$_2$.) was observed at 358 nm immediately (FIG. 13). In FIG. 13, the horizontal axis indicates the wavelength (nm), and the vertical axis indicates the absorbance. The increase in this absorption band could be observed as a change over time by decreasing the concentration of Sc(OTf)$_3$, as confirmed in Example 1 of the second aspect of the present invention (FIG. 1). By conducting similar studies on magnesium ions, lithium ions, and the like having lower Lewis acidities than scandium ions, the reaction rate constants of the respective ions were determined. It is known that Lewis acids catalyze various disproportionation reactions. In this reaction, it is considered that ClO$_2$$^-$ is disproportionated to ClO$^-$ and ClO$_3$$^-$ according to the reaction formula (2) of Example 1 of the second aspect of the present invention by a similar mechanism. Thereafter, it is considered that the generated ClO$^-$ reacts with ClO$_2$$^-$, which is present in a large excessive amount, in the presence of an acid and gives Cl$_2$O$_2$ (the reaction formula (3) of Example 1 of the second aspect of the present invention). Thereafter, it is considered that Cl$_2$O$_2$ further reacts with ClO$_2$$^-$ and gives ClO$_2$ radicals as active radical species (the reaction formula (4) of Example 1 of the second aspect of the present invention).

Example 4 of Second Aspect of Invention

The present example examined the generation of ClO$_2$ radicals and acceleration of an oxidation reaction using benzethonium chloride.

Figure 14:
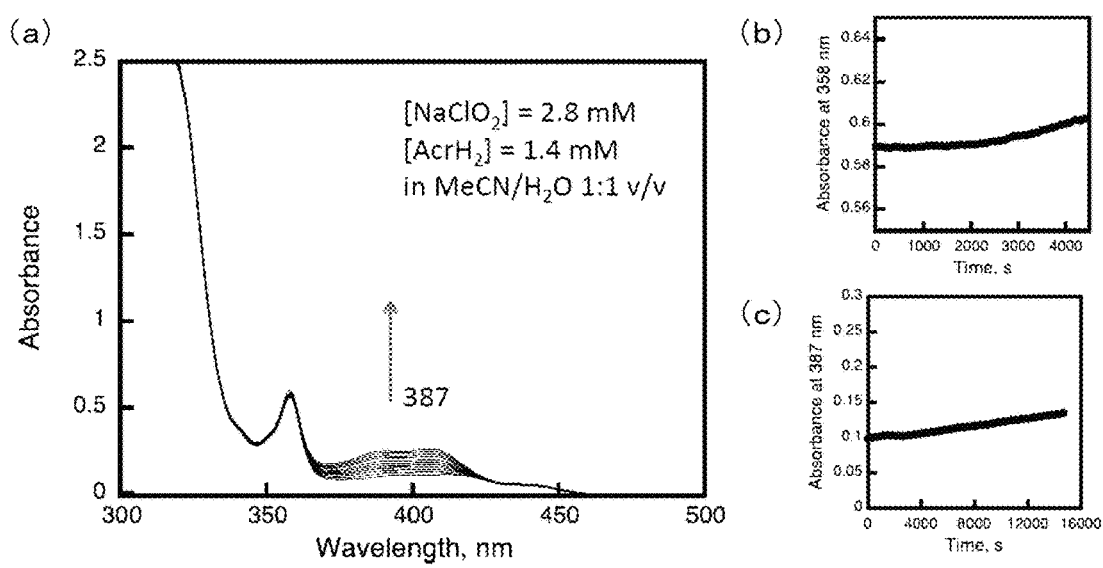
In FIG. 14, (a) to (c) are graphs each showing the time course of a reaction when 10-methyl-9,10-dihydroacridine ($AcrH_2$) (1.4 mM) and sodium chlorite ($NaClO_2$) (2.8 mM) were added to a mixed solution containing deoxygenated acetonitrile and water (deoxygenated acetonitrile:water=1:1 v/v).

ClO$_2$ radicals are considered to exhibit strong oxygenation reaction activity. Thus, first, in a mixed solution containing deoxygenated acetonitrile and water (deoxygenated acetonitrile:water=1:1 v/v), 10-methyl-9,10-dihydroacridine (AcrH$_2$) (1.4 mM) and sodium chlorite (NaClO$_2$) (2.8 mM) were added. In this case, there was almost no progress in an oxygenation reaction of AcrH$_2$ (FIG. 14). In FIGS. 14, (a) to (c) are graphs each showing the time course of the reaction. In the graph (a) of FIG. 14, the horizontal axis indicates the wavelength (nm), and the vertical axis indicates the absorbance. The graph (b) of FIG. 14 shows the time course of the absorbance at a wavelength of 358 nm. In the graph (b) of FIG. 14, the horizontal axis indicates the time (second), and the vertical axis indicates the absorbance. The graph (c) of FIG. 14 shows the time course of the absorbance at a wavelength of 387 nm. In the graph (c) of FIG. 14, the horizontal axis indicates the time (second), and the vertical axis indicates the absorbance.

Figure 15:
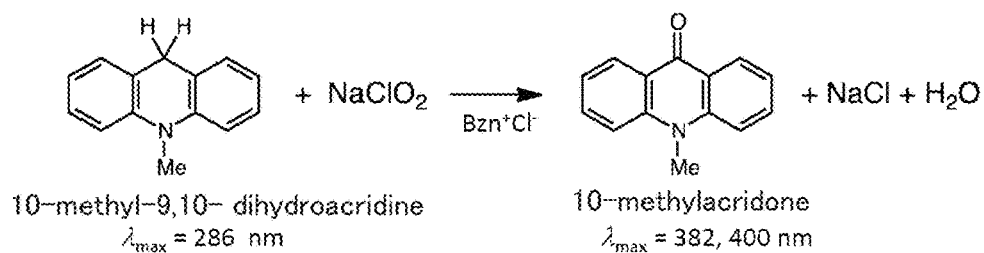
In FIG. 15, (a) and (b) are graphs each showing the time course of a reaction when the same mixed solution as in (a) to (c) of FIG. 14 was prepared and $Bzn^+$ (0.56 mM) was further added thereto.
Figure 15:
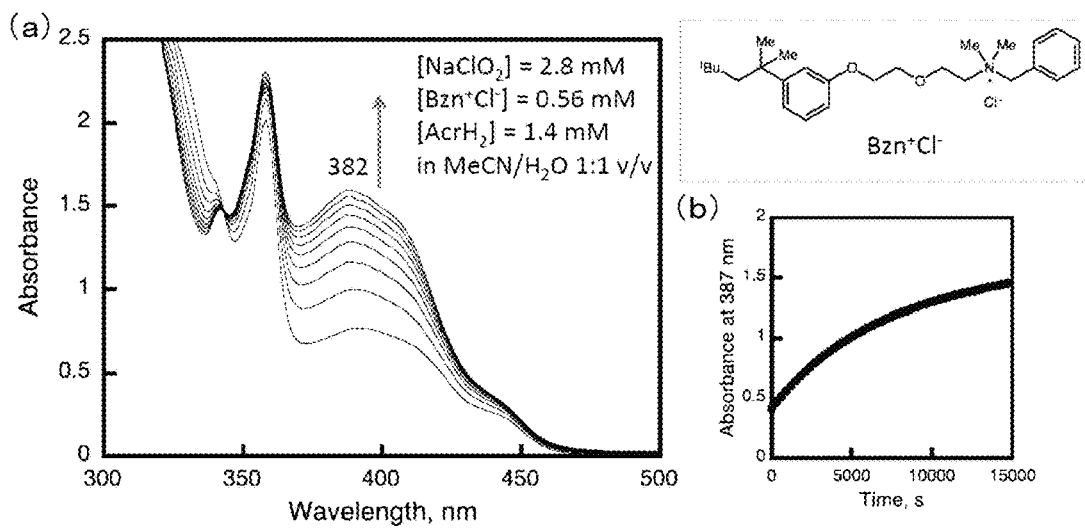

Next, the same mixed solution as that shown in FIG. 14 was prepared. When Bzn$^+$ (0.56 mM) was further added to the mixed solution, an oxygenation reaction from AcrH$_2$ to 10-methylacridone proceeded (FIG. 15). In FIG. 15, (a) and (b) are graphs each showing the time course of the reaction. In the graph (a) of FIG. 15, the horizontal axis indicates the wavelength (nm), and the vertical axis indicates the absorbance. The graph (b) of FIG. 15 shows the time course of the absorbance at a wavelength of 387 nm. In the graph (b) of FIG. 15, the horizontal axis indicates the time (second), and the vertical axis indicates the absorbance. As can be seen from the graphs (a) and (b) of FIG. 15, an increase in absorption derived from 10-methylacridone (λmax=382 nm) with time was observed. This demonstrates that the oxygenation (oxidation) reaction from AcrH$_2$ to 10-methylacridone proceeded.

Figure 16:
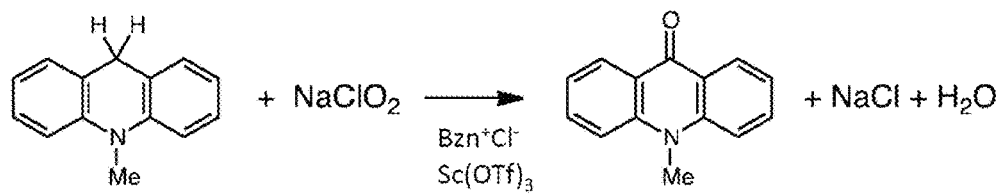
In FIG. 16, (a) and (b) are graphs each showing the time course of a reaction when the same mixed solution as in (a) and (b) of FIG. 15 was prepared and $Sc(OTf)_3$ (3.0 mM) was further added thereto.
Figure 16:
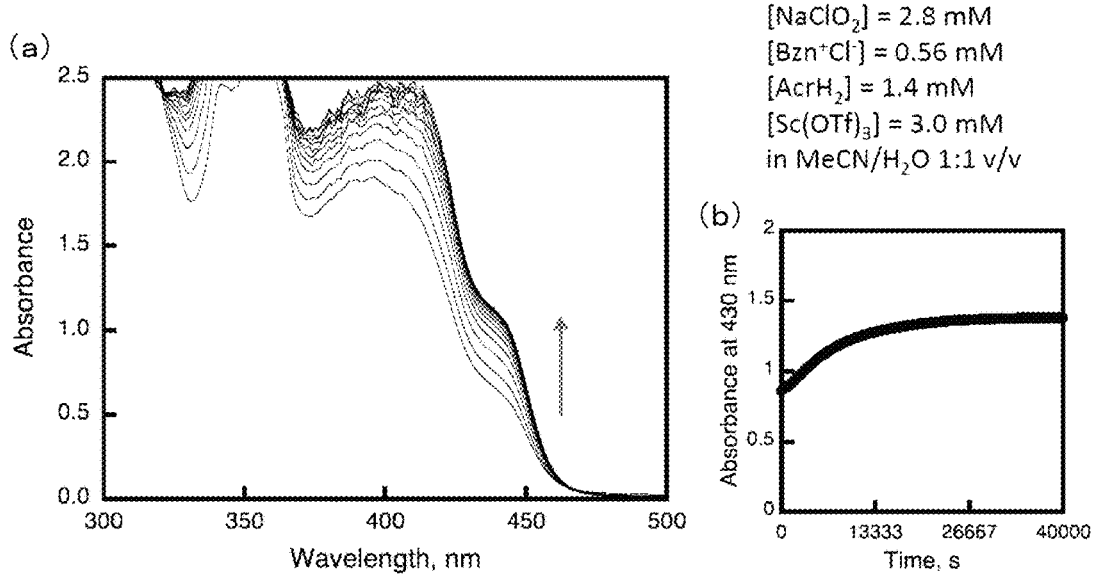
Figure 17:
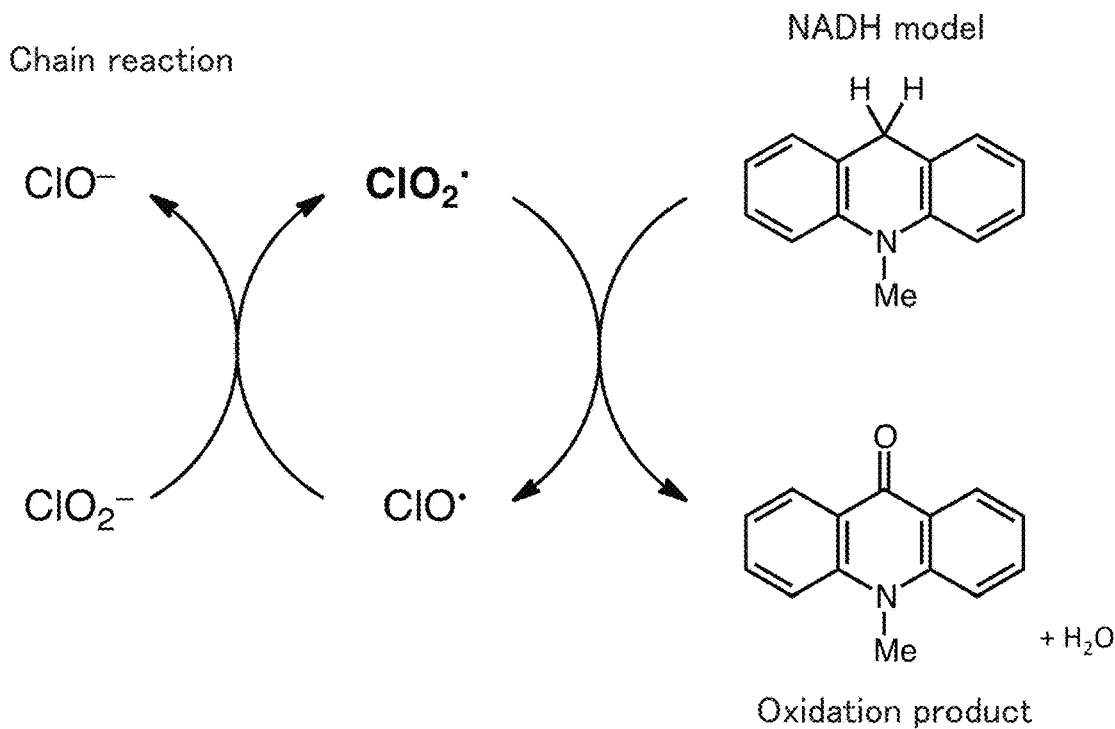
FIG. 17 is a schematic view showing an example of a presumed reaction mechanism of an oxygenation (oxidation) reaction from $AcrH_2$ to 10-methylacridone.

Also, when scandium trifluoromethanesulfonate (Sc (OTf)$_3$, 3.0 mM) was further added to the same mixed solution as that shown in FIG. 15, an oxygenation reaction from AcrH$_2$ to 10-methylacridone proceeded (FIG. 16). In FIG. 16, (a) and (b) are graphs each showing the time course of the reaction. In the graph (a) of FIG. 16, the horizontal axis indicates the wavelength (nm), and the vertical axis indicates the absorbance. The graph (b) of FIG. 16 shows the time course of the absorbance at a wavelength of 430 nm. In the graph (b) of FIG. 16, the horizontal axis indicates the time (second), and the vertical axis indicates the absorbance. As can be seen from the graphs (a) and (b) of FIG. 16, an increase in absorption derived from 10-methylacridone with time was observed. This demonstrates that the oxygenation (oxidation) reaction from AcrH$_2$ to 10-methylacridone proceeded. It is considered that this oxygenation reaction proceeds through the chain reaction mechanism shown in FIG. 17. That is, it is considered that, in this reaction, ClO$_2$. abstracts hydrogen from 10-methylacridone and add oxygen to the 10-methylacridone at the same time, thereby forming acridone. On the other hand, it is considered that ClO$_2$., which is a product obtained after the addition of the oxygen, caused an electron transfer reaction with $ClO_2^-$ and regenerates while giving $ClO^-$ and $ClO_2$.

Example 5 of Second Aspect of Invention

In the present example, an oxygenation reaction of a substrate by $NaClO_2$ using a Lewis acid was used for an oxygenation reaction from triphenylphosphine to triphenylphosphine oxide in order to examine whether it works. More specifically, the oxygenation reaction from triphenylphosphine to triphenylphosphine oxide by $NaClO_2$ was performed in the presence and the absence of scandium triflate $Sc(OTf)_3$, which is a Lewis acid in order to examine whether the Lewis acid promotes the reaction.

Figure 22:
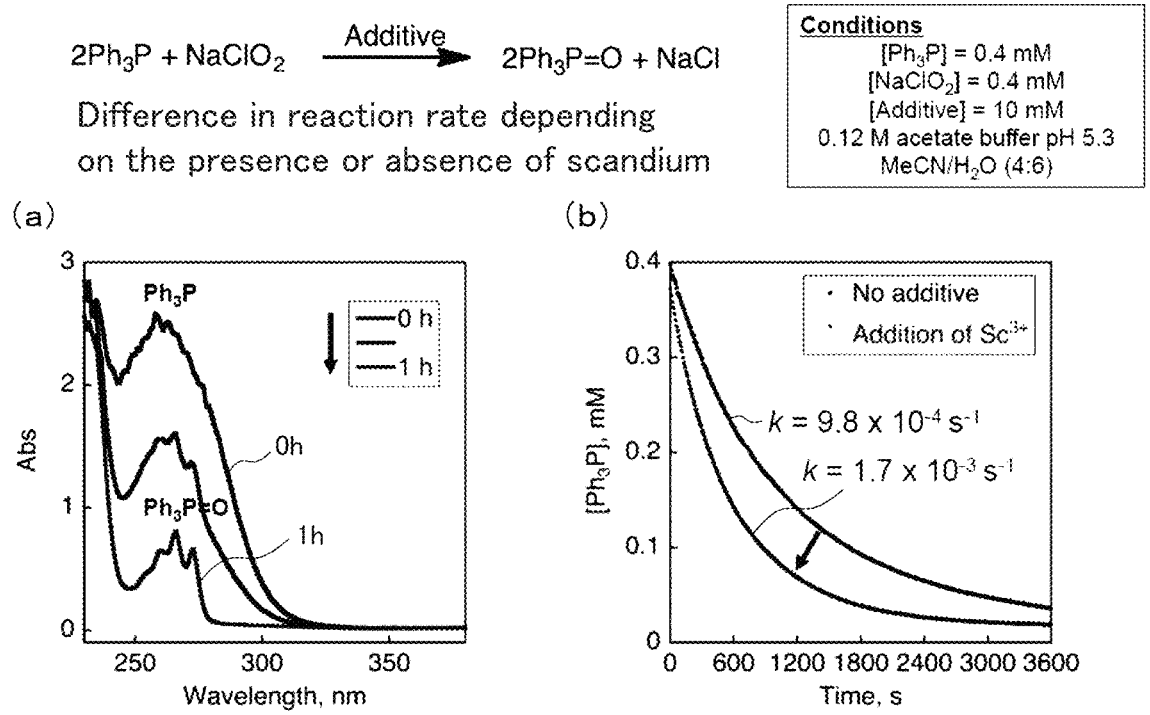
In FIG. 22, (a) is an ultraviolet-visible absorption spectrum showing conversion of triphenylphosphine to triphenylphosphine oxide over time; and (b) is a graph showing the change of a triphenylphosphine ($Ph_3P$) concentration over time in the presence and the absence of $Sc(OTf)_3$ ($Sc^{3+}$).

First, under the following conditions, in the presence or absence of $Sc(OTf)_3$, the reaction was performed at ordinary temperature and atmospheric pressure (no light irradiation), and the reaction was traced by the ultraviolet-visible absorption spectrum. The ultraviolet-visible absorption spectrum shown in (a) of FIG. 22 shows the conversion of triphenylphosphine to triphenylphosphine oxide over time. In (a) of FIG. 22, the horizontal axis indicates the wavelength (nm), and the vertical axis indicates the absorbance. The graph shown in (b) of FIG. 22 shows the changes of a triphenylphosphine ($Ph_3P$) concentration over time in the presence and the absence of $Sc(OTf)_3$ ($Sc^{3+}$). In (b) of FIG. 22, the horizontal axis indicates the time (second), and the vertical axis indicates the triphenylphosphine ($Ph_3P$) concentration (mM). As shown in (b) of FIG. 22, while the reaction rate constant k calculated from the curve in the absence of $Sc^{3+}$ was $9.8 \times 10^{-4}$ $S^{-1}$, the reaction rate constant k calculated from the curve in the presence of $Sc^{3+}$ was increased to $1.7 \times 10^{-3}$ $S^{-1}$. Thus, it was confirmed that $Sc^{3+}$ (a Lewis acid) promoted the reaction.

[$Ph_3P$]=0.4 mM
[$NaClO_2$]=0.4 mM
$Sc(OTf)_3$=0 or 10 mM
0.12M acetate buffer, pH5.3
$MeCN/H_2O$ (4:6)

Figure 18:
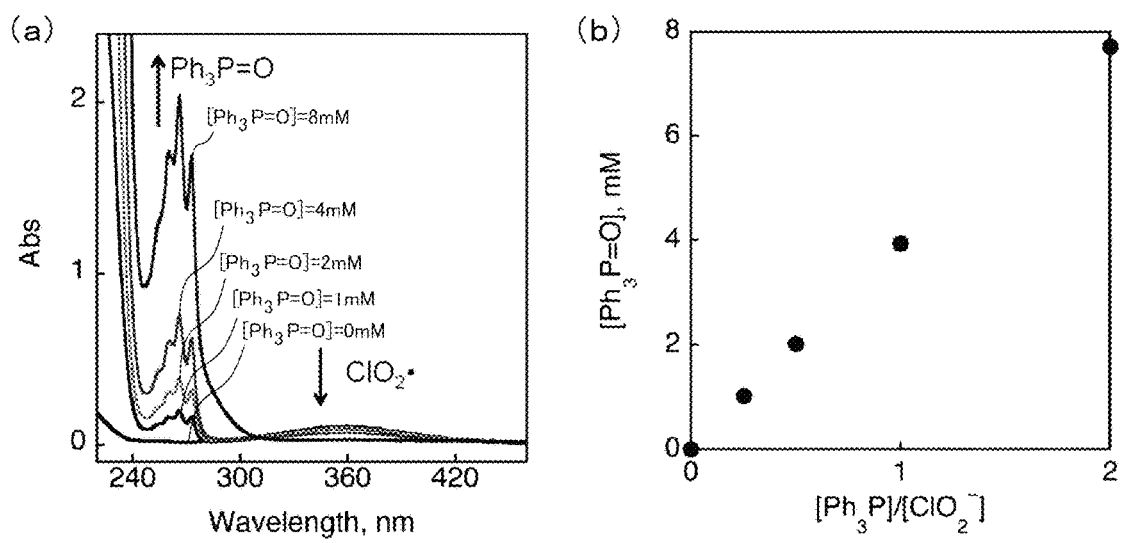
In FIG. 18, (a) is an ultraviolet-visible absorption spectrum showing the result of tracing an oxidation reaction of triphenylphosphine using $NaClO_2$ and scandium triflate; and (b) is a graph showing the relationship between an initial concentration of $Ph_3P$ and a concentration of generated $Ph_3P=O$ in the reaction shown in (a) of FIG. 18.
Figure 18:
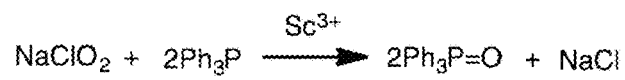

The reaction did not proceed at all by mixing triphenylphosphine and $NaClO_2$ (4.0 mM) in deoxygenated acetonitrile $MeCN/H_2O$ (0.9 ml/0.1 ml). By adding scandium triflate $Sc(OTf)_3$ (30 mM) thereto, oxygenated products were produced efficiently. The initial concentration of triphenylphosphine was set to 1.0 mM, 2.0 mM, 4.0 mM, or 8.0 mM, and each reaction was performed at 25° C. for 15 minutes. The reaction was traced by monitoring the change in the ultraviolet-visible absorption spectrum ((a) of FIG. 18). In (a) of FIG. 18, the horizontal axis indicates the wavelength (nm), and the vertical axis indicates the absorbance. As can be seen from (a) of FIG. 18, it can be considered that $ClO_2$ radicals as active radical species were generated by scandium ions $Sc^{3+}$, and $Ph_3P$ was oxygenated to $Ph_3P=O$. The stoichiometry is as represented by the following reaction formula (6), and it was confirmed that the reaction proceeds almost quantitatively ((b) of FIG. 18). In (b) of FIG. 18, the horizontal axis indicates the initial concentration of $Ph_3P$, and the vertical axis indicates the concentration of the generated $Ph_3P=O$.

$$2Ph_3P+NaClO_2 \rightarrow 2Ph_3P=O+NaCl \quad (6)$$

Example 6 of Second Aspect of Invention

Figure 20:
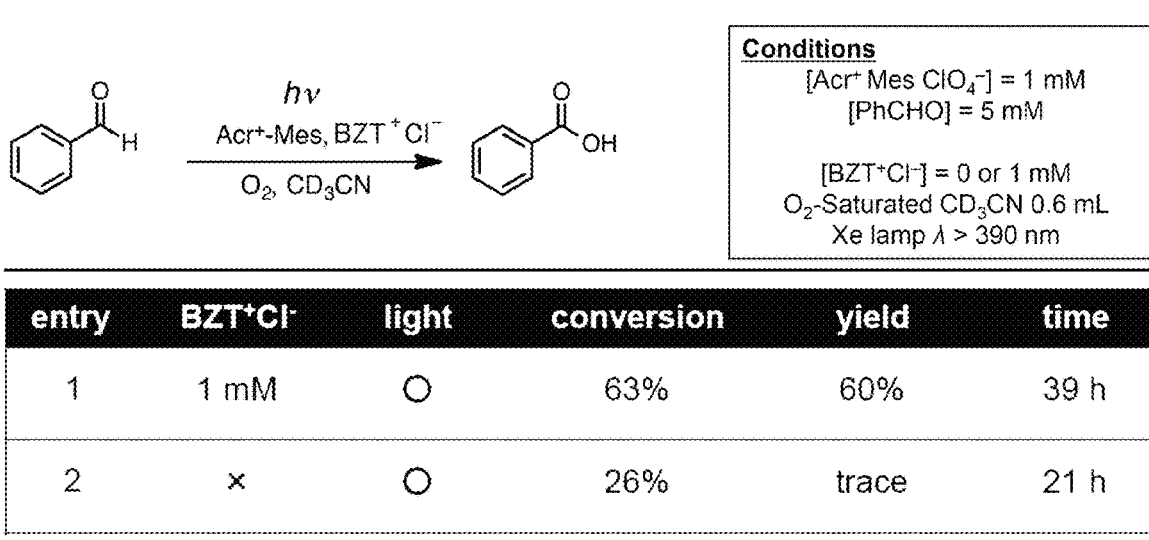
FIG. 20 shows the yield etc. in an example where an oxidation reaction product (benzoic acid) was obtained by performing an oxidation reaction of a raw material aromatic compound (benzaldehyde) in acetonitrile in the presence of perchlorate ($Acr^+$-Mes $ClO_4$) of 9-mesityl-10-methylacridinium ($Acr^+$-Mes) and oxygen.

In the present example, an oxidation reaction of a raw material aromatic compound (benzaldehyde) was performed in acetonitrile in the presence of perchlorate ($Acr^+$-Mes $ClO_4^-$) of 9-mesityl-10-methylacridinium ($Acr^+$-Mes) and oxygen, thereby obtaining an oxidation reaction product (benzoic acid) (FIG. 20). The reaction was performed in the presence or absence of $Bzn^+Cl^-$.

As a reaction solvent, 0.6 ml of $CD_3CN$ saturated with oxygen gas was used. As shown in FIG. 20, 1 mM of $Acr^+$-Mes $ClO_4^-$, 5 mM of benzaldehyde (PhCHO), and 0 or 1 mM of $Bzn^+Cl^-$ were added thereto, and the resultant mixture was or was not irradiated with light at a wavelength of 390 nm emitted from a xenon lamp. The reaction was traced by $^1HNMR$. The results obtained are shown in the table in FIG. 20. In the table, "x" means the reagent was not added or light irradiation was not performed; "○" means light irradiation was performed; "conversion" indicates the conversion rate of the raw material aromatic compound (benzaldehyde); "yield" indicates the yield of the benzoic acid; and "time" indicates the reaction time. As can be seen from FIG. 20, in the case where $Bzn^+Cl^-$ was not added, the yield of the benzoic acid was a trace amount. In the case where $Bzn^+Cl^-$ was added, the yield of the benzoic acid was 60%, and the conversion rate of the benzaldehyde was 63%. It is considered this result indicates that, while the reactivity of $Acr^+$-Mes was low in the absence of the Lewis acid ($Bzn^+Cl^-$), generation of radicals from $Acr^+$-Mes was promoted in the presence of the Lewis acid ($Bzn^+Cl^-$), which suggests that the Lewis acid ($Bzn^+Cl^-$) served as a strong reaction promoter.

Example 7 of Second Aspect of Invention

In the present example, according to the measurement method described in the above section "Measurement method of Lewis acidity", oxidation reaction products of cobalt tetraphenylporphyrin were produced using various types of ammonium as radical generating catalysts and oxygen molecules as a radical source (also serving as an oxidizing agent). More specifically, as to acetonitrile (MeCN) that contains cobalt tetraphenylporphyrin in the following chemical reaction formula (1a), saturated $O_2$, and an object whose Lewis acidity is to be measured (e.g., a cation of a metal or the like, represented by $M^{n+}$ in the following chemical reaction formula (1a)), the change of the ultraviolet-visible absorption spectrum was measured at room temperature, and whether $CoTPP^+$ was obtained as an oxidation reaction product was examined.

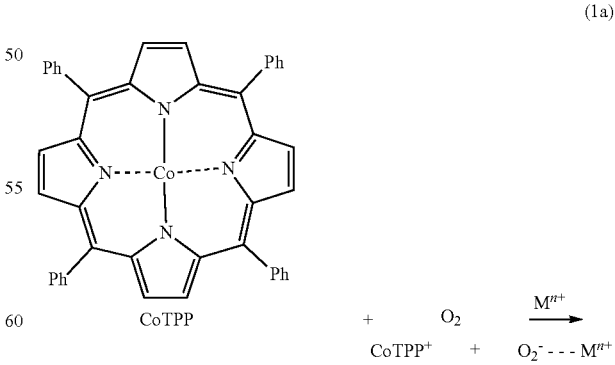

(1a)

The oxidation reaction was performed using each type of ammonium shown in the following table as a radical generating catalyst. In the following table, the numerical value expressed in the unit "$k_{cat}$, $M^{-2}s^{-1}$" is a rate constant of reaction between CoTPP and oxygen in the presence of Lewis acid, which is an indicator of the Lewis acidity of each ammonium. The numerical value expressed in the unit "LUMO, eV" is the energy level of LUMO. The "benzetonium chloride" means benzethonium chloride, "benzalkonium chloride" means benzalkonium chloride, "tetramethylammonium hexafluorophosphate" means tetramethylammonium hexafluorophosphate, "tetrabutylammonium hexafluorophosphate" means tetrabutylammonium hexafluorophosphate, and "ammonium hexafluorophosphate" means ammonium hexafluorophosphate.

TABLE TPP

| | LUMO, eV | $k_{cat}$, $M^{-2}$ $s^{-1}$ |
|---|---|---|
| benzetonium chloride | −4.12 | 0.24 |
| benzalkonium chloride | −4.02 | 0.18 |
| tetramethylammonium hexafluorophosphate | −3.58 | >0.1 |
| tetrabutylammonium hexafluorophosphate | −2.07 | >0.1 |
| ammonium hexafluorophosphate | −5.73 | 20 |

Examples of Third Aspect of Invention

Next, specific examples of the third aspect of the present invention will be described. It is to be noted, however, that the third aspect of the present invention is not limited to the following examples. Drugs used in the following examples of the third aspect of the present invention and comparative examples were produced in the following manners.

Example 1 of the Third Aspect of the Present Invention 5 g of sodium chlorite was dissolved in purified water to obtain 100 ml of an aqueous solution. Thus, the 40,000 ppm sodium chlorite aqueous solution was obtained (solution A). 0.1 g of benzethonium chloride was dissolved in 100 ml of purified water to prepare a 100 ml of 1000 ppm aqueous solution (solution B). 0.1 M phosphate-NaOH buffer (pH=9.5) was provided. To 600 ml of purified water at pH 7, 20 ml of the solution A diluted 10-fold and 80 ml of the buffer were added, and then 80 ml of the solution B was added. Purified water was further added to make the total amount 800 ml. In this manner, the drug according to Example 1 of the third aspect of the present invention was obtained.

Example 2 of the Third Aspect of the Present Invention 5 g of sodium chlorite was dissolved in purified water to obtain 100 ml of an aqueous solution. Thus, the 40,000 ppm sodium chlorite aqueous solution was obtained. 0.1 g of benzethonium chloride was dissolved in 100 ml of purified water to prepare a 1000 ppm aqueous solution. The 40,000 ppm sodium chlorite aqueous solution was diluted 40-fold to obtain a 1000 ppm aqueous solution. 10 ml of the sodium chlorite aqueous solution and 10 ml of the benzethonium chloride aqueous solution were added to 80 ml of purified water to obtain a 100 ppm aqueous solution. In this manner, a drug according to Example 2 of the third aspect of the present invention was obtained.

Comparative Example 1 of the Third Aspect of the Present Invention a bactericide containing sodium hypochlorite and water (commercially available product)

Comparative Example 2 of the Third Aspect of the Present Invention a sterilizing deodorizer containing sodium hypochlorite (commercially available product)

Comparative Example 3 of the Third Aspect of the Present Invention a sterilizing deodorizer containing hypochlorous acid and water (commercially available product)

Comparative Example 4 of the Third Aspect of the Present Invention a sterilizing deodorizer containing sodium hypochlorite and water (commercially available product) Comparative Example 5 of the third aspect of the present invention:
a sterilizing deodorizer containing sodium hypochlorite and water (commercially available product)

Comparative Example 6 of the Third Aspect of the Present Invention a sodium chlorite standard solution 1000 ppm (test product)

Comparative Example 7 of the Third Aspect of the Present Invention 5 g of sodium chlorite (Wako Pure Chemical Industries, Ltd.) was dissolved in 100 ml of purified water to prepare a 40,000 ppm aqueous solution. The 40,000 ppm aqueous solution was further diluted with purified water to obtain a 100 ppm aqueous solution. In this manner, a test product according to Comparative Example 7 of the third aspect of the present invention was obtained.

Comparative Example 8 of the third aspect of the present invention:
a benzethonium chloride aqueous solution (test product)

Experimental Example 1 of Third Aspect of Invention

In Experimental Example 1 of the third aspect of the present invention, the following were provided first.
Bacterial Strains to be Used:
  *Staphylococcus aureus*
  *Escherichia coli* MV1184
Bacterial Solution:
  Bacteria cultured in a BHI agar medium were collected with a platinum loop and placed in a BHI liquid medium, and the BHI liquid medium was shaken. The bacteria were allowed to grow in the BHI liquid medium for a whole day and night. 50 µl of the resultant culture solution was diluted 190-fold with a BHI liquid medium, and mixed well with the BHI liquid medium by stirring. The resultant mixture was used as a bacterial solution.

Using each bacterial strain and bacterial solution, the effect was examined in the following manner.
A microplate (with a lid) was sterilized for 10 minutes with a UV sterilization lamp. Next, a BHI liquid medium, the bacterial solution, and the drug according to Example 1 of the third aspect of the present invention were injected in this order into each well with a micropipette. The bacteria were cultured at 37° C. for 24 hours. Thereafter, the bacteria were examined using a microplate reader, and the minimum inhibitory concentration (MIC) was determined. As a control, the same examination was performed using the liquid medium only. Further, 10 µl of the culture solution was collected from the well in the vicinity of the MIC, and inoculated in a petri dish. The bacteria were cultured at 37° C. for 24 hours, and the minimum bactericidal concentration (MBC) was determined. The results obtained are shown in Table 4.

Using the bactericide according to Comparative Example 1 of the third aspect of the present invention instead of the drug according to Example 1 of the third aspect of the present invention, the MIC and MBC were determined in the same manner. The results obtained are shown in Table 4.

Using each of the sterilizing deodorizers according to Comparative Examples 2 to 5 of the third aspect of the present invention instead of the drug according to Example 1 of the third aspect of the present invention, the MIC of the *Staphylococcus aureus* was determined in the same manner. The results obtained are shown in Table 4.

Using the test product according to Comparative Example 6 of the third aspect of the present invention instead of the drug according to Example 1 of the third aspect of the present invention, the MIC of the *Staphylococcus aureus* and the MIC and MBC of the *Escherichia coli* were determined in the same manner. The results obtained are shown in Table 4.

same manner as in Experimental Example 1 of the third aspect of the present invention. The results obtained are shown in Table 6.

TABLE 6

|  |  | Ex. 3 |
|---|---|---|
| *Streptococcus pyogenes* | MIC (ppm) | 0.1 |
|  | MBC (ppm) | 1.0 |

Experimental Example 4 of Third Aspect of Invention

In Experimental Example 4 of the third aspect of the present invention, the following were provided first.
Bacterial Strains to be Used:
 *Streptococcus mutans*
Bacterial Solution:
 Bacteria cultured in a BHI agar medium were collected with a platinum loop and placed in a BHI liquid medium, and the BHI liquid medium was shaken. The bacteria were allowed to grow in the BHI liquid medium for a whole day and night. 50 µl of the resultant culture solution was diluted

TABLE 4

|  |  | Ex. 1 | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|
| S. aureus | MIC (ppm) | 1.56 | 300 | ineffective | ineffective | ineffective | ineffective | 40 |
|  | MBC (ppm) | 3.12 | 300 |  |  |  |  |  |
| E. coli | MIC (ppm) | 12.5 | 220 |  |  |  |  | 30 |
|  | MBC (ppm) | 20.0 | 220 |  |  |  |  | 50 |

Experimental Example 2 of Third Aspect of Invention

Using the drug according to Example 2 or Comparative Example 7 or 8 of the third aspect of the present invention instead of the drug according to Example 1 of the third aspect of the present invention, the MIC of the *Escherichia coli* was determined in the same manner. The results obtained are shown in Table 5.

TABLE 5

|  |  | Ex. 2 | Comp. Ex. 7 | Comp. Ex. 8 |
|---|---|---|---|---|
| E. coli | MIC (ppm) | 12.5> | 25< | 17.5 |

Experimental Example 3 of Third Aspect of Invention

In Experimental Example 3 of the third aspect of the present invention, the following were provided first.
Bacterial Strain to be Used:
 *Streptococcus pyogenes*
Bacterial Solution:
 A bacterial solution was obtained in the same manner as in Experimental Example 1 of the third aspect of the present invention.

Using the above bacterial strain and bacterial solution and the drug according to Example 1 of the third aspect of the present invention, the MIC and MBC were determined in the 190-fold with a BHI liquid medium, and mixed well with the BHI liquid medium by stirring. The resultant mixture was used as a bacterial solution.

Using each bacterial strain and bacterial solution, the effect was examined in the following manner.

The bacterial solution was injected with a micropipette into a BHI liquid medium placed in each of two test tubes. Saccharose was added thereto so that the concentration thereof was 0.2%. The bacteria were cultured at 37° C. for 18 hours to allow them to form a biofilm. The medium in each test tube was discarded in a beaker, and the biofilm was washed twice with PBS. The drug according to Example 1 of the third aspect of the present invention was injected into one of the test tube, and PBS was injected into the other test tube. Then, the test tubes were shaken at 37° C. for 30 minutes. The liquid in each test tube was discarded in a beaker, and the biofilm was washed twice with PBS. ABHI liquid medium was injected into the test tubes, and the bacteria were cultured at 37° C. for 24 hours. 10 µl of the medium collected from each test tube was inoculated into a nutrient agar medium, and the bacteria were cultured at 37° C. for 24 hours. The presence or absence of colonies was checked through visual observation. As a result, while no colony was observed in the test tube to which the drug according to Example 1 of the third aspect of the present invention had been injected, many colonies were observed in the test tube to which PBS had been injected.

In order to examine the effect of the drug on the bacterial cells in the biofilm, the following test was conducted further.

The bacterial solution was injected with a micropipette into a BHI liquid medium placed in microtubes. Saccharose was added thereto so that the concentration thereof was 0.2%. The bacteria were cultured at 37° C. for 18 hours to allow them to form a biofilm. The medium in each microtube was discarded in a beaker, and the biofilm was washed twice with PBS. The drug according to Example 1 of the third aspect of the present invention was injected into one of the microtubes, and PBS was injected into the other microtube. The bacteria in the former microtube and the bacteria in the latter microtube were aged at 37° C. for 15 minutes and 30 minutes, respectively. The liquid in each microtube was discarded in a beaker, and the biofilm was washed twice with PBS. A BHI liquid medium was injected into the test tubes and homogenized. Thereafter, the bacteria were cultured at 37° C. for 24 hours. 10 l of the medium collected from each microtube was inoculated into a nutrient agar medium, and the bacteria were cultured at 37° C. for 24 hours. The presence or absence of colonies was checked through visual observation. As a result, while no colony was observed in the microtube to which the drug according to Example 1 of the third aspect of the present invention had been injected, many colonies were observed in the microtube to which PBS had been injected. These results demonstrate that, by impregnating a biofilm with the drug according to Example 1 of the third aspect of the present invention, the drug acts on bacteria deep inside the biofilm to exhibit the sterilizing effect.

Experimental Example 5 of Third Aspect of Invention

In Experimental Example 5 of the third aspect of the present invention, the following bacterial strains were used. Except for this, the MIC and MBC were determined using the drug according to Example 1 of the third aspect of the present invention in the same manner as in Experimental Example 1 of the third aspect of the present invention. The results obtained are shown in Table 7.

Bacterial Strains to be Used:
  Bacteria 1 (*Porphyromonas gingivalis*)
  Bacteria 2 (*Treponema denticola*)
  Bacteria 3 (*Tannerella forsythensis*)
  Bacteria 4 (*Aggregatibacter actinomycetemcomitans*)

TABLE 7

|  |  | Ex. 1 |
|---|---|---|
| Bacteria 1 | MIC (ppm) | 20.0 |
|  | MBC (ppm) | 20.0 |

TABLE 7-continued

|  |  | Ex. 1 |
|---|---|---|
| Bacteria 2 | MIC (ppm) | 25.0 |
|  | MBC (ppm) | 25.0 |
| Bacteria 3 | MIC (ppm) | 12.5 |
|  | MBC (ppm) | 12.5 |
| Bacteria 4 | MIC (ppm) | 35-45 |
|  | MBC (ppm) | 35-50 |

Experimental Example 6 of Third Aspect of Invention

Test pieces (25.4 mm×25.4 mm) respectively made of iron, aluminum, tin plate, and stainless steel were washed. Thereafter, the test pieces made of each material were immersed in resin containers containing the drug according to Example 1 of the third aspect of the present invention, a 1.2% sodium hypochlorite aqueous solution, and tap water, respectively, and then, the resin containers were covered with a lid. The test pieces were taken out on a nonwoven fabric after a lapse of each time period shown in Tables 8 and 9, and the conditions of the test pieces were examined through visual observation. In the examination, pictures were taken when necessary, and a microscope was used when the change was subtle. The evaluation was made using the following evaluation criteria.
  −: no corrosion
  ±: generation of rust
  +: fairly large amount of rust
  ++: vary large amount of rust
  +++: corrosion of metal surfaces

TABLE 8

| Test piece |  | 10 min | 30 min | 1 hr | 3 hr | 6 hr |
|---|---|---|---|---|---|---|
| Iron | Example 1 | ± | ± | ± | + | + |
|  | Hypochlorous acid | + | + | ++ | +++ | +++ |
|  | Tap water | ± | ± | ± | ± | + |
| Aluminum | Example 1 | − | − | − | − | − |
|  | Hypochlorous acid | ± | ± | ± | + | + |
|  | Tap water | − | − | − | − | − |
| Tin plate | Example 1 | − | − | − | − | − |
|  | Hypochlorous acid | − | − | − | ± | ± |
|  | Tap water | − | − | − | − | − |
| Stainless steel | Example 1 | − | − | − | − | − |
|  | Hypochlorous acid | − | − | − | − | − |
|  | Tap water | − | − | − | − | − |

TABLE 9

| Test piece |  | 1 day | 3 days | 1 week | 2 weeks | 3 weeks | 4 weeks |
|---|---|---|---|---|---|---|---|
| Iron | Example 1 | + | + | + | + | + | + |
|  | Hypochlorous acid | +++ | +++ | +++ | +++ | +++ | +++ |
|  | Tap water | + | + | + | + | + | + |
| Aluminum | Example 1 | − | − | − | − | − | − |
|  | Hypochlorous acid | ++ | ++ | ++ | +++ | +++ | +++ |
|  | Tap water | − | − | − | − | − | − |
| Tin plate | Example 1 | − | ± | ± | ± | ± | ± |
|  | Hypochlorous acid | + | ++ | +++ | +++ | +++ | +++ |
|  | Tap water | − | ± | ± | + | + | + |
| Stainless steel | Example 1 | − | − | − | − | − | − |
|  | Hypochlorous acid | − | − | − | − | − | − |
|  | Tap water | − | − | − | − | − | − |

Experimental Example 7 of Third Aspect of Invention

The deodorizing performance test was conducted in accordance with JEM 1467 "domestic air cleaner" in the Standards of the Japan Electrical Manufacturers' Association. In the measurement, cigarettes were burned while operating a circulator in an acrylic container (1 m in height×1 m in width×1 m in depth) with an internal volume of 1 $m^3$ to fill the container with smoke. After all the cigarettes were burned, the circulator was stopped, and the drug according to Example 1 of the third aspect of the present invention was sprayed in the container by operating a sprayer. The concentrations of three components, namely, ammonia, acetaldehyde, and acetic acid, in the container were measured over 2 hours at regular intervals to trace the change in concentrations. Similarly, formaldehyde vapor was injected into an acrylic container and the formaldehyde concentration in the container was measured over 2 hours at regular intervals to trace the change in concentration. The sprayer was operated in "Manual" mode. As a control, a blank test in which the sprayer was not operated was also conducted. The results obtained are shown in Tables 10 to 13. The malodorous components were measured using detector tubes (Gastec Corporation). The detector tubes used for the measurement are shown below.

Detector Tubes Used for Measurement ammonia: No. 3L acetaldehyde: No. 92L acetic acid: No. 81L formaldehyde: No. 91

TABLE 10

| Elapsed time | Ammonia concentration (ppm) | | Example 1 |
|---|---|---|---|
| | Example 1 | Blank test | Removal rate (%) |
| Start | 30 | 32 | — |
| 5 min | 8 | 32 | 73 |
| 10 min | 5 | 32 | 83 |
| 20 min | 4 | 32 | 87 |
| 30 min | 2 | 32 | 93 |
| 45 min | 1 | 31 | 97 |
| 60 min | 1> | 31 | 97< |
| 90 min | 1> | 31 | 97< |
| 120 min | 1> | 26 | 97< |

TABLE 11

| Elapsed time | Acetaldehyde concentration (ppm) | | Example 1 |
|---|---|---|---|
| | Example 1 | Blank test | Removal rate (%) |
| Start | 14 | 14 | — |
| 5 min | 12 | 14 | 14 |
| 10 min | 10 | 14 | 29 |
| 20 min | 10 | 14 | 29 |
| 30 min | 7 | 14 | 50 |
| 45 min | 7 | 14 | 50 |
| 60 min | 7 | 14 | 50 |
| 90 min | 7 | 14 | 50 |
| 120 min | 6 | 14 | 57 |

TABLE 12

| Elapsed time | Acetic acid concentration (ppm) | | Example 1 |
|---|---|---|---|
| | Example 1 | Blank test | Removal rate (%) |
| Start | 12 | 10 | — |
| 5 min | 0.5> | 10 | 96< |
| 10 min | 0.5> | 10 | 96< |
| 20 min | 0.5> | 10 | 96< |
| 30 min | 0.5> | 10 | 96< |
| 45 min | 0.5> | 10 | 96< |
| 60 min | 0.5> | 9.5 | 96< |
| 90 min | 0.5> | 9.0 | 96< |
| 120 min | 0.5> | 9.0 | 96< |

TABLE 13

| Elapsed time | Formaldehyde concentration (ppm) | | Example 1 |
|---|---|---|---|
| | Example 1 | Blank test | Removal rate (%) |
| Start | 20 | 20 | — |
| 5 min | 10 | 20 | 50 |
| 10 min | 8 | 20 | 60 |
| 20 min | 5 | 20 | 75 |
| 30 min | 3 | 20 | 85 |
| 45 min | 2 | 20 | 90 |
| 60 min | 2 | 20 | 90 |
| 90 min | 2 | 18 | 90 |
| 120 min | 2 | 18 | 90 |

Experimental Example 8 of Third Aspect of Invention

The drug according to Example 1 of the third aspect of the present invention was sprayed using a sprayer to measure the deodorizing performance for cigarette odor. First, cigarettes were burned in a room with a 6-tatami mat size to fill the room with smoke at a predetermined concentration. Next, a sprayer was set in the room, and the odor intensity in the room was measured three times, namely, before operating the sprayer, one hour after operating the sprayer, and two hours after operating the sprayer. The sprayer was set near a wall in the room, and the odor was collected at a height of 1 m in the middle of the room. Two circulation fans were set in the room, and they were operated at all times to maintain the air-circulating conditions. The sprayer was operated in "Manual" mode. As a control, a blank test in which the sprayer was not operated was also conducted. The odor intensity was determined as follows according to the six-grade odor intensity measurement method. The results obtained are shown in Table 14.

The odor intensity was evaluated by six testers (test panel). The results were calculated by determining the average value of the odor intensities given by the respective testers. The six-grade odor intensity measurement method is a method for converting odor intensity to a numerical value using human olfaction. The members of the test panel who had joined the test were those who had taken the legally-required olfactometry and had been admitted as having normal olfaction.

In the six-grade odor intensity measurement method, the following numerical values are used as evaluation criteria.

0: odorless

1: barely perceivable odor (detection threshold concentration)

2: weakly perceivable odor (recognition threshold concentration)

3: easily perceivable odor

4: strong odor

5: very strong odor

TABLE 14

| | Odor intensity | |
|---|---|---|
| Elapsed time | Example 1 | Blank test |
| Start | 4.6 | 4.5 |
| 1 h | 3.5 | 4.5 |
| 2 h | 2.9 | 4.2 |

Experimental Example 9 of Third Aspect of Invention

The drug according to Example 1 of the third aspect of the present invention was sprayed with a sprayer to measure the performance thereof to remove airborne bacteria (general bacteria, fungi). First, a sprayer was set in a room with a 6-tatami mat size, and the concentration of airborne bacteria in the air was measured three times, namely, before operating the sprayer, one hour after operating the sprayer, and two hours after operating the sprayer. The sprayer was set near a wall in the room, and the airborne bacteria were collected at a height of 1 m in the middle of the room. Two circulation fans were set in the room, and they were operated at all times to maintain the air-circulating conditions. The airborne bacteria were measured by a filtration method using a membrane filter. The sprayer was operated in "Manual" mode. As a control, a blank test in which the sprayer was not operated was also conducted. The results obtained are shown in Tables 15 and 16.

Measurement conditions etc. in Experimental Example 9 of the third aspect of the present invention Filter to be used: Toyo Roshi Kaisha, Ltd., 37 mm Monitors Amount of sucked air: 300 l (sucked for 15 minutes at 20 l/min)

Medium to be used: m-TGE Broth liquid medium for general bacteria (Toyo Seisakusho Kaisha, Ltd.)
  m-Green Y & M Broth liquid medium for fungi (Toyo Seisakusho Kaisha, Ltd.)

Culture conditions: 30° C. for 72 hours for general bacteria 30° C. for 5 days for fungi

TABLE 15

| | The number of airborne general bacteria (the number of bacteria/300 l) | | |
|---|---|---|---|
| Elapsed time | Example 1 | Blank test | Removal rate (%) |
| Start | 13 | 11 | — |
| 1 h | 0 | 11 | 100 |
| 2 h | 0 | 11 | 100 |

TABLE 16

| | The number of airborne fungi (the number of fungi/300 l) | | |
|---|---|---|---|
| Elapsed time | Example 1 | Blank test | Removal rate (%) |
| Start | 10 | 11 | — |
| 1 h | 0 | 10 | 100 |
| 2 h | 0 | 9 | 100 |

Experimental Example 10 of Third Aspect of Invention

In Experimental Example 10 of the third aspect of the present invention, the following bacterial strains were used. Except for this, the MIC or MBC was determined using the drug according to Example 1 of the third aspect of the present invention in the same manner as in Experimental Example 1 of the third aspect of the present invention. The results obtained are shown in Table 17.

Bacterial Strains to be Used:
  *Streptococcus mutans*
  hemolytic *streptococcus*
  *Bacillus subtilis*
  *Candida albicans*

TABLE 17

| | | Example 1 |
|---|---|---|
| Streptococcus mutans | MIC (ppm) | 5 |
| | MBC (ppm) | 15 |
| Hemolytic streptococcus | MIC (ppm) | 0.1 |
| | MBC (ppm) | 1.0 |
| Bacillus subtilis | MIC (ppm) | 12.5 |
| | MBC (ppm) | |
| Candida albicans | MIC (ppm) | 5> |
| | MBC (ppm) | |

Experimental Example 11 of Third Aspect of Invention

Using the drug according to Example 1 of the third aspect of the present invention, a deodorization test was performed in accordance with an instrumental analysis implementation manual; a detector tube method, a gas chromatography method (the Certification Standards of Antibacterial Finished Textile Products of Japan Textile Evaluation Technology Council were applied with necessary modifications). The results obtained are shown in Table 18.

TABLE 18

| Odor component | Impression of odor | Concentration 1 (ppm) | Concentration 2 (ppm) | Gas reduction rate (%) |
|---|---|---|---|---|
| ammonia | excrement | 100 | 7 | 93 |
| acetic acid | vinegar | 50 | 1 | 98 |
| hydrogen sulfide | rotten egg | 4.00 | 0.12 | 97 |
| methyl mercaptan | rotten onion | 8.00 | 4.96 | 38 |
| tritylamine | rotten fish | 28.00 | 3.08 | 89 |
| isovaleric acid | musty socks | 38.00 | 0.38 | 99 |

Concentration 1: initial gas concentration
Concentration 2: gas concentration after a lapse of 2 hours
Gas reduction rate: ([concentration 1 − concentration 2]/concentration 1) × 100

Experimental Example 12 of Third Aspect of Invention

The drug according to Example 1 of the third aspect of the present invention was applied to acne lesions for 14 consecutive days (a few times a day, about 2 ml/time). As a result, it was clear that the acne was healed by the application of the drug. This result demonstrates that the drug of the third aspect of the present invention is useful as an acne treatment agent.

Examples of Fourth Aspect of Invention

Next, specific examples of the fourth aspect of the present invention will be described. It is to be noted, however, that the fourth aspect of the present invention is not restricted by the following examples. In examples of the fourth aspect of the present invention to be described below, drugs for use in agriculture and livestock industry according to the examples also may be referred to simply as "drugs".

First, as drugs to be used in the following experimental examples of the fourth aspect of the invention, drugs according to examples of the fourth aspect of the present invention and comparative examples were produced in the following manners.

Example 1 of the Fourth Aspect of the Present Invention 5 g of sodium chlorite was dissolved in purified water to obtain 100 ml of an aqueous solution. Thus, the 40,000 ppm sodium chlorite aqueous solution was obtained (solution A). 0.1 g of benzethonium chloride was dissolved in 100 ml of purified water to prepare a 100 ml of 1000 ppm aqueous solution (solution B). 0.1 mol/l phosphate-NaOH buffer (pH=9.5) was provided. To 600 ml of purified water at pH 7, 20 ml of the solution A diluted 10-fold and 80 ml of the buffer were added, and then 80 ml of the solution B was added. Purified water was further added to make the total amount 800 ml. In this manner, the drug according to Example 1 of the fourth aspect of the present invention was obtained.

Example 2 of the Fourth Aspect of the Present Invention 5 g of sodium chlorite was dissolved in purified water to obtain 100 ml of an aqueous solution. Thus, the 40,000 ppm sodium chlorite aqueous solution was obtained. 0.1 g of benzethonium chloride was dissolved in 100 ml of purified water to prepare a 1000 ppm aqueous solution. The 40,000 ppm sodium chlorite aqueous solution was diluted 40-fold to obtain a 1000 ppm aqueous solution. 10 ml of the sodium chlorite aqueous solution and 10 ml of the benzethonium chloride aqueous solution were added to 80 ml of purified water to obtain a 100 ppm aqueous solution. In this manner, a drug according to Example 2 of the fourth aspect of the present invention was obtained.

Comparative Example 1 of the Fourth Aspect of the Present Invention a bactericide containing sodium hypochlorite and water (commercially available product)

Comparative Example 2 of the Fourth Aspect of the Present Invention a sterilizing deodorizer containing sodium hypochlorite (commercially available product)

Comparative Example 3 of the Fourth Aspect of the Present Invention a sterilizing deodorizer containing hypochlorous acid and water (commercially available product)

Comparative Example 4 of the Fourth Aspect of the Present Invention a sterilizing deodorizer containing sodium hypochlorite and water (commercially available product)

Comparative Example 5 of the Fourth Aspect of the Present Invention a sterilizing deodorizer containing sodium hypochlorite and water (commercially available product)

Comparative Example 6 of the Fourth Aspect of the Present Invention a sodium chlorite standard solution 1000 ppm (test product)

Comparative Example 7 of the Fourth Aspect of the Present Invention 5 g of sodium chlorite (Wako Pure Chemical Industries, Ltd.) was dissolved in 100 ml of purified water to prepare a 40,000 ppm aqueous solution. The 40,000 ppm aqueous solution was further diluted with purified water to obtain a 100 ppm aqueous solution. In this manner, a test product according to Comparative Example 7 of the fourth aspect of the present invention was obtained.

Comparative Example 8 of the Fourth Aspect of the Present Invention a benzethonium chloride aqueous solution (test product)

Experimental Example 1 of Fourth Aspect of Invention

In Experimental Example 1 of the fourth aspect of the present invention, the following were provided first.
Bacterial Strains to be Used:
*Staphylococcus aureus*
*Escherichia coli* MV1184
Bacterial Solution:
Bacteria cultured in a BHI agar medium were collected with a platinum loop and placed in a BHI liquid medium, and the BHI liquid medium was shaken. The bacteria were allowed to grow in the BHI liquid medium for a whole day and night. 50 µl of the resultant culture solution was diluted 190-fold with a BHI liquid medium, and mixed well with the BHI liquid medium by stirring. The resultant mixture was used as a bacterial solution.

Using each bacterial strain and bacterial solution, the effect was examined in the following manner.

A microplate (with a lid) was sterilized for 10 minutes with a UV sterilization lamp. Next, a BHI liquid medium, the bacterial solution, and the drug according to Example 1 of the fourth aspect of the present invention were injected in this order into each well with a micropipette. The bacteria were cultured at 37° C. for 24 hours. Thereafter, the bacteria were examined using a microplate reader, and the minimum inhibitory concentration (MIC) was determined. As a control, the same examination was performed using the liquid medium only. Further, 10 μl of the culture solution was collected from the well in the vicinity of the MIC, and inoculated in a petri dish. The bacteria were cultured at 37° C. for 24 hours, and the minimum bactericidal concentration (MBC) was determined. The results obtained are shown in Table 19.

Using the bactericide according to Comparative Example 1 of the fourth aspect of the present invention instead of the drug according to Example 1 of the fourth aspect of the present invention, the MIC and MBC were determined in the same manner. The results obtained are shown in Table 19.

Using each of the sterilizing deodorizers according to Comparative Examples 2 to 5 of the fourth aspect of the present invention instead of the drug according to Example 1 of the fourth aspect of the present invention, the MIC of the *Staphylococcus aureus* was determined in the same manner. The results obtained are shown in Table 19.

Using the test product according to Comparative Example 6 of the fourth aspect of the present invention instead of the drug according to Example 1 of the fourth aspect of the present invention, the MIC of the *Staphylococcus aureus* and the MIC and MBC of the *Escherichia coli* were determined in the same manner. The results obtained are shown in Table 19.

Using the above bacterial strain and bacterial solution and the drug according to Example 1 of the fourth aspect of the present invention, the MIC and MBC were determined in the same manner as in Experimental Example 1 of the fourth aspect of the present invention. The results obtained are shown in Table 21.

TABLE 21

|  |  | Ex. 1 |
|---|---|---|
| *Streptococcus pyogenes* | MIC (ppm) | 0.1 |
|  | MBC (ppm) | 1.0 |

Experimental Example 4 of Fourth Aspect of Invention

In Experimental Example 4 of the fourth aspect of the present invention, the following were provided first.

Bacterial Strains to be Used:

*Streptococcus mutans*

Bacterial Solution:

Bacteria cultured in a BHI agar medium were collected with a platinum loop and placed in a BHI liquid medium, and the BHI liquid medium was shaken. The bacteria were allowed to grow in the BHI liquid medium for a whole day and night. 50 μl of the resultant culture solution was diluted

TABLE 19

|  |  | Ex. 1 | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|
| S. aureus | MIC (ppm) | 1.56 | 300 | ineffective | ineffective | ineffective | ineffective | 40 |
|  | MBC (ppm) | 3.12 | 300 |  |  |  |  |  |
| E. coli | MIC (ppm) | 12.5 | 220 |  |  |  |  | 30 |
|  | MBC (ppm) | 20.0 | 220 |  |  |  |  | 50 |

Experimental Example 2 of Fourth Aspect of Invention

Using the drug according to Example 2 or Comparative Example 7 or 8 of the fourth aspect of the present invention instead of the drug according to Example 1 of the fourth aspect of the present invention, the MIC of the *Escherichia coli* was determined in the same manner. The results obtained are shown in Table 20.

TABLE 20

|  |  | Ex. 2 | Comp. Ex. 7 | Comp. Ex. 8 |
|---|---|---|---|---|
| E. coli | MIC (ppm) | 12.5> | 25< | 17.5 |

Experimental Example 3 of Fourth Aspect of Invention

In Experimental Example 3 of the fourth aspect of the present invention, the following were provided first.

Bacterial Strain to be Used:

*Streptococcus pyogenes*

Bacterial Solution:

A bacterial solution was obtained in the same manner as in Experimental Example 1 of the fourth aspect of the present invention.

190-fold with a BHI liquid medium, and mixed well with the BHI liquid medium by stirring. The resultant mixture was used as a bacterial solution.

Using each bacterial strain and bacterial solution, the effect was examined in the following manner.

The bacterial solution was injected with a micropipette into a BHI liquid medium placed in each of two test tubes. Saccharose was added thereto so that the concentration thereof was 0.2%. The bacteria were cultured at 37° C. for 18 hours to allow them to form a biofilm. The medium in each test tube was discarded in a beaker, and the biofilm was washed twice with PBS. The drug according to Example 1 of the fourth aspect of the present invention was injected into one of the test tube, and PBS was injected into the other test tube. Then, the test tubes were shaken at 37° C. for 30 minutes. The liquid in each test tube was discarded in a beaker, and the biofilm was washed twice with PBS. ABHI liquid medium was injected into the test tubes, and the bacteria were cultured at 37° C. for 24 hours. 10 μl of the medium collected from each test tube was inoculated into a nutrient agar medium, and the bacteria were cultured at 37° C. for 24 hours. The presence or absence of colonies was checked through visual observation. As a result, while no colony was observed in the test tube to which the drug according to Example 1 of the fourth aspect of the present invention had been injected, many colonies were observed in the test tube to which PBS had been injected.

In order to examine the effect of the drug on the bacterial cells in the biofilm, the following test was conducted further.

The bacterial solution was injected with a micropipette into a BHI liquid medium placed in microtubes for Bio-Masher. Saccharose was added thereto so that the concentration thereof was 0.2%. The bacteria were cultured at 37° C. for 18 hours to allow them to form a biofilm. The medium in each microtube was discarded in a beaker, and the biofilm was washed twice with PBS. The drug according to Example 1 of the fourth aspect of the present invention was injected into one of the microtubes, and PBS was injected into the other microtube. The bacteria in the former microtube and the bacteria in the latter microtube were aged at 37° C. for 15 minutes and 30 minutes, respectively. The liquid in each microtube was discarded in a beaker, and the biofilm was washed twice with PBS. A BHI liquid medium was injected into the test tubes and homogenized. Thereafter, the bacteria were cultured at 37° C. for 24 hours. 10 μl of the medium collected from each microtube was inoculated into a nutrient agar medium, and the bacteria were cultured at 37° C. for 24 hours. The presence or absence of colonies was checked through visual observation. As a result, while no colony was observed in the microtube to which the drug according to Example 1 of the fourth aspect of the present invention had been injected, many colonies were observed in the microtube to which PBS had been injected. These results demonstrate that, by impregnating a biofilm with the drug according to Example 1 of the fourth aspect of the present invention, the drug acts on bacteria deep inside the biofilm to exhibit the sterilizing effect.

Experimental Example 5 of Fourth Aspect of Invention

In Experimental Example 5 of the fourth aspect of the present invention, the following bacterial strains were used. Except for this, the MIC and MBC were determined using the drug according to Example 1 of the fourth aspect of the present invention in the same manner as in Experimental Example 1 of the fourth aspect of the present invention. The results obtained are shown in Table 22.

Bacterial Strains to be Used:
Bacteria 1 (*Porphyromonas gingivalis*)
Bacteria 2 (*Treponema denticola*)
Bacteria 3 (*Tannerella forsythensis*)
Bacteria 4 (*Aggregatibacter actinomycetemcomitans*)

TABLE 22

|  |  | Ex. 1 |
|---|---|---|
| Bacteria 1 | MIC (ppm) | 20.0 |
|  | MBC (ppm) | 20.0 |
| Bacteria 2 | MIC (ppm) | 25.0 |
|  | MBC (ppm) | 25.0 |
| Bacteria 3 | MIC (ppm) | 12.5 |
|  | MBC (ppm) | 12.5 |
| Bacteria 4 | MIC (ppm) | 35-45 |
|  | MBC (ppm) | 35-50 |

Experimental Example 6 of Fourth Aspect of Invention

Test pieces (25.4 mm×25.4 mm) respectively made of iron, aluminum, tin plate, and stainless steel were washed. Thereafter, the test pieces made of each material were immersed in resin containers containing the drug according to Example 1 of the fourth aspect of the present invention, a 1.2% sodium hypochlorite aqueous solution, and tap water, respectively, and then, the resin containers were covered with a lid. The test pieces were taken out on a nonwoven fabric after a lapse of each time period shown in Tables 23 and 24, and the conditions of the test pieces were examined through visual observation. In the examination, pictures were taken when necessary, and a microscope was used when the change was subtle. The evaluation was made using the following evaluation criteria.

−: no corrosion
±: generation of rust
+: fairly large amount of rust
++: vary large amount of rust
+++: corrosion of metal surfaces

TABLE 23

| Test piece |  | 10 min | 30 min | 1 hr | 3 hr | 6 hr |
|---|---|---|---|---|---|---|
| Iron | Example 1 | ± | ± | ± | + | + |
|  | Hypochlorous acid | + | + | ++ | +++ | +++ |
|  | Tap water | ± | ± | ± | − | + |
| Aluminum | Example 1 | − | − | − | − | − |
|  | Hypochlorous acid | ± | ± | ± | + | + |
|  | Tap water | − | − | − | − | − |
| Tin plate | Example 1 | − | − | − | − | − |
|  | Hypochlorous acid | − | − | − | ± | ± |
|  | Tap water | − | − | − | − | − |
| Stainless steel | Example 1 | − | − | − | − | − |
|  | Hypochlorous acid | − | − | − | − | − |
|  | Tap water | − | − | − | − | − |

TABLE 24

| Test piece |  | 1 day | 3 days | 1 week | 2 weeks | 3 weeks | 4 weeks |
|---|---|---|---|---|---|---|---|
| Iron | Example 1 | + | + | + | + | + | + |
|  | Hypochlorous acid | +++ | +++ | +++ | +++ | +++ | +++ |
|  | Tap water | + | + | + | + | + | + |
| Aluminum | Example 1 | − | − | − | − | − | − |
|  | Hypochlorous acid | ++ | ++ | ++ | +++ | +++ | +++ |
|  | Tap water | − | − | − | − | − | − |
| Tin plate | Example 1 | − | ± | ± | ± | ± | ± |
|  | Hypochlorous acid | + | ++ | +++ | +++ | +++ | +++ |
|  | Tap water | − | ± | ± | + | + | + |
| Stainless steel | Example 1 | − | − | − | − | − | − |
|  | Hypochlorous acid | − | − | − | − | − | − |
|  | Tap water | − | − | − | − | − | − |

Experimental Example 7 of Fourth Aspect of Invention

The deodorizing performance test was conducted in accordance with JEM 1467 "domestic air cleaner" in the Standards of the Japan Electrical Manufacturers' Association. In the measurement, cigarettes were burned while operating a circulator in an acrylic container (1 m in height×1 m in width×1 m in depth) with an internal volume of 1 m³ to fill the container with smoke. After all the cigarettes were burned, the circulator was stopped, and the drug according to Example 1 of the fourth aspect of the present invention was sprayed in the container by operating a sprayer. The concentrations of three components, namely, ammonia, acetaldehyde, and acetic acid, in the container were measured over 2 hours at regular intervals to trace the change in concentrations. Similarly, formaldehyde vapor was injected into an acrylic container and the formaldehyde concentration in the container was measured over 2 hours at regular intervals to trace the change in concentration. The sprayer was operated in "Manual" mode. As a control, a blank test in which the sprayer was not operated was also conducted. The results obtained are shown in Tables 25 to 28. The malodorous components were measured using detector tubes (Gastec Corporation). The detector tubes used for the measurement are shown below.

Detector Tubes Used for Measurement ammonia: No. 3L acetaldehyde: No. 92L acetic acid: No. 81L formaldehyde: No. 91

TABLE 25

| | Ammonia concentration (ppm) | | Example 1 |
|---|---|---|---|
| Elapsed time | Example 1 | Blank test | Removal rate (%) |
| Start | 30 | 32 | — |
| 5 min | 8 | 32 | 73 |
| 10 min | 5 | 32 | 83 |
| 20 min | 4 | 32 | 87 |
| 30 min | 2 | 32 | 93 |
| 45 min | 1 | 31 | 97 |
| 60 min | 1> | 31 | 97< |
| 90 min | 1> | 31 | 97< |
| 120 min | 1> | 26 | 97< |

TABLE 26

| | Acetaldehyde concentration (ppm) | | Example 1 |
|---|---|---|---|
| Elapsed time | Example 1 | Blank test | Removal rate (%) |
| Start | 14 | 14 | — |
| 5 min | 12 | 14 | 14 |
| 10 min | 10 | 14 | 29 |
| 20 min | 10 | 14 | 29 |
| 30 min | 7 | 14 | 50 |
| 45 min | 7 | 14 | 50 |
| 60 min | 7 | 14 | 50 |
| 90 min | 7 | 14 | 50 |
| 120 min | 6 | 14 | 57 |

TABLE 27

| | Acetic acid concentration (ppm) | | Example 1 |
|---|---|---|---|
| Elapsed time | Example 1 | Blank test | Removal rate (%) |
| Start | 12 | 10 | — |
| 5 min | 0.5> | 10 | 96< |
| 10 min | 0.5> | 10 | 96< |
| 20 min | 0.5> | 10 | 96< |
| 30 min | 0.5> | 10 | 96< |
| 45 min | 0.5> | 10 | 96< |
| 60 min | 0.5> | 9.5 | 96< |
| 90 min | 0.5> | 9.0 | 96< |
| 120 min | 0.5> | 9.0 | 96< |

TABLE 28

| | Formaldehyde concentration (ppm) | | Example 1 |
|---|---|---|---|
| Elapsed time | Example 1 | Blank test | Removal rate (%) |
| Start | 20 | 20 | — |
| 5 min | 10 | 20 | 50 |
| 10 min | 8 | 20 | 60 |
| 20 min | 5 | 20 | 75 |
| 30 min | 3 | 20 | 85 |
| 45 min | 2 | 20 | 90 |
| 60 min | 2 | 20 | 90 |
| 90 min | 2 | 18 | 90 |
| 120 min | 2 | 18 | 90 |

Experimental Example 8 of Fourth Aspect of Invention

The drug according to Example 1 of the fourth aspect of the present invention was sprayed using a sprayer to measure the deodorizing performance for cigarette odor. First, cigarettes were burned in a room with a 6-tatami mat size to fill the room with smoke at a predetermined concentration. Next, a sprayer was set in the room, and the odor intensity in the room was measured three times, namely, before operating the sprayer, one hour after operating the sprayer, and two hours after operating the sprayer. The sprayer was set near a wall in the room, and the odor was collected at a height of 1 m in the middle of the room. Two circulation fans were set in the room, and they were operated at all times to maintain the air-circulating conditions. The sprayer was operated in "Manual" mode. As a control, a blank test in which the sprayer was not operated was also conducted. The odor intensity was determined as follows according to the six-grade odor intensity measurement method. The results obtained are shown in Table 29.

The odor intensity was evaluated by six testers (test panel). The results were calculated by determining the average value of the odor intensities given by the respective testers. The six-grade odor intensity measurement method is a method for converting odor intensity to a numerical value using human olfaction. The members of the test panel who had joined the test were those who had taken the legally-required olfactometry and had been admitted as having normal olfaction.

In the six-grade odor intensity measurement method, the following numerical values are used as evaluation criteria.
0: odorless
1: barely perceivable odor (detection threshold concentration)
2: weakly perceivable odor (recognition threshold concentration)

3: easily perceivable odor
4: strong odor
5: very strong odor

TABLE 29

|  | Odor intensity | |
| --- | --- | --- |
| Elapsed time | Example 1 | Blank test |
| Start | 4.6 | 4.5 |
| 1 h | 3.5 | 4.5 |
| 2 h | 2.9 | 4.2 |

Experimental Example 9 of Fourth Aspect of Invention

The drug according to Example 1 of the fourth aspect of the present invention was sprayed with a sprayer to measure the performance thereof to remove airborne bacteria (general bacteria, fungi). First, a sprayer was set in a room with a 6-tatami mat size, and the concentration of airborne bacteria in the air was measured three times, namely, before operating the sprayer, one hour after operating the sprayer, and two hours after operating the sprayer. The sprayer was set near a wall in the room, and the airborne bacteria were collected at a height of 1 m in the middle of the room. Two circulation fans were set in the room, and they were operated at all times to maintain the air-circulating conditions. The airborne bacteria were measured by a filtration method using a membrane filter. The sprayer was operated in "Manual" mode. As a control, a blank test in which the sprayer was not operated was also conducted.

The results obtained are shown in Tables 30 and 31.

Measurement Conditions Etc. In Experimental Example 9 of the Fourth Aspect of the Present Invention Filter to be used: Toyo Roshi Kaisha, Ltd., 37 mm Monitors
Amount of sucked air: 300 l (sucked for 15 minutes at 20 l/min)
Medium to be used: m-TGE Broth liquid medium for general bacteria (Toyo Seisakusho Kaisha, Ltd.)
    m-Green Y & M Broth liquid medium for fungi (Toyo Seisakusho Kaisha, Ltd.)
Culture conditions: 30° C. for 72 hours for general bacteria 30° C. for 5 days for fungi

TABLE 30

|  | The number of airborne general bacteria (the number of bacteria/300 l) | | Example 1 |
| --- | --- | --- | --- |
| Elapsed time | Example 1 | Blank test | Removal rate (%) |
| Start | 13 | 11 | — |
| 1 h | 0 | 11 | 100 |
| 2 h | 0 | 11 | 100 |

TABLE 31

|  | The number of airborne fungi (the number of fungi/300 l) | | Example 1 |
| --- | --- | --- | --- |
| Elapsed time | Example 1 | Blank test | Removal rate (%) |
| Start | 10 | 11 | — |
| 1 h | 0 | 10 | 100 |
| 2 h | 0 | 9 | 100 |

Experimental Example 10 of Fourth Aspect of Invention

In Experimental Example 10 of the fourth aspect of the present invention, the following bacterial strains were used. Except for this, the MIC or MBC was determined using the drug according to Example 1 of the fourth aspect of the present invention in the same manner as in Experimental Example 1 of the fourth aspect of the present invention. The results obtained are shown in Table 32.

Bacterial Strains to be Used:
  *Streptococcus mutans*
  hemolytic *streptococcus*
  *Bacillus subtilis*
  methicillin-resistant *Staphylococcus aureus* (MRSA)

TABLE 32

|  |  | Example 1 |
| --- | --- | --- |
| *Streptococcus* | MIC (ppm) | 5 |
| *mutans* | MBC (ppm) | 15 |
| *Hemolytic* | MIC (ppm) | 0.1 |
| *streptococcus* | MBC (ppm) | 1.0 |
| *Bacillus subtilis* | MIC (ppm) | 12.5 |
|  | MBC (ppm) |  |
| MRSA | MIC (ppm) | 2 |
|  | MBC (ppm) |  |

Experimental Example 11 of Fourth Aspect of Invention

Using the drug according to Example 1 of the fourth aspect of the present invention, a deodorization test was performed in accordance with an instrumental analysis implementation manual; a detector tube method, a gas chromatography method (the Certification Standards of Antibacterial Finished Textile Products of Japan Textile Evaluation Technology Council were applied with necessary modifications). The results obtained are shown in Table 33.

TABLE 33

| Odor component | Impression of odor | Concentration 1 (ppm) | Concentration 2 (ppm) | Gas reduction rate (%) |
| --- | --- | --- | --- | --- |
| ammonia | excrement | 100 | 7 | 93 |
| acetic acid | vinegar | 50 | 1 | 98 |
| hydrogen sulfide | rotten egg | 4.00 | 0.12 | 97 |
| methyl mercaptan | rotten onion | 8.00 | 4.96 | 38 |
| tritylamine | rotten fish | 28.00 | 3.08 | 89 |
| isovaleric acid | musty socks | 38.00 | 0.38 | 99 |

Concentration 1: initial gas concentration
Concentration 2: gas concentration after a lapse of 2 hours
Gas reduction rate: ([concentration 1 − concentration 2]/concentration 1) × 100

Experimental Example 12 of Fourth Aspect of Invention

The drug according to the fourth aspect of the present invention was administered to mice in order to examine whether the drug according to the fourth aspect of the present invention is highly safe.

Using the drug according to Example 1 of the fourth aspect of the present invention, an acute oral toxicity test was performed on mice in accordance with OECD TG 420 (fixed dose procedure). The test was conducted by Japan Food Research Laboratories. As a result, LD50 of the drug was 2000 mg/kg or more in both the female and male mice. This result demonstrates that that the drug according to the fourth aspect of the present invention is highly safe.

Experimental Example 13 of Fourth Aspect of Invention

The drug according to the fourth aspect of the present invention was administered to rabbits in order to examine whether the drug according to the fourth aspect of the present invention is highly safe.

Using the drug according to Example 1 of the fourth aspect of the present invention, an eye irritation test was performed on rabbits in accordance with OECD TG 405 Acute Eye Irritation/Corrosion. The test was conducted by Japan Food Research Laboratories. As a result, it was found that the drug was non-irritating. From this result, it was found that that the drug according to the fourth aspect of the present invention is highly safe.

Experimental Example 14 of Fourth Aspect of Invention

The drug according to the fourth aspect of the present invention was administered to rabbits in order to examine whether the drug according to the fourth aspect of the present invention is highly safe.

Using the drug according to Example 1 of the fourth aspect of the present invention, a primary skin irritation test was performed on rabbits in accordance with OECD TG 404 Acute Skin Irritation/Corrosion. The test was conducted by Japan Food Research Laboratories. As a result, it was found that the drug was slightly irritating. This result demonstrates that the drug according to the fourth aspect of the present invention is highly safe.

Experimental Example 15 of Fourth Aspect of Invention

The drug according to the fourth aspect of the present invention was administered to guinea pigs in order to examine whether the drug according to the fourth aspect of the present invention is highly safe.

Using the drug according to Example 1 of the fourth aspect of the present invention, a continuous skin irritation test was performed on guinea pigs by applying the drug on their skin for 14 consecutive days. The test was conducted by Life Science Laboratories, Ltd. As a result, it was found that the drug was non-irritating. This demonstrates that that the drug according to the fourth aspect of the present invention is highly safe.

Experimental Example 16 of Fourth Aspect of Invention

The drug according to the fourth aspect of the present invention was administered to guinea pigs in order to examine whether the drug according to the fourth aspect of the present invention is highly safe.

Using the drug according to Example 1 of the fourth aspect of the present invention, a skin sensitization test was performed on guinea pigs by the maximization test method. The test was conducted by Life Science Laboratories, Ltd. As a result, it was found that the drug did not cause skin sensitization. This result demonstrates that the drug according to the fourth aspect of the present invention is highly safe.

Experimental Example 17 of Fourth Aspect of Invention

The drug according to the fourth aspect of the present invention was administered to humans in order to examine whether the drug according to the fourth aspect of the present invention is highly safe.

Using the drug according to Example 1 of the fourth aspect of the present invention, a human patch test was conducted by attaching patches impregnated with the drug to humans for 24 hours. The test was conducted by Life Science Laboratories, Ltd. As a result, it was found that the drug was non-irritating. This result demonstrates that the drug according to the fourth aspect of the present invention is highly safe.

Experimental Example 18 of Fourth Aspect of Invention

The present example examined whether the drug according to the fourth aspect of the present invention can inhibit the occurrence of rice blast.

Seeds of Koshihikari (rice cultivar) were subjected to seed selection with a salt solution, and diseased seeds were removed by removing floating seeds. The thus-selected seeds were washed with water, drained, and packed in a coarse saran fiber bag. Next, a diluted solution was prepared by diluting the drug according to Example 1 of the fourth aspect of the present invention 200-fold (also referred to as "200-fold dilution" hereinafter). Then, the seeds packed in the saran fiber bag were immersed in the 200-fold dilution twice as heavy as the seeds for 24 hours. During the immersion treatment, water replacement was not performed. After the immersion treatment, the seeds were air-dried, and then subjected to the immersion treatment again for 6 days. During the immersion treatment, water replacement was not performed. After the immersion treatment, the seeds were further subjected to the immersion treatment again for 6 days.

Next, the seeds were seeded in seedling boxes, and further, the 200-fold dilution was sprayed (500 ml/seedling box). Thereafter, the seeds were grown. The obtained seedlings were planted in a rice field, and cultivated by an ordinary method. Then, occurrence of rice blast during the cultivation was examined. As a control, the occurrence of rice blast was examined in the same manner, except that seeds of Hitomebore (rice cultivar) were used instead of the seeds of Koshihikari, the immersion treatments in the 200-fold dilution were not performed, and seedlings of Hitomebore were planted in a rice field adjacent to the rice field where the seedlings of Koshihikari were planted.

As a result, the occurrence of rice blast was not observed in the rice field where the seedlings obtained from the seeds subjected to the immersion treatments with the 200-fold dilution were planted. In contrast, in the control, the occurrence of rice blast was observed. These results demonstrate that the drug according to the fourth aspect of the present invention can inhibit the occurrence of rice blast.

Experimental Example 19 of Fourth Aspect of Invention

The present example examined whether the drug according to the fourth aspect of the present invention can restrict the spread of rice blast.

A rice field with a high incidence of rice blast was ploughed and irrigated while adding a diluted solution obtained by diluting the drug according to Example 1 of the fourth aspect of the present invention 10-fold (also referred to as "10-fold dilution" hereinafter) to the rice field (10 µl of the 10-fold dilution per 10 a of the rice field). Next, the seedlings of Koshihikari used in Experimental Example 18 of the fourth aspect of the invention were planted in a rice field after being ploughed and irrigated, and cultivated. Then, when the occurrence of rice blast was observed during the cultivation, stalks infected with rice blast were removed, and the 10-fold dilution was sprayed around areas where the stalks infected with rice blast had been cultivated (1 l of the 10-fold dilution per 10 a of the rice field). As a control, instead of the seedlings of Koshihikari obtained in Experimental Example 18 of the fourth aspect of the invention, the control seedlings in Experimental Example 18 of the fourth aspect of the invention were cultivated in the same manner, except that the control seedlings were planted in a rice field adjacent to the rice field where the seedlings of Koshihikari were planted, without adding or spraying the 10-fold dilution to the rice field. Then, whether the rice blast that had occurred in the rice field where the control seedlings were planted spread out to the rice field where the seedlings of Koshihikari were planted during the cultivation was examined.

As a result, in the rice field where the control seedlings were planted, the occurrence and spread of rice blast were observed. In contrast, in the rice field where the seedlings of Koshihikari were planted, while the occurrence of rice blast was observed slightly above primary rachis-branches in an area within about 2 to 3 m from the boundary to the rice field where the control seedlings were planted, the spread of the rice blast to the remaining area of the rice field was not observed. These results demonstrate that the drug according to the fourth aspect of the present invention can restrict the spread of rice blast.

Experimental Example 20 of Fourth Aspect of Invention

The present example examined whether the drug according to the fourth aspect of the present invention can repel shield bugs and pest insects.

The seedlings of Koshihikari obtained in Experimental Example 18 of the fourth aspect of the invention were planted in rice fields owned by 23 farmers and cultivated in the same manner as in the Experimental Example 19 of the fourth aspect of the invention, except that the rice fields were treated one by one by the respective farmers. Then, after the cultivation, each of the farmers was interviewed about the extent to which shield bugs and pest insects approached the rice field as compared with previous years.

As a result, eight farmers commented that repelling of shield bugs and pest insects was observed. These results demonstrate that the drug according to the fourth aspect of the present invention can repel shield bugs and pest insects.

While the present invention has been described above with reference to illustrative embodiments and examples, the present invention is by no means limited thereto. Various changes and modifications that may become apparent to those skilled in the art may be made in the configuration and specifics of the present invention without departing from the scope of the present invention.

INDUSTRIAL APPLICABILITY

Industrial Applicability of First Aspect of Invention

As specifically described above, according to the radical generating catalyst and radical production method of the first aspect of the present invention, it is possible to generate (produce) radicals under mild conditions. The radical generating catalyst and radical production method of the first aspect of the present invention can be used in, for example, the oxidation reaction product production method of the first aspect of the present invention. The oxidation reaction product production method of the first aspect of the present invention is applicable to oxidation reactions of various substances to be oxidized, including organic compounds and inorganic substances, and has a wide range of application potential. Further, the use of the radical generating catalyst and radical production method of the first aspect of the present invention is not limited to the oxidation reaction product production method of the first aspect of the present invention, and they are applicable to a wide variety of uses.

Industrial Applicability of Second Aspect of Invention

As specifically described above, according to the radical production method of the second aspect of the present invention, it is possible to generate (produce) radicals under mild conditions. The radical production method of the second aspect of the present invention can be used in, for example, the oxidation reaction product production method of the second aspect of the present invention. The oxidation reaction product production method of the second aspect of the present invention is applicable to oxidation reactions of various substances to be oxidized, including organic compounds and inorganic substances, and has a wide range of application potential. Further, the use of the radical production method of the second aspect of the present invention is not limited to the oxidation reaction product production method of the second aspect of the present invention, and they are applicable to a wide variety of uses.

Industrial Applicability of Third and Fourth Aspect of the Invention

As specifically described above, according to the third aspect of the present invention, it is possible to provide a drug that is highly safe and has a high sterilizing effect. Further, according to the fourth aspect of the present invention, it is possible to provide a drug for use in agriculture and livestock industry that is highly safe and has a high sterilizing effect. The use of the third and fourth aspects of the present invention is not particularly limited, and they are applicable to a wide variety of uses. The fourth aspect of the present invention is very useful in the fields of agriculture, livestock industry, etc., for example.

The invention claimed is:
1. A liquid drug comprising:
    a radical generating catalyst; and
    at least one selected from the group consisting of halogenous acids and halites, wherein
        the liquid drug is not acidic, and
        the radical generating catalyst comprises an ammonium salt represented by the following chemical formula (XI) (excluding peroxodisulfate) and has a Lewis acidity of 0.4 eV or more,
    wherein the radical generating catalyst catalyzes radical generation from a radical source in a liquid that is not acidic, and
    the radical source is at least one selected from the group consisting of halogenous acids-and halites:

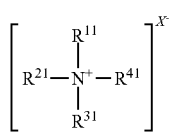
(XI)

where in the chemical formula (XI),
    and $R^{11}$, $R^{21}$, $R^{31}$, and $R^{41}$ are each a hydrogen atom or an alkyl group and may each comprise an ether bond, a carbonyl group, an ester bond, or an amide bond, or an aromatic ring, and $R^{11}$, $R^{21}$, $R^{31}$, and $R^{41}$ may be the same or different from each other, and
    $X^-$ is an anion (excluding a peroxodisulfate ion).

2. The liquid drug according to claim 1, wherein the halogenous acid is chlorous acid.

3. The liquid drug according to claim 1, further comprising water and/or an organic solvent.

4. A method for disinfection, comprising applying the liquid drug according to claim 1 to a subject to be disinfected, wherein the liquid drug is effective as a bactericide.

5. A liquid drug for use in agriculture and livestock industry comprising the liquid drug according to claim 1.

6. The liquid drug for use in agriculture and livestock industry, according to claim 5, which is
    at least one selected from the group consisting of bactericides for use in agriculture, antiviral agents for use in agriculture, deodorizers for use in agriculture, insecticides for use in agriculture, repellents for use in agriculture, soil conditioners for use in agriculture, bactericides for use in livestock industry, antiviral agents for use in livestock industry, deodorizers for use in livestock industry, insecticides for use in livestock industry, repellents for use in livestock industry, and soil conditioners for use in livestock industry.

* * * * *

UNITED STATES PATENT AND TRADEMARK OFFICE
CERTIFICATE OF CORRECTION

PATENT NO. : 10,870,102 B2
APPLICATION NO. : 16/062499
DATED : December 22, 2020
INVENTOR(S) : Takamori It is certified that error appears in the above-identified patent and that said Letters Patent is hereby corrected as shown below:

On the Title Page

(30) Foreign Application Priority Data, after "Dec. 18, 2015 (JP) ...... 2015-248068", add:
--Dec. 18, 2015 (JP) ...... 2015-248067
Dec. 18, 2015   (JP) ...... 2015-248069--.

Signed and Sealed this
Fifteenth Day of June, 2021

Drew Hirshfeld
*Performing the Functions and Duties of the
Under Secretary of Commerce for Intellectual Property and
Director of the United States Patent and Trademark Office*